(12) United States Patent
Janusz et al.

(10) Patent No.: US 7,504,517 B2
(45) Date of Patent: Mar. 17, 2009

(54) KV1.5 POTASSIUM CHANNEL INHIBITORS

(75) Inventors: John Michael Janusz, West Chester, OH (US); Stephen Joseph Hodson, Mason, OH (US); Gregory Kent Bosch, West Chester, OH (US); Ronald Eugene White, West Chester, OH (US); Benjamin E. Blass, Eagleville, PA (US); Christopher M. Jackson, Gahanna, OH (US); Neil T. Fairweather, Liberty Township, OH (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/765,359

(22) Filed: Jun. 19, 2007

(65) Prior Publication Data
US 2007/0299120 A1 Dec. 27, 2007

Related U.S. Application Data

(60) Provisional application No. 60/815,091, filed on Jun. 20, 2006.

(51) Int. Cl.
*C07D 233/38* (2006.01)
*A61K 31/4166* (2006.01)

(52) U.S. Cl. .................................. 548/322.1; 514/392

(58) Field of Classification Search ................ 514/392; 548/311.7, 322.1
See application file for complete search history.

(56) References Cited

U.S. PATENT DOCUMENTS

| | | | |
|---|---|---|---|
| 7,129,359 B2 | 10/2006 | Chern et al. | 546/274.4 |
| 2005/0267164 A1 | 12/2005 | Chern et al. | 514/341 |
| 2006/0117994 A1 | 6/2006 | Ryu et al. | 106/31.58 |

FOREIGN PATENT DOCUMENTS

| | | |
|---|---|---|
| EP | 0 587 134 | 3/1994 |
| EP | 0 612 741 | 8/1994 |
| JP | 2004-262903 | 9/2004 |
| WO | WO 97/27180 | 7/1997 |
| WO | WO 97/36892 | 10/1997 |
| WO | WO 03/057214 | 7/2003 |
| WO | WO 2004/046137 | 6/2004 |
| WO | WO 2006/027211 A1 | 3/2006 |
| WO | WO 03/048130 | 6/2006 |

OTHER PUBLICATIONS

G. Palazzo, et al.; "Reazioni Della N-Clorocarbonil-N-(2-Cloroetil)Anilina Con Idrazina E Con Idrazine Monosostituite" Farmaco, Edizione Scientifica; vol. 26; No. 6; 1971; pp. 580-590.
Rene Milcent, et al.; "Cyclic Transformations Of 5-Aryl(Or Benzyl)-3-(2-Bromoethyl-1,3,4-Oxadiazol-2(3*H*)-Ones Into 1-Aminoimidazolidin-2-One And 5,6-Dihydro-4*H*-1,3,4-Oxadiazine Derivatives" Journal of Heterocyclic Chemistry; vol. 29, Aug. 1992; pp. 1081-1084.
International Search Report And The Written Opinion of the International Searching Authority for International Application PCT/US2007/071587.
Blass, B. et al., "Synthesis of 1-aminoimidazolidin-4-one and 1-aminoimidazolidin-2-one based compounds: an interesting divergence in methodology," *Tetrahedron Lettters,* 2006, 47(42), 7497-7499; Caplus 2006:961586.

*Primary Examiner*—Kamal A Saeed
*Assistant Examiner*—Kristin Bianchi
(74) *Attorney, Agent, or Firm*—Ram W. Sabnis; Daniel Klein

(57) ABSTRACT

The present invention relates to 1-N-amino-2-imidazolidinones and derivatives thereof which are effective as Kv1.5 potassium channel inhibitors providing atrial-selective antiarrhythmic agents. The present invention further relates to compositions comprising said Kv1.5 potassium channel inhibitors, and to methods for treating cardiac arrhythmia.

30 Claims, No Drawings

KV1.5 POTASSIUM CHANNEL INHIBITORS

CROSS-REFERENCE TO RELATED APPLICATIONS

This application claims the benefit of U.S. Provisional Application No. 60/815,091 filed Jun. 20, 2006, which is herein incorporated by reference in its entirety

FIELD OF THE INVENTION

The present invention relates, inter alia, to compounds effective as Kv1.5 potassium channel inhibitors. The present invention further relates to inter alia, compositions comprising said Kv1.5 potassium channel inhibitors, and to methods for treating cardiac arrhythmia.

BACKGROUND OF THE INVENTION

Atrial fibrillation (AF) is the most frequently encountered cardiac arrhythmia in the clinical setting. It affects nearly 3 million people in the United States and its prevalence increases with the aging of the population. AF is most often treated with class III antiarrhythmic agents, acting at both the atrial and ventricular levels. Commonly used or prescribed antiarrhythmic drugs inhibit various potassium channels, and prolong ventricular repolarization. This prolongation can in turn precipitate the occurrence of life-threatening-ventricular arrhythmias, mainly Torsades de Pointes (TdP).

Atrial-selective antiarrhythmic agents offer the possibility of increased therapeutic efficacy and safety by minimizing cardiac proarrhythmia inherent in traditional antiarrhythmic therapies.

There is therefore a long felt need for atrial-selective antiarrhythmic agents which do not affect ventricular rhythm. In addition, there is a long felt need for atrial-selective antiarrhythmic agents which are compatible with other cardiac devices, protocols, therapies, and medications. The present invention addresses this and other needs.

SUMMARY OF THE INVENTION

The 1-N-amino-2-imidazolidinones of the present invention are a new class of compounds. Compounds of this class have been found to inhibit Kv1.5 potassium channels function.

Exemplary compounds of the present invention have formula (I):

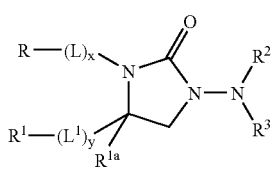

Formula (I)

wherein R is optionally substituted phenyl;
$R^1$ is optionally substituted phenyl, optionally substituted $C_1$-$C_6$ linear or branched alkyl, optionally substituted $C_3$-$C_7$ cycloalkyl, or optionally substituted heteroaryl;
$R^{1a}$ is hydrogen or $C_1$-$C_6$ linear or branched alkyl;
$R^2$ is hydrogen or is selected from
  i) —$SO_2[C(R^{5a}R^{5b})]_jR^4$;
  ii) —$C(O)[C(R^{5a}R^{5b})]_kR^4$; or
  iii) —$[C(R^{5a}R^{5b})]_nR^4$;
$R^3$ is hydrogen or is selected from:
  i) $C_1$-$C_4$ linear or branched alkyl, or $C_3$-$C_7$ cycloalkyl;
  ii) —$SO_2[C(R^{5a}R^{5b})]_jR^4$; or
  iii) —$[C(R^{5a}R^{5b})]_nR^4$; or
$R^2$ and $R^3$ are taken together with the atom to which they are bound to form an optionally substituted ring having from 3 to 7 ring atoms optionally containing one or more additional heteroatom ring atoms selected from N, O, or S;
$R^{5a}$ and $R^{5b}$ are each independently hydrogen or $C_1$-$C_4$ linear alkyl;
$R^4$ is selected from;
  i) hydrogen;
  ii) —$N(R^{6a}R^{6b})$;
  iii) —$SO_2R^7$;
  iv) —$C(O)N(R^{8a}R^{8b})$;
  v) optionally substituted $C_1$-$C_6$ linear or branched alkyl, or optionally substituted $C_3$-$C_6$ cycloalkyl;
  vi) optionally substituted $C_2$-$C_6$ linear or branched alkenyl;
  vii) optionally substituted $C_1$-$C_6$ linear or branched alkoxy;
  viii) optionally substituted $C_6$ or $C_{10}$ aryl;
  ix) optionally substituted $C_6$ or $C_{10}$ aryloxy;
  x) optionally substituted heteroaryl;
  xi) optionally substituted heterocycle; or
  xii) optionally substituted C(O)O(arylalkyl);
$R^{6a}$ and $R^{6b}$ are each independently hydrogen, optionally substituted $C_1$-$C_6$ linear or branched alkyl, optionally substituted $C_3$-$C_6$ cycloalkyl, optionally substituted benzyl, optionally substituted phenyl, or —$C(O)OR^{7a}$, or $R^{6a}$ and $R^{6b}$ are taken together with the atom to which they are bound to form a ring having from 3 to 7 ring atoms optionally containing one or more additional heteroatom ring atoms selected from N, O, or S;
$R^7$ is hydrogen, optionally substituted $C_1$-$C_6$ linear or branched alkyl, optionally substituted $C_3$-$C_6$ cycloalkyl, or $N(R^{7a})_2$;
$R^{7a}$ at each occurrence, independently, is hydrogen, optionally substituted $C_1$-$C_6$ linear or branched alkyl, or optionally substituted $C_3$-$C_6$ cycloalkyl;
$R^{8a}$ and $R^{8b}$ are each independently hydrogen, optionally substituted $C_1$-$C_6$ linear or branched alkyl, optionally substituted $C_3$-$C_6$ cycloalkyl, or $R^{8a}$ and $R^{8b}$ are taken together with the atom to which they are bound to form a ring having from 3 to 7 ring atoms optionally containing one or more additional heteroatom ring atoms selected from N, O, or S;
L and $L^1$ are, independently, —$[C(R^{9a}R^{9b})]_m$—;
$R^{9a}$ and $R^{9b}$ are, at each occurrence, each independently hydrogen or methyl, or $R^{9a}$ and $R^{9b}$ are taken together with the atom to which they are bound to form a cyclopropyl ring;
x and y are independently 0 or 1;
m, at each occurrence, independently is 0 to 4;
j, at each occurrence, independently is 0 to 4; and
k and n, at each occurrence, are independently 0 to 3; or a pharmaceutically acceptable salt form thereof.

The compounds of the present invention include compounds having formula (II):

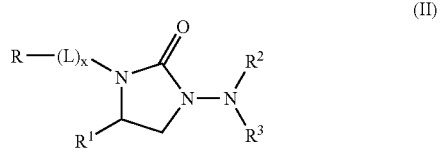

(II)

wherein R is phenyl or substituted phenyl;
$R^1$ is phenyl or substituted phenyl;
$R^2$ is hydrogen or is selected from:
  ii) —$SO_2[C(R^{5a}R^{5b})]_jR^4$;
  ii) —$C(O)[C(R^{5a}R^{5b})]_kR^4$; or
  iii) —$[C(R^{5a}R^{5b})]_nR^4$;
$R^3$ is hydrogen or is selected from:
  i) $C_1$-$C_4$ linear or branched alkyl, or $C_3$-$C_4$ cycloalkyl;
  ii) —$SO_2[C(R^{5a}R^{5b})]_jR^4$; or
  iii) —$[C(R^{5a}R^{5b})]_nR^4$; or
$R^2$ and $R^3$ are taken together with the atom to which they are bound to form an optionally substituted ring having from 3 to 7 ring atoms optionally containing one or more additional heteroatom ring atoms selected from N, O, or S;
$R^{5a}$ and $R^{5b}$ are each independently hydrogen or $C_1$-$C_4$ linear alkyl;
$R^4$ is selected from;
  i) hydrogen;
  ii) —$N(R^{6a}R^{6b})$;
  iii) —$SO_2R^7$;
  iv) —$C(O)N(R^{8a}R^{8b})$;
  v) optionally substituted $C_1$-$C_6$ linear or branched alkyl, or optionally substituted $C_3$-$C_6$ cycloalkyl;
  vi) optionally substituted $C_2$-$C_6$ linear or branched alkenyl;
  vii) optionally substituted $C_1$-$C_6$ linear or branched alkoxy or optionally substituted $C_3$-$C_6$ cyclic alkoxy;
  viii) optionally substituted $C_6$ or $C_{10}$ aryl;
  ix) optionally substituted $C_6$ or $C_{10}$ aryloxy;
  x) optionally substituted $C_1$-$C_{10}$ heteroaryl; or
  xi) optionally substituted $C_1$-$C_{10}$ heterocycle; or
$R^{6a}$ and $R^{6b}$ are each independently hydrogen, optionally substituted $C_1$-$C_6$ linear or branched alkyl, optionally substituted $C_3$-$C_6$ cycloalkyl, optionally substituted benzyl, or —$C(O)OR^7$, or $R^{6a}$ and $R^{6b}$ are taken together with the atom to which they are bound to form a ring having from 3 to 7 ring atoms optionally containing one or more additional heteroatom ring atoms selected from N, O, or S;
$R^7$ is hydrogen, optionally substituted $C_1$-$C_6$ linear or branched alkyl, optionally substituted $C_3$-$C_6$ cycloalkyl, $NH_2$, —$NH(C_1$-$C_4$ alkyl), or —$N(C_1$-$C_4$ alkyl)$_2$;
$R^{8a}$ and $R^{8b}$ are each independently hydrogen, optionally substituted $C_1$-$C_6$ linear or branched alkyl, optionally substituted $C_3$-$C_6$ cycloalkyl, or $R^{8a}$ and $R^{8b}$ are taken together with the atom to which they are bound to form a ring having from 3 to 7 ring atoms optionally containing one or more additional heteroatom ring atoms selected from N, O, or S;
L is —$[C(R^{9a}R^{9b})]_m$—;
$R^{9a}$ and $R^{9b}$ are each independently hydrogen or methyl;
x and y are independently 0 or 1;
m is 0 to 4;
j is 1 to 4; and
k and n are independently 0 to 3; or a pharmaceutically acceptable salt form thereof.

The present invention further relates to compositions comprising: an effective amount of one or more compounds according to the present invention and an excipient.

The present invention also relates to a method for treating or preventing cardiac arrhythmias, including, for example, atrial fibrillation and atrial flutter, said method comprising administering to a subject an effective amount of a compound or composition according to the present invention.

The present invention yet further relates to a method for treating or preventing cardiac arrhythmias, including, for example, atrial fibrillation or flutter, wherein said method comprises administering to a subject a composition comprising an effective amount of one or more compounds according to the present invention and an excipient.

The present invention also relates to a method for treating or preventing disease or conditions associated with cardiac arrhythmias, including, for example, thromboembolism, stroke, and heart failure. Said methods comprise administering to a subject an effective amount of a compound or composition according to the present invention.

The present invention yet further relates to a method for treating or preventing disease or conditions associated with cardiac arrhythmias, including, for example, thromboembolism, stroke, and heart failure, wherein said method comprises administering to a subject a composition comprising an effective amount of one or more compounds according to the present invention and an excipient.

The present invention also relates to a compound of the present invention for use in therapy, and to the use of a compound of the present invention for the manufacture of a medicament for treating or preventing conditions mentioned herein.

The present invention further relates to a process for preparing the Kv1.5 potassium channel inhibitors of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The Kv1.5 potassium channel inhibitors of the present invention are capable of selectively preventing arrhythmia in the atrial portion of the human heart or in the heart of certain animals. It has been discovered that functional Kv1.5 potassium channels are found in human atrial tissue but not in human ventricular myocytes. Without wishing to be limited by theory, it is believed the selective inhibition of the Kv1.5 voltage-gated Shaker-like potassium ($K^+$) ion channel can ameliorate, abate, or otherwise cause to be controlled, atrial fibrillation/flutter without prolonging ventricular repolarization.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2amino$, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $—CF_3$, $—CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle," whether used alone or as part of another group, are defined herein as one or more rings (e.g., 2 or 3 rings) having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the N to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

The terms "treat" and "treating," as used herein, refer to partially or completely alleviating, inhibiting, ameliorating and/or relieving a condition from which a patient is suspected to suffer.

As used herein, "therapeutically effective" refers to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

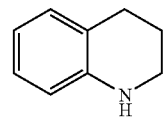

is, for the purposes of the present invention, considered a heterocyclic unit. 6,7-Dihydro-5H-cyclopentapyrimidine having the formula:

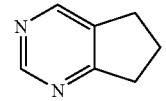

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

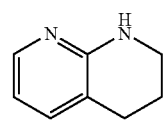

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (F, Cl, Br, I), —CN, —$NO_2$, oxo (=O), —$OR^{15}$, —$SR^{15}$, —$N(R^{15})_2$, —$NR^{15}C(O)R^{15}$, —$SO_2R^{15}$, —$SO_2OR^{15}$, —$SO_2N(R^{15})_2$, —$C(O)R^{15}$, —$C(O)OR^{15}$, —$C(O)N(R^{15})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^{15}$; wherein $R^{15}$, at each occurrence, independently is hydrogen, —$OR^{16}$, —$SR^{16}$, —$C(O)R^{16}$, —$C(O)OR^{16}$, —C(O)N$(R^{16})_2$, —$SO_2R^{16}$, —$S(O)_2OR^{16}$, —$N(R^{16})_2$, —$NR^{16}C(O)R^{16}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{15}$ units taken together with the atom(s) to which they are bound form an optionally substituted carbocycle or heterocycle wherein said carbocycle or heterocycle has 3 to 7 ring atoms; wherein $R^{16}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{16}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —$OR^{17}$; for example, —OH, —$OCH_3$, —$OCH_2CH_3$, —$OCH_2CH_2CH_3$;
ii) —$C(O)R^{17}$; for example, —$COCH_3$, —$COCH_2CH_3$, —$COCH_2CH_2CH_3$;
iii) —$C(O)OR^{17}$; for example, —$CO_2CH_3$, —$CO_2CH_2CH_3$, —$CO_2CH_2CH_2CH_3$;
iv) —$C(O)N(R^{17})_2$; for example, —$CONH_2$, —$CONHCH_3$, —$CON(CH_3)_2$;
v) —$N(R^{17})_2$; for example, —$NH_2$, —$NHCH_3$, —$N(CH_3)_2$, —$NH(CH_2CH_3)$;
vi) halogen: —F, —Cl, —Br, and —I;
vii) —$CH_mX_n$; wherein X is halogen, m is from 0 to 2, m+n=3; for example, —$CH_2F$, —$CHF_2$, —$CF_3$, —$CCl_3$, or —$CBr_3$;
viii) —$SO_2R^{17}$; for example, —$SO_2H$; —$SO_2CH_3$; —$SO_2C_6H_5$;
ix) $C_1$-$C_6$ linear, branched, or cyclic alkyl;
x) Cyano
xi) Nitro;
xii) $N(R^{17})C(O)R^{17}$;
xiii) Oxo (=O);
xiv) Heterocycle; and
xv) Heteroaryl.

wherein each $R^{17}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{17}$ units can be taken together to form a ring comprising 3-7 ring atoms. In certain aspects, each $R^{17}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the Kv1.5 potassium channel inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{15})_2$, each $R^{15}$ may be the same or different than the other). Combinations of substituents and/or variables are permissible only if such combinations result in stable compounds.

Kv1.5 Potassium Channel Inhibitors

The Kv1.5 potassium channel inhibitors of the present invention are 2-imidazoli-dinones, and include all enantiomeric and diastereomeric forms and salts thereof having the formula:

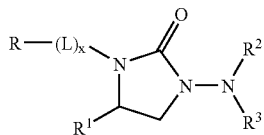

wherein the core scaffold is numbered in the following manner;

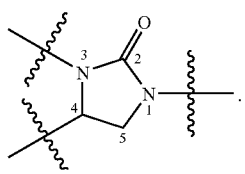

For the purposes of demonstrating the manner in which the compounds of the present invention are named and referred to herein, the compound having the formula:

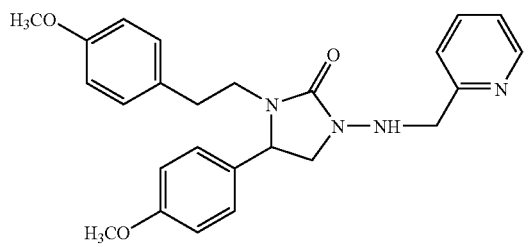

has the chemical name 4-(4-methoxyphenyl)-3-[2-(4-methoxyphenyl)ethyl]-1-[(pyridin-2-ylmethyl)amino]-imidazolidin-2-one.

For the purposes of the present invention, a compound depicted by the racemic formula, for example:

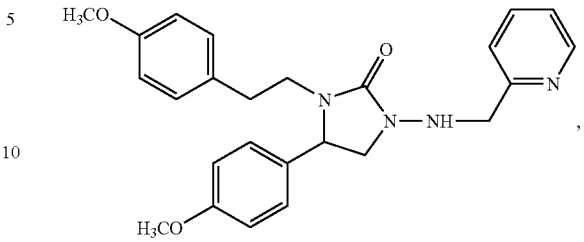

will stand equally well for either of the two enantiomers having the formula:

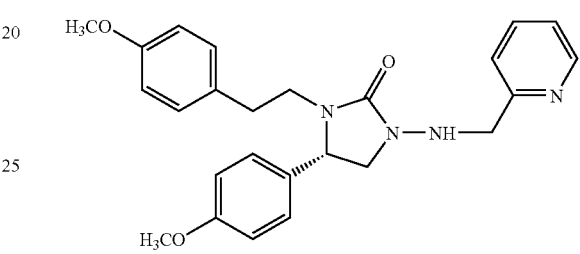

or the formula:

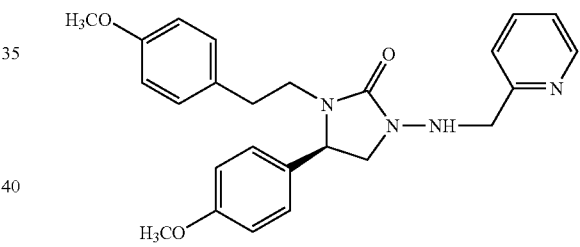

or in the case where a second chiral center is present, all diastereomers. However, the term 1-N-amino-2-imidazolidinones is used in general to refer to the genus, which encompasses the compounds of the present invention, throughout the specification.

The particular embodiments and illustrations herein relating to particular aspects of the present invention may be combined in the compounds of the present invention.

In the present invention, R is optionally substituted phenyl. The phenyl group can be substituted with any of the substituents provided herein. Examples of suitable substituents include, but are not limited to halogen, optionally substituted $C_1$-$C_6$ linear or branched alkyl, optionally substituted $C_1$-$C_6$ linear or branched haloalkyl, optionally substituted $C_3$-$C_6$ cycloalkyl, —$OR^{13}$, —CN, —$N(R^{13})_2$, —$CO_2R^{13}$, —C(O)$N(R^{13})_2$, —$NR^{13}C(O)R^{13}$, —$NO_2$, and —$SO_2R^{13}$; each $R^{13}$ is independently hydrogen, optionally substituted $C_1$-$C_6$ (e.g., $C_1$-$C_4$) linear or branched alkyl, optionally substituted $C_1$-$C_6$ (e.g., $C_1$-$C_4$) linear or branched haloalkyl, optionally substituted $C_3$-$C_6$ cycloalkyl (e.g., $C_3$-$C_4$ cycloalkyl), optionally substituted aryl, optionally substituted heterocycle, or optionally substituted heteroaryl, or two $R^{13}$ units can be taken together to form a ring comprising from 3-7 ring atoms.

When two $R^{13}$ units are taken together to form a ring, the ring may comprise additional heteroatoms independently selected from oxygen, nitrogen, or sulfur and may be optionally substituted. Non-limiting examples of two $R^{13}$ unit derived rings include piperidinyl, piperazinyl, morpholinyl, and pyrrolidinyl. In certain aspects, the substituents on the optionally substituted linear or branched alkyl group is a $C_3$-$C_6$ cycloalkyl. The phenyl group can be substituted at any position on the ring, e.g., meta, para, and/or ortho positions.

Exemplary embodiments of the present invention include a compound of Formulas (I)-(XIX), or a pharmaceutically acceptable salt form thereof, wherein R is phenyl optionally substituted with —$OCH_3$ and —$OCHF_2$, for example, 4-methoxyphenyl or 4-difluoro-methoxyphenyl.

Exemplary embodiments of the present invention include a compound of Formulas (I)-(XIX), or a pharmaceutically acceptable salt form thereof, wherein R is phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,5-trifluorophenyl, 3,4,5-trifluorophenyl, 2,4,6-trifluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, or 2,4,6-trichlorophenyl.

Exemplary embodiments of the present invention include a compound of Formulas (I)-(XIX), or a pharmaceutically acceptable salt form thereof, wherein R is phenyl optionally substituted with halogen substituted alkoxy units, non-limiting examples of which include 2-fluoromethoxyphenyl, 3-fluoromethoxyphenyl, 4-fluoromethoxyphenyl, 2-difluoromethoxyphenyl, 3-difluoromethoxyphenyl, 4-difluoromethoxyphenyl, 2-trifluoromethoxyphenyl, 3-tri-fluoromethoxyphenyl, or 4-trifluoromethoxyphenyl Exemplary embodiments of the present invention include a compound of Formulas (I)-(XIX), or a pharmaceutically acceptable salt form thereof, wherein R is 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 3,4,5-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 3,4,5-triethylphenyl, or 2,4,6-triethylphenyl.

Exemplary embodiments of the present invention include a compound of Formulas (I)-(XIX), or a pharmaceutically acceptable salt form thereof, wherein R is 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 2-hydroxyphenyl, 3-hydroxyphenyl, 4-hydroxyphenyl, 2,3-dihydroxyphenyl, 2,4-dihydroxyphenyl, 2,5-dihydroxy-phenyl, 2,6-dihydroxyphenyl, 3,4-dihydroxyphenyl, 2,3,4-trihydroxyphenyl, 2,3,5-trihydroxyphenyl, 2,3,6-trihydroxyphenyl, 2,4,5-trihydroxyphenyl, 3,4,5-trihydroxyphenyl, or 2,4,6-trihydroxy-phenyl.

Exemplary embodiments of the present invention include a compound of Formulas (I)-(XIX), or a pharmaceutically acceptable salt form thereof, wherein R is 2-cyanophenyl, 3-cyanophenyl, 4-cyanophenyl, 2,3-dicyanophenyl, 2,4-dicyanophenyl, 2,5-dicyanophenyl, 2,6-dicyanophenyl, 3,4-dicyanophenyl, 3,5-dicyanophenyl, 2,3,4-tricyanophenyl, 2,3,5-tricyanophenyl, 2,3,6-tricyanophenyl, 2,4,5-tricyanophenyl, 3,4,5-tricyanophenyl, or 2,4,6-tricyanophenyl.

Exemplary embodiments of the present invention include a compound of Formulas (I)-(XIX), or a pharmaceutically acceptable salt form thereof, wherein R is 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,4-dinitrophenyl, 3,5-dinitrophenyl, 2,3,4-trinitrophenyl, 2,3,5-trinitrophenyl, 2,3,6-trinitrophenyl, 2,4,5-trinitrophenyl, 3,4,5-trinitrophenyl, or 2,4,6-trinitrophenyl.

Exemplary embodiments of the present invention include a compound of Formulas (I)-(XIX), or a pharmaceutically acceptable salt form thereof, wherein R is 2,6-dimethyl-4-fluorophenyl, 2,6-dimethyl-3-fluorophenyl, 2,6-dimethyl-4-chlorophenyl, 2,6-di-tert-butyl-4-hydroxyphenyl, 2,6-difluoro-4-chlorophenyl, 2,6-difluoro-3-chlorophenyl, 2-hydroxy-4-methylphenyl, 2-hydroxy-5-methylphenyl, 2,6-dihydroxy-4-tert-butylphenyl, or 2,6-difluoro-4-cyanophenyl.

Exemplary embodiments of the present invention include a compound of Formulas (I)-(XIX), or a pharmaceutically acceptable salt form thereof, wherein R is 3-dimethylaminophenyl, 4-dimethylaminophenyl, 3-diethylaminophenyl, 4-diethylaminophenyl, 3-methylsulfanylphenyl, 4-methylsulfanyl-phenyl, 3-ethylsulfanylphenyl, 4-ethylsulfanylphenyl, 3-propylsulfanylphenyl, or 4-propylsulfanylphenyl.

Exemplary embodiments of the present invention include a compound of Formulas (I)-(XIX) or a pharmaceutically acceptable salt form thereof, wherein R is 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino) phenyl, or 4-(N,N-diethylamino)phenyl.

In the present invention, $R^1$ is optionally substituted phenyl, optionally substituted $C_1$-$C_6$ linear or branched alkyl, optionally substituted $C_3$-$C_7$ cyclic alkyl, or optionally substituted heteroaryl.

In certain aspects, $R^1$ is optionally substituted phenyl. The phenyl group can be substituted with any of the substituents provided herein. Examples of suitable substituents include, but are not limited to halogen, optionally substituted $C_1$-$C_6$ linear or branched alkyl, optionally substituted $C_1$-$C_6$ linear or branched haloalkyl, optionally substituted $C_3$-$C_6$ cycloalkyl, —$OR^{13}$, —CN, —$N(R^{13})_2$, —$CO_2R^{13}$, —C(O)N($R^{13}$)$_2$, —$NR^{13}$C(=O)$R^{13}$, —$NO_2$, and —$SO_2R^{13}$; each $R^{13}$ is independently hydrogen, optionally substituted $C_1$-$C_6$ (e.g., $C_1$-$C_4$) linear or branched alkyl, optionally substituted $C_1$-$C_6$ (e.g., $C_1$-$C_4$) linear or branched haloalkyl, optionally substituted $C_3$-$C_6$ cycloalkyl (e.g., $C_3$-$C_4$ cycloalkyl), optionally substituted aryl, optionally substituted heterocycle, or optionally substituted heteroaryl, or two $R^{13}$ units can be taken together to form a ring comprising from 3-7 ring atoms. When two $R^{13}$ units are taken together to form a ring, the ring may comprise additional heteroatoms independently selected from oxygen, nitrogen, or sulfur and may be optionally substituted. Non-limiting examples of two $R^{13}$ unit derived rings include piperidinyl, piperazinyl, morpholinyl, and pyrrolidinyl. In certain aspects, the substituent on the optionally substituted linear or branched alkyl group is a $C_3$-$C_6$ cycloalkyl.

The phenyl group can be substituted at any position on the ring, e.g., meta, para, and/or ortho positions.

Exemplary embodiments of the present invention include a compound of Formulas (I)-(XIX), or a pharmaceutically acceptable salt form thereof, wherein $R^1$ is 4-methyl-phenyl, 4-fluorophenyl, 4-chlorophenyl, 4-(fluoromethyl)phenyl, 4-(difluoromethoxy)-phenyl, 4-(trifluoromethyl)phenyl, 4-methoxyphenyl, 3-methyl-4-methoxyphenyl, 3-methoxy-4-methylphenyl, 3,4-di-methoxyphenyl, 3,4-dimethylphenyl, 4-cyclopropyl-phenyl, 4-tert-butylphenyl, or 4-(2-methoxyethoxy)phenyl.

Exemplary embodiments of the present invention include a compound of Formulas (I)-(XIX), or a pharmaceutically acceptable salt form thereof, wherein $R^1$ is optionally substituted phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, or 2,4,6-trichlorophenyl.

Exemplary embodiments of the present invention include a compound of Formulas (I)-(XIX), or a pharmaceutically acceptable salt form thereof, wherein $R^1$ is 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethyl-phenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, or 4-isopropylphenyl.

Exemplary embodiments of the present invention include a compound of Formulas (I)-(XIX), or a pharmaceutically acceptable salt form thereof, wherein $R^1$ has the formula:

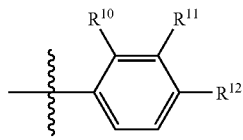

wherein $R^{10}$ and $R^{11}$ or $R^{11}$ and $R^{12}$ are taken together with the atom to which they are bound to form an optionally substituted ring having from 5 to 7 ring atoms, optionally containing one or more hetoroatoms independently selected from N, O, or S, Non-limiting examples of $R^1$ unit according to this aspect include benzo[1,3]-dioxol-4-yl, 2-methylbenzo[1,3]dioxol-4-yl, 2,2-difluorobenzo[1,3]dioxol-4-yl, 2-methylbenzo[1,3]dioxol-5-yl, 2,2-dimethylbenzo[1,3]dioxol-5-yl, 2,2-difluorobenzo[1,3]-dioxol-5-yl, 2-methyl-2,3-dihydrobenzo[1,4]-dioxin-5-yl, 2-hydroxymethyl-2,3-dihydrobenzo[1,4]dioxin-5-yl, 2,3-dihydro-benzo[1,4]dioxin-6-yl, 2-methyl-2,3-dihydrobenzo[1,4]dioxin-6-yl, and 2-hydroxymethyl-2,3-dihydrobenzo-[1,4]dioxin-6-yl.

Exemplary embodiments of the present invention include a compound of Formulas (I)-(XIX), or a pharmaceutically acceptable salt form thereof, wherein $R^1$ is 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino) phenyl, and 4-(N,N-diethylamino)phenyl.

Compounds of the present invention include a compound of Formulas (I)-(XIX), or a pharmaceutically acceptable salt form thereof, wherein $R^1$ is butyl, cyclohexyl, quinolinyl, pyrrolidinyl, or 6-methoxypyrridin-3-yl.

Compounds of the present invention include those wherein the substituent on the $C_1$-$C_6$ optionally substituted linear or branched alkyl of $R^{8a}$ and $R^{8b}$ is $C_3$-$C_6$ cycloalkyl.

Compounds of the present invention include those wherein $R^{1a}$ is hydrogen.

Compounds of the present invention include those wherein the heteroaryl of $R^4$ is a $C_{1-10}$ heteroaryl and the heterocycle of $R^4$ is a $C_{1-10}$ heterocycle.

Compounds of the present invention include those wherein $R^2$ and $R^3$ are both hydrogen. Also included in the present invention are compounds wherein $R^2$ and $R^3$ are not both hydrogen. Also included in the present invention are compounds wherein when one of $R^2$ and $R^3$ is hydrogen or optionally substituted alkyl, the other of $R^2$ and $R^3$ is not hydrogen or optionally substituted alkyl.

Compounds of the present invention include those wherein $R^2$ and $R^3$ can be taken together to form dioxidoisothiazolidinyl or piperazinyl optionally substituted with —C(O)NH$_2$, or —C(O)CH$_3$.

Compounds f of the present invention include those wherein the heteroaryl and heterocycle groups of the present invention are independently selected from pyridinyl, furanyl, isoxazolyl, quinolinyl, imidazolyl, morpholinyl, piperidinyl, piperazinyl, or pyrazinyl.

Compounds of the present invention include those wherein $R^2$ is —SO$_2$[C(R$^{5a}$R$^{5b}$)]$_j$R$^4$ and j is 0 (i.e., $R^2$ is —SO$_2$R$^4$) and $R^4$ is —N(R$^{6a}$R$^{6b}$), optionally substituted $C_1$-$C_6$ linear or branched alkyl, or optionally substituted $C_3$-$C_6$ cycloalkyl. Non-limiting examples of $R^4$ include —NH$_2$, methyl, fluoromethyl, difluoromethyl, chloromethyl, dichloromethyl, trichloromethyl, ethyl, 2,2,2-trifluoroethyl, 2,2,2-trichloroethyl, n-propyl, iso-propyl, cyclopropyl, n-butyl, iso-butyl, tert-butyl, and cyclobutyl.

Compounds of the present invention include those wherein $R^2$ is SO$_2$[C(R$^{5a}$R$^{5b}$)]$_j$R$^4$; wherein $R^4$ is optionally substituted phenyl, $C_4$-$C_5$ optionally substituted heterocycle, or $C_3$-$C_5$ optionally substituted heteroaryl; and j is 0, 1, 2 or 3. Non-limiting examples of $R^4$ include phenyl, furan-2-yl, isoxazol-5-yl, imidazol-1-yl, pyridin-2-yl, pyridin-3-yl, pyridin-4-yl, pyrazin-2-yl, piperidin-1-yl, 4-methylpiperidin-1-yl, piperazin-1-yl, 4-methylpiperazin-1-yl, and morpholin-4-yl. In certain embodiments, j is 1, 2, or 3. In some embodiments $R^{5a}$ and $R^{5b}$ are each hydrogen (i.e. $R^2$ is —SO$_2$(CH$_2$)$_j$R$^4$).

Compounds of the present invention include those wherein $R^2$ is (piperidin-1-yl-ethyl)sulfonyl, (4-methylpiperidin-1-yl-ethyl)sulfonyl, (piperazin-1-yl-ethyl)sulfonyl, (4-methylpiperazin-1-yl-ethyl)sulfonyl, or (morpholin-4-yl-ethyl)sulfonyl.

Compounds of the present invention include those wherein $R^2$ is —SO$_2$[C(R$^{5a}$R$^{5b}$)]$_j$R$^4$ and j is 0 (i.e., $R^2$ is —SO$_2$R$^4$) wherein $R^4$ is optionally substituted $C_1$-$C_6$ linear or branched alkyl, optionally substituted $C_3$-$C_6$ cycloalkyl, or optionally substituted $C_2$-$C_6$ linear or branched alkenyl. Non-limiting examples of $R^4$ include methyl, ethyl, n-propyl, iso-propyl, n-butyl, sec-butyl, iso-butyl, tert-butyl, fluoromethyl, chloromethyl, cyanomethyl, trifluoromethyl, CH$_2$CF$_3$, cyclopropyl, cyclobutyl, cyclopentyl, cyclohexyl and alkenyl. Compounds of the present invention include those wherein $R^2$ is methanesulfonyl.

Compounds of the present invention include those wherein $R^2$ is methanesulfonyl and $R^3$ is hydrogen.

Compounds of the present invention include those wherein $R^2$ is —C(O)[C($R^{5a}R^{5b}$)]$_k R^4$ and k is 0 (i.e., $R^2$ is —C(O)$R^4$) and $R^4$ is optionally substituted $C_1$-$C_6$ linear or branched alkyl or optionally substituted $C_3$-$C_6$ cycloalkyl. Non-limiting examples of $R^4$ include methyl, fluoromethyl, difluoromethyl, trifluoromethyl, (N-methyl-N-benzyl)aminomethyl, (N-methyl-N-tert-butoxycarbonyl)aminomethyl, ethyl, 2,2,2-trifluoroethyl, 2,2,2-trichloroethyl, n-propyl, iso-propyl, cyclopropyl, n-butyl, iso-butyl, tert-butyl, cyclopropylmethyl, and cyclobutyl.

Compounds of the present invention include those wherein $R^2$ is —C(O)[C($R^{5a}R^{5b}$)]$_k R^4$ and $R^4$ is optionally substituted phenyl or naphthyl. In some embodiments $R^{5a}$ and $R^{5b}$ are each hydrogen (i.e. $R^2$ is —C(O)(CH$_2$)$_k R^4$). Non-limiting examples of $R^4$ include phenyl, 4-fluoro-phenyl, 4-chlorophenyl, 4-(trifluoromethyl)phenyl, 4-methoxyphenyl, and 4-(trifluoromethoxy)phenyl.

Compounds of the present invention include those wherein $R^2$ is —C(O)[C($R^{5a}R^{5b}$)]$_k R^4$; $R^4$ is optionally substituted $C_1$-$C_{10}$ heteroaryl, or optionally substituted $C_1$-$C_{10}$ heterocycle; and k is 0 to 2. In some embodiments $R^{5a}$ and $R^{5b}$ are each hydrogen (i.e. $R^2$ is —C(O)(CH$_2$)$_k R^4$). Non-limiting examples of $R^4$ include furan-2-yl, isoxazol-5-yl, imidazol-1-yl, pyridin-2-yl, pyridin-3-yl, pyridin-4-yl, pyrazin-2-yl, piperidin-1-yl, 4-methylpiperidin-1-yl, piperazin-1-yl, 4-methylpiperazin-1-yl, and morpholin-4-yl.

Compounds of the present invention include those wherein $R^2$ is —C(O)[C($R^{5a}R^{5b}$)]$_k R^4$; $R^4$ is optionally substituted methoxy, optionally substituted ethoxy, optionally substituted n-propoxy, optionally substituted iso-propoxy, optionally substituted n-butoxy, optionally substituted iso-butoxy, or optionally substituted tert-butoxy; and k is 1 or 2. In some embodiments $R^{5a}$ and $R^{5b}$ are each hydrogen (i.e. $R^2$ is —C(O)(CH$_2$)$_k R^4$).

Compounds of the present invention include those wherein $R^2$ is —[C($R^{5a}R^{5b}$)]$_n R^4$; $R^4$ is optionally substituted aryl, optionally substituted aryloxy, optionally substituted $C_3$-$C_9$ heterocycle, or optionally substituted $C_3$-$C_9$ heteroaryl; and n is 1 or 2. In some embodiments $R^{5a}$ and $R^{5b}$ are each hydrogen (i.e. $R^2$ is —(CH$_2$)$_n R^4$). Non-limiting examples of $R^4$ include phenyl, quinolin-2-yl, pyridin-2-yl, pyridin-3-yl, pyridin-4-yl, 4-dimethylaminophenyl, 4-diethylaminophenyl, 4-fluorophenyl, 4-chlorophenyl, 4-(imidazol-1-yl)phenyl, and 4-cyanophenyl.

Compounds of the present invention include those wherein $R^2$ is —C(O)[C($R^{5a}R^{5b}$)]$_k$N($R^{6a}R^{6b}$) wherein $R^{6b}$ is hydrogen or methyl; $R^{6b}$ is —C(O)O$R^{7a}$; and $R^{7a}$ is methyl, ethyl, or tert-butyl. Non-limiting examples of $R^2$ include —C(O)CH$_2$NHC(O)OC(CH$_3$)$_3$, —C(O)CH$_2$N(CH$_3$)C(O)OC(CH$_3$)$_3$ and —C(O)CH$_2$N(CH$_3$)C(O)OCH$_3$.

Compounds of the present invention include those wherein $R^2$ is —C(O)[C($R^{5a}R^{5b}$)]$_k$N($R^{6a}R^{6b}$) wherein $R^{6b}$ is hydrogen or methyl, and $R^{6a}$ is optionally substituted benzyl.

Compounds of the present invention include those wherein $R^2$ is C(O)CH$_3$, C(O)OCH$_3$, —C(O)cyclopropyl, C(O)OC(CH$_3$)$_3$, C(O)CH$_2$N(CH$_3$)benzyl, C(O)CH$_2$N(CH$_3$)C(O)O$R^{7a}$, —C(O)furan-2-yl, C(O)C$_6$H$_5$, C(O)CH$_2$C$_6$H$_5$, C(O)CH$_2$OC$_6$H$_5$, —C(O)isoxazol-5-yl, —C(O)pyrazin-2-yl, —CH$_2$(cyclopropyl), CH$_2$C$_6$H$_5$, CH$_2$CH$_2$C$_6$H$_5$, CH$_2$C$_6$H$_4$(4-CN), CH$_2$C$_6$H$_4$(4-F), —CH$_2$C$_6$H$_4$[4-N(CH$_3$)$_2$], —CH$_2$C$_6$H$_4$[4-N(C$_2$H$_5$)$_2$], —CH$_2$C$_6$H$_4$[4-imidazolyl], —CH$_2$(imidazol-1-yl), —CH$_2$(pyridine-2-yl), CH$_2$(pyridine-3-yl), or CH$_2$(pyridine-4-yl) and $R^{7a}$ is tert-butyl.

Compounds of the present invention include those wherein $R^2$ is SO$_2$R$_4$, SO$_2$CH$_2$C(O)N($R^{8a}R^{8b}$), SO$_2$[C($R^{5a}R^{5b}$)]$_j$ SO$_2$—$R^7$, or SO$_2$[C($R^{5a}R^{5b}$)]$_j R^4$.

Compounds of the present invention include those wherein $R^3$ is hydrogen, optionally substituted $C_1$-$C_4$ linear or branched alkyl, or optionally substituted $C_3$-$C_4$ cycloalkyl. Non-limiting examples include methyl, ethyl, n-propyl, iso-propyl, and cyclopropyl.

Compounds of the present invention include those wherein $R^2$ is hydrogen, SO$_2$R$_4$, SO$_2$CH$_2$C(O)N($R^{8a}R^{8b}$), SO$_2$[C($R^{5a}R^{5b}$)]$_j$SO$_2$—$R^7$, or SO$_2$[C($R^{5a}R^{5b}$)]$_j R^4$; $R^4$ is —NH$_2$, —CH$_3$, —CH$_2$CH$_3$, —CH$_2$CH$_2$CH$_3$, —CH$_2$CH$_2$CH$_2$CH$_3$, —CH$_2$F, —CH$_2$Cl, —CCl$_3$, —CH$_2$CH$_2$F, —CH$_2$CHF$_2$, —CH$_2$CF$_3$, -cyclopropyl, —CH=CH$_2$, CHF$_2$, CHCl$_2$, —CH$_2$CN, -(pyridin-2-yl), -(pyridin-3-yl), -(pyridin-4-yl), or —C$_6$H$_5$; $R^{8a}$ is hydrogen, —CH$_3$, -cyclopropyl, or —CH$_2$(cyclopropyl); $R^{8b}$ is hydrogen, —CH$_3$, -cyclopropyl, or —CH$_2$(cyclopropyl); $R^{5a}$ is hydrogen; $R^{5b}$ is hydrogen; $R^7$ is —CH$_3$, —CH$_2$CH$_3$, —CH$_2$CH$_2$CH$_3$, —CH$_2$CH$_2$CH$_2$CH$_3$, or -cyclopropyl, and j is 0, 1 or 2

Compounds of the present invention include those wherein when $R^2$ or $R^3$ is —[C($R^{5a}R^{5b}$)]$_n R^4$, then $R^4$ is not aryloxy.

Compounds of the present invention include those wherein $R^2$ and $R^3$ are taken together form an optionally substituted ring having from 3 to 7 ring atoms, then R is phenyl optionally substituted by at least one alkoxy substituent.

Compounds of the present invention include those wherein j is zero.

Compounds of the present invention include those wherein j is from 1 to 4.

Compounds of the present invention include those wherein when $R^2$ is —C(O)[C($R^{5a}R^{5b}$)]$_k R^4$, wherein $R^4$ is optionally substituted linear or branched alkoxy, then $R^3$ is not —[C($R^{5a}R^{5b}$)]$_n R^4$ wherein $R^4$ is optionally substituted quinolinyl.

Compounds of the present invention include those wherein when $R^2$ is —C(O)[C($R^{5a}R^{5b}$)]$_k R^4$ wherein $R^4$ is optionally substituted linear or branched alkoxy, then $R^3$ is not —[C($R^{5a}R^{5b}$)]$_n R^4$ wherein $R^4$ is optionally substituted heteroaryl.

Compounds of the present invention include those wherein when $R^3$ is hydrogen, then $R^2$ is not —C(O)[C($R^{5a}R^{5b}$)]$_k R^4$ wherein $R^4$ is optionally substituted aryloxy.

Compounds of the present invention include those wherein when $R^3$ is hydrogen, then $R^2$ is not —SO$_2$[C($R^{5a}R^{5b}$)]$_j R^4$ wherein $R^4$ is —N($R^{6a}R^{6b}$) and one of $R^{6a}$ and $R^{6b}$ is hydrogen and the other is —C(O)O$R^{7a}$ when $R^{7a}$ is optionally substituted linear or branched alkyl.

Compounds of the present invention include those wherein when $R^2$ and $R^3$ are hydrogen, then R is substituted phenyl.

Compounds of the present invention include those wherein when $R^2$ is —SO$_2$[C($R^{5a}R^{5b}$)]$_j R^4$ wherein $R^4$ is phenyl or naphthyl, then $R^3$ is not SO$_2$[C($R^{5a}R^{5b}$)]$_j R^4$ wherein $R^4$ is phenyl or naphthyl.

Compounds of the present invention include those wherein when $R^3$ is —C(O)[C($R^{5a}R^{5b}$)]$_k R^4$ wherein $R^4$ is phenyl or naphthyl, then $R^2$ is not hydrogen.

Compounds of the present invention include those wherein when $R^3$ is —C(O)[C($R^{5a}R^{5b}$)]$_k R^4$ wherein $R^4$ is —N($R^{6a}R^{6b}$) and one of $R^{6a}$ and $R^{6b}$ is hydrogen and the other is phenyl, then $R^2$ is not hydrogen.

Compounds of the present invention include those wherein when $R^2$ is —SO$_2$[C($R^{5a}R^{5b}$)]$_j R^4$ wherein $R^4$ is hydrogen or linear or branched alkyl, then $R^3$ is not —[C($R^{5a}R^{5b}$)]$_j R^4$ wherein $R^4$ is optionally substituted imidazolyl.

Compounds of the present invention include those wherein when $R^2$ is —SO$_2$[C($R^{5a}R^{5b}$)]$_j R^4$ wherein $R^4$ is hydrogen or linear or branched alkyl, then $R^3$ is not —[C($R^{5a}R^{5b}$)]$_j R^4$ wherein $R^4$ is optionally substituted heteroaryl.

Compounds of the present invention include those wherein when $R^2$ is —SO$_2$[C($R^{5a}R^{5b}$)]$_j R^4$ wherein $R^4$ is pyridinyl, then $R^3$ is not hydrogen.

Compounds of the present invention include those wherein when $R^2$ is —SO$_2$[C($R^{5a}R^{5b}$)]$_j R^4$ wherein $R^4$ is optionally substituted heteroaryl, then $R^3$ is not hydrogen.

Compounds of the present invention include those wherein when $R^2$ is C(O)[C($R^{5a}R^{5b}$)]$_k R^4$ wherein $R^4$ is hydrogen or linear or branched alkyl, then $R^3$ is not hydrogen.

Compounds of the present invention include those wherein when $R^2$ is —SO$_2$[C($R^{5a}R^{5b}$)]$_j R^4$ wherein $R^4$ is C(O)NR$^{8a}R^{8b}$ and R$^{8a}R^{8b}$ form a piperazinyl ring substituted with acetyl, then $R^3$ is not hydrogen.

Compounds of the present invention include those wherein when $R^2$ is —SO$_2$[C($R^{5a}R^{5b}$)]$_j R^4$ wherein $R^4$ is C(O)NR$^{8a}R^{8b}$ and R$^{8a}R^{8b}$ form a ring having from 3 to 7 ring atoms, then $R^3$ is not hydrogen.

In all of the embodiments provided herein, examples of suitable optional substituents are not intended to limit the scope of the claimed invention. The compounds of the invention may contain any of the substituents, or combinations of substituents, provided herein.

Compounds of the present invention include those wherein $R^7$ is hydrogen, optionally substituted $C_1$-$C_6$ linear or branched alkyl, optionally substituted $C_3$-$C_6$ cycloalkyl, NH$_2$, —NH($C_1$-$C_4$ alkyl), or —N($C_1$-$C_4$ alkyl)$_2$.

Compounds of the present invention include those wherein $R^{9a}$ and $R^{9b}$ are, at each occurrence, each independently hydrogen or methyl, or when m is 1, $R^{9a}$ and $R^{9b}$ can be taken together with the atom to which they are bound to form a cyclopropyl ring.

Compounds of the present invention include those wherein L and L$^1$ are, independently, —[C($R^{9a}R^{9b}$)]$_m$— and $R^{9a}$ and $R^{9b}$ are at each occurrence, each independently hydrogen or methyl, or $R^{9a}$ and $R^{9b}$ can be taken together to form a cyclopropyl ring.

In some embodiments, y is 0 (i.e., L$^1$ is absent). In other embodiments, y is 1 and L$^1$ is —CH$_2$—. In still other embodiments, y is 1 and L$^1$ is:

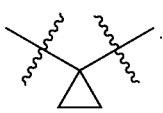

In certain aspects, L is —[C($R^{9a}R^{9b}$)]$_m$— wherein $R^{9a}$ and $R^{9b}$ are, at each occurrence, each independently hydrogen or methyl; x is 0 or 1; and m is 0 to 4. When x is equal to 0, linking group L is absent, when x is equal to 1, linking group L is present.

Compounds of the present invention include those wherein L is —CH$_2$CH$_2$— (ethylene) (i.e., $R^{9a}$ and $R^{9b}$ are each a hydrogen and m is 2).

Compounds of the present invention include compounds having Formulas III or IV, or a pharmaceutically acceptable salt form thereof:

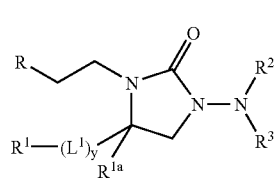

Formula III

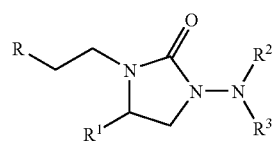

Formula IV wherein R, R$^1$, R$^{1a}$, R$^2$, and R$^3$ are the same as defined herein.

Compounds of the present invention include those wherein L is —CH$_2$-(methylene) (i.e., $R^{9a}$ and $R^{9b}$ are each a hydrogen and m is 1).

Compounds of the present invention include those having Formulas V or VI or a pharmaceutically acceptable salt form thereof:

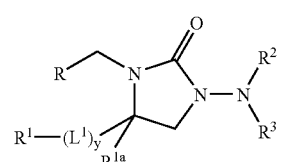

Formula V

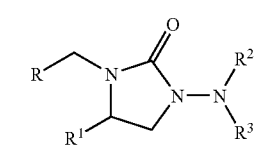

Formula VI wherein R, R$^1$, R$^{1a}$, R$^2$, and R$^3$ are the same as defined herein.

Compounds of the present invention include those wherein L is —CH$_2$CH$_2$CH$_2$— (propylene) (i.e., $R^{9a}$ and $R^{9b}$ are each a hydrogen and m is 3).

Compounds of the present invention include compounds having Formulas VII or VIII or a pharmaceutically acceptable salt form thereof:

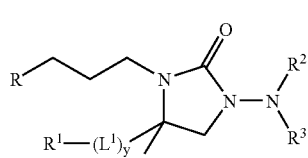

Formula VII

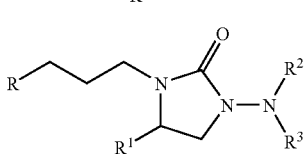

Formula VIII wherein R, R$^1$, R$^{1a}$, R$^2$, and R$^3$ are the same as defined herein.

Compounds of the present invention include compounds having Formula IX, or a pharmaceutically acceptable salt form thereof:

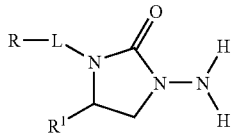

Formula IX wherein $R^2$ and $R^3$ are each hydrogen and non-limiting examples of R, $R^1$ and L are described in Table I and the examples herein below.

TABLE I

| R | $R^1$ | L |
|---|---|---|
| 4-methoxyphenyl | 4-tert-butylphenyl | —CH$_2$CH$_2$— |
| 4-methoxyphenyl | 4-cyclopropylphenyl | —CH$_2$CH$_2$— |
| 4-methoxyphenyl | 3,4-dimethylphenyl | —CH$_2$CH$_2$— |
| 4-methoxyphenyl | 4-methoxyphenyl | —CH$_2$CH$_2$— |
| 4-methoxyphenyl | 4-difluoromethoxyphenyl | —CH$_2$CH$_2$— |
| 4-methoxyphenyl | 4-isopropoxyphenyl | —CH$_2$CH$_2$— |
| 4-methoxyphenyl | 4-(diethylamino)phenyl | —CH$_2$CH$_2$— |
| 4-methoxyphenyl | benzo[1,3]dioxol-5-yl | —CH$_2$CH$_2$— |
| 4-methoxyphenyl | 2,2-difluorobenzo[1,3]-dioxol-5-yl | —CH$_2$CH$_2$— |
| 4-methoxyphenyl | 2,2-dimethylbenzo[1,3]dioxol-5-yl | —CH$_2$CH$_2$— |
| 4-methoxyphenyl | 2,3-dihydro-benzo[1,4]dioxin-6-yl | —CH$_2$CH$_2$— |
| phenyl | 4-tert-butylphenyl | —CH$_2$CH$_2$CH$_2$— |
| phenyl | 4-cyclopropylphenyl | —CH$_2$CH$_2$CH$_2$— |
| phenyl | 3,4-dimethylphenyl | —CH$_2$CH$_2$CH$_2$— |
| phenyl | 4-methoxyphenyl | —CH$_2$CH$_2$CH$_2$— |
| phenyl | 4-difluoromethoxyphenyl | —CH$_2$CH$_2$CH$_2$— |
| phenyl | 4-isopropoxyphenyl | —CH$_2$CH$_2$CH$_2$— |
| phenyl | 4-(diethylamino)phenyl | —CH$_2$CH$_2$CH$_2$— |
| phenyl | benzo[1,3]dioxol-5-yl | —CH$_2$CH$_2$CH$_2$— |
| phenyl | 2,2-difluorobenzo[1,3]-dioxol-5-yl | —CH$_2$CH$_2$CH$_2$— |
| phenyl | 2,2-dimethylbenzo[1,3]dioxol-5-yl | —CH$_2$CH$_2$CH$_2$— |
| phenyl | 2,3-dihydro-benzo[1,4]dioxin-6-yl | —CH$_2$CH$_2$CH$_2$— |

Compounds of the present invention include compounds having formula X, or a pharmaceutically acceptable salt form thereof:

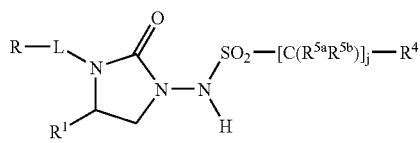

Formula X

Compounds of the present invention include compounds having Formula XI, or a pharmaceutically acceptable salt form thereof:

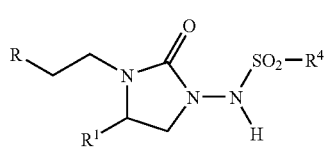

Formula XI wherein non-limiting examples of R, $R^1$, and $R^4$ are defined herein below in Table II.

TABLE II

| R | $R^1$ | $R^4$ |
|---|---|---|
| 4-methoxyphenyl | 3,4-dimethylphenyl | —NH$_2$ |
| 4-methoxyphenyl | 3,4-dimethylphenyl | —CH$_3$ |
| 4-methoxyphenyl | 3,4-dimethylphenyl | —CH$_2$CH$_3$ |
| 4-methoxyphenyl | 3,4-dimethylphenyl | —CH$_2$CH$_2$CH$_3$ |
| 4-methoxyphenyl | 3,4-dimethylphenyl | —CH$_2$CH$_2$CH$_2$CH$_3$ |
| 4-methoxyphenyl | 3,4-dimethylphenyl | —CH$_2$F |
| 4-methoxyphenyl | 3,4-dimethylphenyl | —CHF$_2$ |
| 4-methoxyphenyl | 3,4-dimethylphenyl | —CH$_2$Cl |
| 4-methoxyphenyl | 3,4-dimethylphenyl | —CHCl$_2$ |
| 4-methoxyphenyl | 3,4-dimethylphenyl | —CCl$_3$ |
| 4-methoxyphenyl | 3,4-dimethylphenyl | —CH$_2$CH$_2$F |
| 4-methoxyphenyl | 3,4-dimethylphenyl | —CH$_2$CHF$_2$ |
| 4-methoxyphenyl | 3,4-dimethylphenyl | —CH$_2$CF$_3$ |
| 4-methoxyphenyl | 3,4-dimethylphenyl | -cyclopropyl |
| 4-methoxyphenyl | 3,4-dimethylphenyl | —CH=CH$_2$ |
| 4-methoxyphenyl | 4-tert-butylphenyl | —NH$_2$ |
| 4-methoxyphenyl | 4-tert-butylphenyl | —CH$_3$ |
| 4-methoxyphenyl | 4-tert-butylphenyl | —CH$_2$CH$_3$ |
| 4-methoxyphenyl | 4-tert-butylphenyl | —CH$_2$CH$_2$CH$_3$ |
| 4-methoxyphenyl | 4-tert-butylphenyl | —CH$_2$CH$_2$CH$_2$CH$_3$ |
| 4-methoxyphenyl | 4-tert-butylphenyl | —CH$_2$F |
| 4-methoxyphenyl | 4-tert-butylphenyl | —CHF$_2$ |
| 4-methoxyphenyl | 4-tert-butylphenyl | —CH$_2$Cl |
| 4-methoxyphenyl | 4-tert-butylphenyl | —CHCl$_2$ |
| 4-methoxyphenyl | 4-tert-butylphenyl | —CCl$_3$ |
| 4-methoxyphenyl | 4-tert-butylphenyl | —CH$_2$CH$_2$F |
| 4-methoxyphenyl | 4-tert-butylphenyl | —CH$_2$CHF$_2$ |
| 4-methoxyphenyl | 4-tert-butylphenyl | —CH$_2$CF$_3$ |
| 4-methoxyphenyl | 4-tert-butylphenyl | -cyclopropyl |
| 4-methoxyphenyl | 4-tert-butylphenyl | —CH=CH$_2$ |
| 4-methoxyphenyl | 4-cyclopropylphenyl | —NH$_2$ |
| 4-methoxyphenyl | 4-cyclopropylphenyl | —CH$_3$ |
| 4-methoxyphenyl | 4-cyclopropylphenyl | —CH$_2$CH$_3$ |
| 4-methoxyphenyl | 4-cyclopropylphenyl | —CH$_2$CH$_2$CH$_3$ |
| 4-methoxyphenyl | 4-cyclopropylphenyl | —CH$_2$CH$_2$CH$_2$CH$_3$ |
| 4-methoxyphenyl | 4-cyclopropylphenyl | —CH$_2$F |
| 4-methoxyphenyl | 4-cyclopropylphenyl | —CHF$_2$ |
| 4-methoxyphenyl | 4-cyclopropylphenyl | —CH$_2$Cl |
| 4-methoxyphenyl | 4-cyclopropylphenyl | —CHCl$_2$ |
| 4-methoxyphenyl | 4-cyclopropylphenyl | —CCl$_3$ |
| 4-methoxyphenyl | 4-cyclopropylphenyl | —CH$_2$CH$_2$F |
| 4-methoxyphenyl | 4-cyclopropylphenyl | —CH$_2$CHF$_2$ |
| 4-methoxyphenyl | 4-cyclopropylphenyl | —CH$_2$CF$_3$ |
| 4-methoxyphenyl | 4-cyclopropylphenyl | -cyclopropyl |
| 4-methoxyphenyl | 4-cyclopropylphenyl | —CH=CH$_2$ |
| 4-methoxyphenyl | 4-methoxyphenyl | —NH$_2$ |
| 4-methoxyphenyl | 4-methoxyphenyl | —CH$_3$ |
| 4-methoxyphenyl | 4-methoxyphenyl | —CH$_2$CH$_3$ |
| 4-methoxyphenyl | 4-methoxyphenyl | —CH$_2$CH$_2$CH$_3$ |
| 4-methoxyphenyl | 4-methoxyphenyl | —CH$_2$CH$_2$CH$_2$CH$_3$ |
| 4-methoxyphenyl | 4-methoxyphenyl | —CH$_2$F |
| 4-methoxyphenyl | 4-methoxyphenyl | —CHF$_2$ |
| 4-methoxyphenyl | 4-methoxyphenyl | —CH$_2$Cl |
| 4-methoxyphenyl | 4-methoxyphenyl | —CHCl$_2$ |
| 4-methoxyphenyl | 4-methoxyphenyl | —CCl$_3$ |
| 4-methoxyphenyl | 4-methoxyphenyl | —CH$_2$CH$_2$F |
| 4-methoxyphenyl | 4-methoxyphenyl | —CH$_2$CHF$_2$ |
| 4-methoxyphenyl | 4-methoxyphenyl | —CH$_2$CF$_3$ |
| 4-methoxyphenyl | 4-methoxyphenyl | -cyclopropyl |
| 4-methoxyphenyl | 4-methoxyphenyl | —CH=CH$_2$ |

Compounds of the present invention include compounds having Formula XII, or a pharmaceutically acceptable salt form thereof:

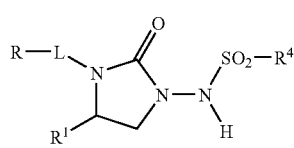

Formula XII

wherein non-limiting examples of R, $R^1$, $R^4$, and L are defined herein below in Table III.

TABLE III

| R | L | $R^1$ | $R^4$ |
|---|---|---|---|
| phenyl | —CH₂CH₂CH₂— | 4-tert-butylphenyl | —NH₂ |
| phenyl | —CH₂CH₂CH₂— | 4-tert-butylphenyl | —CH₃ |
| phenyl | —CH₂CH₂CH₂— | 4-tert-butylphenyl | —CH₂CH₃ |
| phenyl | —CH₂CH₂CH₂— | 4-tert-butylphenyl | —CH₂CH₂CH₃ |
| phenyl | —CH₂CH₂CH₂— | 4-tert-butylphenyl | —CH₂CH₂CH₂CH₃ |
| phenyl | —CH₂CH₂CH₂— | 4-tert-butylphenyl | —CH₂F |
| phenyl | —CH₂CH₂CH₂— | 4-tert-butylphenyl | —CHF₂ |
| phenyl | —CH₂CH₂CH₂— | 4-tert-butylphenyl | —CH₂Cl |
| phenyl | —CH₂CH₂CH₂— | 4-tert-butylphenyl | —CHCl₂ |
| phenyl | —CH₂CH₂CH₂— | 4-tert-butylphenyl | —CCl₃ |
| phenyl | —CH₂CH₂CH₂— | 4-tert-butylphenyl | —CH₂CN |
| phenyl | —CH₂CH₂CH₂— | 4-tert-butylphenyl | —CH₂CH₂F |
| phenyl | —CH₂CH₂CH₂— | 4-tert-butylphenyl | —CH₂CHF₂ |
| phenyl | —CH₂CH₂CH₂— | 4-tert-butylphenyl | —CH₂CF₃ |
| 4-methoxyphenyl | —CH₂CH(CH₃)— | 4-tert-butylphenyl | —NH₂ |
| 4-methoxyphenyl | —CH₂CH(CH₃)— | 4-tert-butylphenyl | —CH₃ |
| 4-methoxyphenyl | —CH₂CH(CH₃)— | 4-tert-butylphenyl | —CH₂CH₃ |
| 4-methoxyphenyl | —CH₂CH(CH₃)— | 4-tert-butylphenyl | —CH₂CH₂CH₃ |
| 4-methoxyphenyl | —CH₂CH(CH₃)— | 4-tert-butylphenyl | —CH₂CH₂CH₂CH₃ |
| 4-methoxyphenyl | —CH₂CH(CH₃)— | 4-tert-butylphenyl | —CH₂F |
| 4-methoxyphenyl | —CH₂CH(CH₃)— | 4-tert-butylphenyl | —CHF₂ |
| 4-methoxyphenyl | —CH₂CH(CH₃)— | 4-tert-butylphenyl | —CF₃ |
| 4-methoxyphenyl | —CH₂CH(CH₃)— | 4-tert-butylphenyl | —CH₂Cl |
| 4-methoxyphenyl | —CH₂CH(CH₃)— | 4-tert-butylphenyl | —CHCl₂ |
| 4-methoxyphenyl | —CH₂CH(CH₃)— | 4-tert-butylphenyl | —CCl₃ |
| 4-methoxyphenyl | —CH₂CH(CH₃)— | 4-tert-butylphenyl | —CH₂CN |
| 4-methoxyphenyl | —CH₂CH(CH₃)— | 4-tert-butylphenyl | —CH₂CH₂F |
| 4-methoxyphenyl | —CH₂CH(CH₃)— | 4-tert-butylphenyl | —CH₂CHF₂ |
| 4-methoxyphenyl | —CH₂CH(CH₃)— | 4-tert-butylphenyl | —CH₂CF₃ |

Compounds of the present invention include compounds having Formula XIII, or a pharmaceutically acceptable salt form thereof:

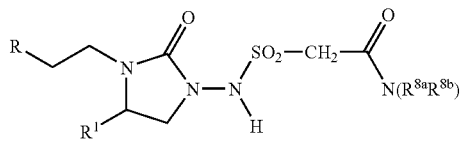

Formula XIII wherein non-limiting examples of R, $R^1$, and $R^4$ are defined herein below in Table IV.

TABLE IV

| R | $R^1$ | $N(R^{8a}R^{8b})$ |
|---|---|---|
| 4-methoxyphenyl | 4-tert-butylphenyl | —NH₂ |
| 4-methoxyphenyl | 4-cyclopropylphenyl | —NH₂ |
| 4-methoxyphenyl | 3,4-dimethylphenyl | —NH₂ |
| 4-methoxyphenyl | 4-methoxyphenyl | —NH₂ |
| 4-methoxyphenyl | 4-difluoromethylphenyl | —NH₂ |
| 4-methoxyphenyl | 4-isopropoxyphenyl | —NH₂ |
| 4-methoxyphenyl | 4-(diethylamino)phenyl | —NH₂ |
| 4-methoxyphenyl | benzo[1,3]dioxol-5-yl | —NH₂ |
| 4-methoxyphenyl | 2,2-difluorobenzo[1,3]-dioxol-5-yl | —NH₂ |
| 4-methoxyphenyl | 2,2-dimethylbenzo[1,3]dioxol-5-yl | —NH₂ |
| 4-methoxyphenyl | 2,3-dihydro-benzo[1,4]dioxin-6-yl | —NH₂ |
| phenyl | 4-tert-butylphenyl | —NHCH₃ |
| phenyl | 4-cyclopropylphenyl | —NHCH₃ |
| phenyl | 3,4-dimethylphenyl | —NHCH₃ |
| phenyl | 4-methoxyphenyl | —NHCH₃ |
| phenyl | 4-difluoromethylphenyl | —NHCH₃ |
| phenyl | 4-isopropoxyphenyl | —NHCH₃ |
| phenyl | 4-(diethylamino)phenyl | —NHCH₃ |
| phenyl | benzo[1,3]dioxol-5-yl | —NHCH₃ |
| phenyl | 2,2-difluorobenzo[1,3]-dioxol-5-yl | —NHCH₃ |
| phenyl | 2,2-dimethylbenzo[1,3]dioxol-5-yl | —NHCH₃ |
| phenyl | 2,3-dihydro-benzo[1,4]dioxin-6-yl | —NHCH₃ |
| 4-methoxyphenyl | 4-tert-butylphenyl | —N(CH₃)₂ |
| 4-methoxyphenyl | 4-cyclopropylphenyl | —N(CH₃)₂ |
| 4-methoxyphenyl | 3,4-dimethylphenyl | —N(CH₃)₂ |
| 4-methoxyphenyl | 4-methoxyphenyl | —N(CH₃)₂ |
| 4-methoxyphenyl | 4-difluoromethylphenyl | —N(CH₃)₂ |
| 4-methoxyphenyl | 4-isopropoxyphenyl | —N(CH₃)₂ |
| 4-methoxyphenyl | 4-(diethylamino)phenyl | —N(CH₃)₂ |
| 4-methoxyphenyl | benzo[1,3]dioxol-5-yl | —N(CH₃)₂ |
| 4-methoxyphenyl | 2,2-difluorobenzo[1,3]-dioxol-5-yl | —N(CH₃)₂ |
| 4-methoxyphenyl | 2,2-dimethylbenzo[1,3]dioxol-5-yl | —N(CH₃)₂ |
| 4-methoxyphenyl | 2,3-dihydro-benzo[1,4]dioxin-6-yl | —N(CH₃)₂ |
| 4-methoxyphenyl | 4-tert-butylphenyl | —NH(cyclopropyl) |
| 4-methoxyphenyl | 4-cyclopropylphenyl | —NH(cyclopropyl) |
| 4-methoxyphenyl | 3,4-dimethylphenyl | —NH(cyclopropyl) |
| 4-methoxyphenyl | 4-methoxyphenyl | —NH(cyclopropyl) |
| 4-methoxyphenyl | 4-difluoromethylphenyl | —NH(cyclopropyl) |
| 4-methoxyphenyl | 4-isopropoxyphenyl | —NH(cyclopropyl) |
| 4-methoxyphenyl | 4-(diethylamino)phenyl | —NH(cyclopropyl) |
| 4-methoxyphenyl | benzo[1,3]dioxol-5-yl | —NH(cyclopropyl) |

TABLE IV-continued

| R | R$^1$ | N(R$^{8a}$R$^{8b}$) |
|---|---|---|
| 4-methoxyphenyl | 2,2-difluorobenzo[1,3]-dioxol-5-yl | —NH(cyclopropyl) |
| 4-methoxyphenyl | 2,2-dimethylbenzo[1,3]dioxol-5-yl | —NH(cyclopropyl) |
| 4-methoxyphenyl | 2,3-dihydro-benzo[1,4]dioxin-6-yl | —NH(cyclopropyl) |
| 4-methoxyphenyl | 4-tert-butylphenyl | —NHCH$_2$(cyclopropyl) |
| 4-methoxyphenyl | 4-cyclopropylphenyl | —NHCH$_2$(cyclopropyl) |
| 4-methoxyphenyl | 3,4-dimethylphenyl | —NHCH$_2$(cyclopropyl) |
| 4-methoxyphenyl | 4-methoxyphenyl | —NHCH$_2$(cyclopropyl) |
| 4-methoxyphenyl | 4-difluoromethylphenyl | —NHCH$_2$(cyclopropyl) |
| 4-methoxyphenyl | 4-isopropoxyphenyl | —NHCH$_2$(cyclopropyl) |
| 4-methoxyphenyl | 4-(diethylamino)phenyl | —NHCH$_2$(cyclopropyl) |
| 4-methoxyphenyl | benzo[1,3]dioxol-5-yl | —NHCH$_2$(cyclopropyl) |
| 4-methoxyphenyl | 2,2-difluorobenzo[1,3]-dioxol-5-yl | —NHCH$_2$(cyclopropyl) |
| 4-methoxyphenyl | 2,2-dimethylbenzo[1,3]dioxol-5-yl | —NHCH$_2$(cyclopropyl) |
| 4-methoxyphenyl | 2,3-dihydro-benzo[1,4]dioxin-6-yl | —NHCH$_2$(cyclopropyl) |

Compounds of the present invention include compounds having Formula XIV, or a pharmaceutically acceptable salt form thereof:

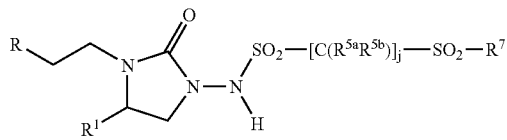

Formula XIV wherein non-limiting examples of R, R$^1$, R$^{5a}$, R$^{5b}$, and R$^7$ are defined herein below in Table V.

TABLE V

| R | R$^1$ | C(R$^{5a}$R$^{5b}$)$_j$ | R$^7$ |
|---|---|---|---|
| 4-methoxyphenyl | 3,4-dimethylphenyl | —CH$_2$— | —CH$_3$ |
| 4-methoxyphenyl | 3,4-dimethylphenyl | —CH$_2$— | —CH$_2$CH$_3$ |
| 4-methoxyphenyl | 3,4-dimethylphenyl | —CH$_2$— | —CH$_2$CH$_2$CH$_3$ |
| 4-methoxyphenyl | 3,4-dimethylphenyl | —CH$_2$— | —CH$_2$CH$_2$CH$_2$CH$_3$ |
| 4-methoxyphenyl | 3,4-dimethylphenyl | —CH$_2$CH$_2$— | —CH$_3$ |
| 4-methoxyphenyl | 3,4-dimethylphenyl | —CH$_2$CH$_2$— | —CH$_2$CH$_3$ |
| 4-methoxyphenyl | 3,4-dimethylphenyl | —CH$_2$CH$_2$— | —CH$_2$CH$_2$CH$_3$ |
| 4-methoxyphenyl | 3,4-dimethylphenyl | —CH$_2$CH$_2$— | —CH$_2$CH$_2$CH$_2$CH$_3$ |
| 4-methoxyphenyl | 4-tert-butylphenyl | —CH$_2$— | —CH$_3$ |
| 4-methoxyphenyl | 4-tert-butylphenyl | —CH$_2$— | —CH$_2$CH$_3$ |
| 4-methoxyphenyl | 4-tert-butylphenyl | —CH$_2$— | —CH$_2$CH$_2$CH$_3$ |
| 4-methoxyphenyl | 4-tert-butylphenyl | —CH$_2$— | —CH$_2$CH$_2$CH$_2$CH$_3$ |
| 4-methoxyphenyl | 4-tert-butylphenyl | —CH$_2$CH$_2$— | —CH$_3$ |
| 4-methoxyphenyl | 4-tert-butylphenyl | —CH$_2$CH$_2$— | —CH$_2$CH$_3$ |
| 4-methoxyphenyl | 4-tert-butylphenyl | —CH$_2$CH$_2$— | —CH$_2$CH$_2$CH$_3$ |
| 4-methoxyphenyl | 4-tert-butylphenyl | —CH$_2$CH$_2$— | —CH$_2$CH$_2$CH$_2$CH$_3$ |
| 4-methoxyphenyl | 4-cyclopropylphenyl | —CH$_2$— | —CH$_3$ |
| 4-methoxyphenyl | 4-cyclopropylphenyl | —CH$_2$— | —CH$_2$CH$_3$ |
| 4-methoxyphenyl | 4-cyclopropylphenyl | —CH$_2$— | —CH$_2$CH$_2$CH$_3$ |
| 4-methoxyphenyl | 4-cyclopropylphenyl | —CH$_2$— | —CH$_2$CH$_2$CH$_2$CH$_3$ |
| 4-methoxyphenyl | 4-cyclopropylphenyl | —CH$_2$CH$_2$— | —CH$_3$ |
| 4-methoxyphenyl | 4-cyclopropylphenyl | —CH$_2$CH$_2$— | —CH$_2$CH$_3$ |
| 4-methoxyphenyl | 4-cyclopropylphenyl | —CH$_2$CH$_2$— | —CH$_2$CH$_2$CH$_3$ |
| 4-methoxyphenyl | 4-cyclopropylphenyl | —CH$_2$CH$_2$— | —CH$_2$CH$_2$CH$_2$CH$_3$ |
| 4-methoxyphenyl | 4-methoxyphenyl | —CH$_2$— | —CH$_3$ |
| 4-methoxyphenyl | 4-methoxyphenyl | —CH$_2$— | —CH$_2$CH$_3$ |
| 4-methoxyphenyl | 4-methoxyphenyl | —CH$_2$— | —CH$_2$CH$_2$CH$_3$ |
| 4-methoxyphenyl | 4-methoxyphenyl | —CH$_2$— | —CH$_2$CH$_2$CH$_2$CH$_3$ |
| 4-methoxyphenyl | 4-methoxyphenyl | —CH$_2$CH$_2$— | —CH$_3$ |
| 4-methoxyphenyl | 4-methoxyphenyl | —CH$_2$CH$_2$— | —CH$_2$CH$_3$ |
| 4-methoxyphenyl | 4-methoxyphenyl | —CH$_2$CH$_2$— | —CH$_2$CH$_2$CH$_3$ |
| 4-methoxyphenyl | 4-methoxyphenyl | —CH$_2$CH$_2$— | —CH$_2$CH$_2$CH$_2$CH$_3$ |

Compounds of the present invention include compounds having Formula XV, or a pharmaceutically acceptable salt form thereof:

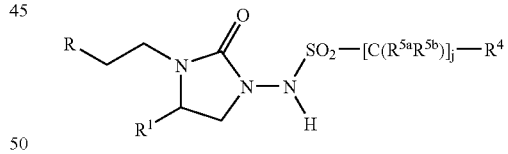

Formula XV wherein non-limiting examples of R, R$^1$, R$^{5a}$, R$^{5b}$, and R$^4$ are defined herein below in Table VI.

TABLE VI

| R | R$^1$ | C(R$^{5a}$R$^{5b}$)$_j$ | R$^4$ |
|---|---|---|---|
| 4-methoxyphenyl | 3,4-dimethylphenyl | — | -(pyridin-2-yl) |
| 4-methoxyphenyl | 3,4-dimethylphenyl | — | -(pyridin-3-yl) |
| 4-methoxyphenyl | 3,4-dimethylphenyl | — | -(pyridin-4-yl) |
| 4-methoxyphenyl | 3,4-dimethylphenyl | — | —C$_6$H$_5$ |
| 4-methoxyphenyl | 3,4-dimethylphenyl | —CH$_2$— | -(pyridin-2-yl) |
| 4-methoxyphenyl | 3,4-dimethylphenyl | —CH$_2$— | -(pyridin-3-yl) |
| 4-methoxyphenyl | 3,4-dimethylphenyl | —CH$_2$— | -(pyridin-4-yl) |
| 4-methoxyphenyl | 3,4-dimethylphenyl | —CH$_2$— | —C$_6$H$_5$ |
| 4-methoxyphenyl | 4-tert-butylphenyl | — | -(pyridin-2-yl) |
| 4-methoxyphenyl | 4-tert-butylphenyl | — | -(pyridin-3-yl) |

TABLE VI-continued

| R | R¹ | C(R⁵ᵃR⁵ᵇ)ⱼ | R⁴ |
|---|---|---|---|
| 4-methoxyphenyl | 4-tert-butylphenyl | — | -(pyridin-4-yl) |
| 4-methoxyphenyl | 4-tert-butylphenyl | — | —C₆H₅ |
| 4-methoxyphenyl | 4-tert-butylphenyl | —CH₂— | -(pyridin-2-yl) |
| 4-methoxyphenyl | 4-tert-butylphenyl | —CH₂— | -(pyridin-3-yl) |
| 4-methoxyphenyl | 4-tert-butylphenyl | —CH₂— | -(pyridin-4-yl) |
| 4-methoxyphenyl | 4-tert-butylphenyl | —CH₂— | —C₆H₅ |
| 4-methoxyphenyl | 4-cyclopropylphenyl | — | -(pyridin-2-yl) |
| 4-methoxyphenyl | 4-cyclopropylphenyl | — | -(pyridin-3-yl) |
| 4-methoxyphenyl | 4-cyclopropylphenyl | — | -(pyridin-4-yl) |
| 4-methoxyphenyl | 4-cyclopropylphenyl | — | —C₆H₅ |
| 4-methoxyphenyl | 4-cyclopropylphenyl | —CH₂— | -(pyridin-2-yl) |
| 4-methoxyphenyl | 4-cyclopropylphenyl | —CH₂— | -(pyridin-3-yl) |
| 4-methoxyphenyl | 4-cyclopropylphenyl | —CH₂— | -(pyridin-4-yl) |
| 4-methoxyphenyl | 4-cyclopropylphenyl | —CH₂— | —C₆H₅ |
| 4-methoxyphenyl | 4-methoxyphenyl | — | -(pyridin-2-yl) |
| 4-methoxyphenyl | 4-methoxyphenyl | — | -(pyridin-3-yl) |
| 4-methoxyphenyl | 4-methoxyphenyl | — | -(pyridin-4-yl) |
| 4-methoxyphenyl | 4-methoxyphenyl | — | —C₆H₅ |
| 4-methoxyphenyl | 4-methoxyphenyl | —CH₂— | -(pyridin-2-yl) |
| 4-methoxyphenyl | 4-methoxyphenyl | —CH₂— | -(pyridin-3-yl) |
| 4-methoxyphenyl | 4-methoxyphenyl | —CH₂— | -(pyridin-4-yl) |
| 4-methoxyphenyl | 4-methoxyphenyl | —CH₂— | —C₆H₅ |

Compounds of the present invention include compounds having Formula XVI, or a pharmaceutically acceptable salt form thereof:

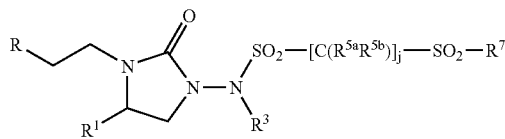

Formula XVI wherein non-limiting examples of R, R¹, R⁵ᵃ, R⁵ᵇ, and R⁷ are defined herein below in Table VII.

TABLE VII

| R | R¹ | R³ | C(R⁵ᵃR⁵ᵇ)ⱼ | R⁷ |
|---|---|---|---|---|
| 4-methoxyphenyl | 3,4-dimethylphenyl | —CH₃ | —CH₂— | —CH₃ |
| 4-methoxyphenyl | 3,4-dimethylphenyl | —CH₃ | —CH₂— | —CH₂CH₃ |
| 4-methoxyphenyl | 3,4-dimethylphenyl | —CH₃ | —CH₂— | -cyclopropyl |
| 4-methoxyphenyl | 3,4-dimethylphenyl | —CH₃ | —CH₂CH₂— | —CH₃ |
| 4-methoxyphenyl | 3,4-dimethylphenyl | —CH₃ | —CH₂CH₂— | —CH₂CH₃ |
| 4-methoxyphenyl | 3,4-dimethylphenyl | —CH₃ | —CH₂CH₂— | -cyclopropyl |
| 4-methoxyphenyl | 4-tert-butylphenyl | —CH₃ | —CH₂— | —CH₃ |
| 4-methoxyphenyl | 4-tert-butylphenyl | —CH₃ | —CH₂— | —CH₂CH₃ |
| 4-methoxyphenyl | 4-tert-butylphenyl | —CH₃ | —CH₂— | -cyclopropyl |
| 4-methoxyphenyl | 4-tert-butylphenyl | —CH₃ | —CH₂CH₂— | —CH₃ |
| 4-methoxyphenyl | 4-tert-butylphenyl | —CH₃ | —CH₂CH₂— | —CH₂CH₃ |
| 4-methoxyphenyl | 4-tert-butylphenyl | —CH₃ | —CH₂CH₂— | -cyclopropyl |
| 4-methoxyphenyl | 4-cyclopropylphenyl | —CH₃ | —CH₂— | —CH₃ |
| 4-methoxyphenyl | 4-cyclopropylphenyl | —CH₃ | —CH₂— | —CH₂CH₃ |
| 4-methoxyphenyl | 4-cyclopropylphenyl | —CH₃ | —CH₂— | -cyclopropyl |
| 4-methoxyphenyl | 4-cyclopropylphenyl | —CH₃ | —CH₂CH₂— | —CH₃ |
| 4-methoxyphenyl | 4-cyclopropylphenyl | —CH₃ | —CH₂CH₂— | —CH₂CH₃ |
| 4-methoxyphenyl | 4-cyclopropylphenyl | —CH₃ | —CH₂CH₂— | -cyclopropyl |
| 4-methoxyphenyl | 4-methoxyphenyl | —CH₃ | —CH₂— | —CH₃ |
| 4-methoxyphenyl | 4-methoxyphenyl | —CH₃ | —CH₂— | —CH₂CH₃ |
| 4-methoxyphenyl | 4-methoxyphenyl | —CH₃ | —CH₂— | -cyclopropyl |
| 4-methoxyphenyl | 4-methoxyphenyl | —CH₃ | —CH₂CH₂— | —CH₃ |
| 4-methoxyphenyl | 4-methoxyphenyl | —CH₃ | —CH₂CH₂— | —CH₂CH₃ |
| 4-methoxyphenyl | 4-methoxyphenyl | —CH₃ | —CH₂CH₂— | -cyclopropyl |

Compounds of the present invention include compounds having Formula XVII, or a pharmaceutically acceptable salt form thereof:

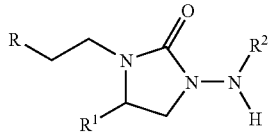

Formula XVII wherein non-limiting examples of R, R¹, and R² are defined herein below in Table VIII.

TABLE VIII

| R | R¹ | R² |
|---|---|---|
| 4-methoxyphenyl | 3,4-dimethylphenyl | —C(O)CH₃ |
| 4-methoxyphenyl | 3,4-dimethylphenyl | —C(O)OCH₃ |
| 4-methoxyphenyl | 3,4-dimethylphenyl | —C(O)(cyclopropyl) |
| 4-methoxyphenyl | 3,4-dimethylphenyl | —C(O)OC(CH₃)₃ |
| 4-methoxyphenyl | 3,4-dimethylphenyl | —C(O)CH₂N(CH₃)benzyl |
| 4-methoxyphenyl | 3,4-dimethylphenyl | —C(O)CH₂N(CH₃)Boc |
| 4-methoxyphenyl | 3,4-dimethylphenyl | —C(O)furan-2-yl |

TABLE VIII-continued

| R | $R^1$ | $R^2$ |
|---|---|---|
| 4-methoxyphenyl | 3,4-dimethylphenyl | —C(O)C$_6$H$_5$ |
| 4-methoxyphenyl | 3,4-dimethylphenyl | —C(O)CH$_2$C$_6$H$_5$ |
| 4-methoxyphenyl | 3,4-dimethylphenyl | —C(O)CH$_2$OC$_6$H$_5$ |
| 4-methoxyphenyl | 3,4-dimethylphenyl | —C(O)isoxazol-5-yl |
| 4-methoxyphenyl | 3,4-dimethylphenyl | —C(O)pyrazin-2-yl |
| 4-methoxyphenyl | 4-tert-butylphenyl | —C(O)CH$_3$ |
| 4-methoxyphenyl | 4-tert-butylphenyl | —C(O)OCH$_3$ |
| 4-methoxyphenyl | 4-tert-butylphenyl | —C(O)(cyclopropyl) |
| 4-methoxyphenyl | 4-tert-butylphenyl | —C(O)OC(CH$_3$)$_3$ |
| 4-methoxyphenyl | 4-tert-butylphenyl | —C(O)CH$_2$N(CH$_3$)benzyl |
| 4-methoxyphenyl | 4-tert-butylphenyl | —C(O)CH$_2$N(CH$_3$)Boc |
| 4-methoxyphenyl | 4-tert-butylphenyl | —C(O)furan-2-yl |
| 4-methoxyphenyl | 4-tert-butylphenyl | —C(O)C$_6$H$_5$ |
| 4-methoxyphenyl | 4-tert-butylphenyl | —C(O)CH$_2$C$_6$H$_5$ |
| 4-methoxyphenyl | 4-tert-butylphenyl | —C(O)CH$_2$OC$_6$H$_5$ |
| 4-methoxyphenyl | 4-tert-butylphenyl | —C(O)isoxazol-5-yl |
| 4-methoxyphenyl | 4-tert-butylphenyl | —C(O)pyrazin-2-yl |
| 4-methoxyphenyl | 4-cyclopropylphenyl | —C(O)CH$_3$ |
| 4-methoxyphenyl | 4-cyclopropylphenyl | —C(O)OCH$_3$ |
| 4-methoxyphenyl | 4-cyclopropylphenyl | —C(O)(cyclopropyl) |
| 4-methoxyphenyl | 4-cyclopropylphenyl | —C(O)OC(CH$_3$)$_3$ |
| 4-methoxyphenyl | 4-cyclopropylphenyl | —C(O)CH$_2$N(CH$_3$)benzyl |
| 4-methoxyphenyl | 4-cyclopropylphenyl | —C(O)CH$_2$N(CH$_3$)Boc |
| 4-methoxyphenyl | 4-cyclopropylphenyl | —C(O)furan-2-yl |
| 4-methoxyphenyl | 4-cyclopropylphenyl | —C(O)C$_6$H$_5$ |
| 4-methoxyphenyl | 4-cyclopropylphenyl | —C(O)CH$_2$C$_6$H$_5$ |
| 4-methoxyphenyl | 4-cyclopropylphenyl | —C(O)CH$_2$OC$_6$H$_5$ |
| 4-methoxyphenyl | 4-cyclopropylphenyl | —C(O)isoxazol-5-yl |
| 4-methoxyphenyl | 4-cyclopropylphenyl | —C(O)pyrazin-2-yl |
| 4-methoxyphenyl | 4-(CHF$_2$O)phenyl | —C(O)CH$_3$ |
| 4-methoxyphenyl | 4-(CHF$_2$O)phenyl | —C(O)OCH$_3$ |
| 4-methoxyphenyl | 4-(CHF$_2$O)phenyl | —C(O)(cyclopropyl) |
| 4-methoxyphenyl | 4-(CHF$_2$O)phenyl | —C(O)OC(CH$_3$)$_3$ |
| 4-methoxyphenyl | 4-(CHF$_2$O)phenyl | —C(O)CH$_2$N(CH$_3$)benzyl |
| 4-methoxyphenyl | 4-(CHF$_2$O)phenyl | —C(O)CH$_2$N(CH$_3$)Boc |
| 4-methoxyphenyl | 4-(CHF$_2$O)phenyl | —C(O)furan-2-yl |
| 4-methoxyphenyl | 4-(CHF$_2$O)phenyl | —C(O)C$_6$H$_5$ |
| 4-methoxyphenyl | 4-(CHF$_2$O)phenyl | —C(O)CH$_2$C$_6$H$_5$ |
| 4-methoxyphenyl | 4-(CHF$_2$O)phenyl | —C(O)CH$_2$OC$_6$H$_5$ |
| 4-methoxyphenyl | 4-(CHF$_2$O)phenyl | —C(O)isoxazol-5-yl |
| 4-methoxyphenyl | 4-(CHF$_2$O)phenyl | —C(O)pyrazin-2-yl |
| 4-methoxyphenyl | 4-(CH$_3$O)phenyl | —C(O)CH$_3$ |
| 4-methoxyphenyl | 4-(CH$_3$O)phenyl | —C(O)OCH$_3$ |
| 4-methoxyphenyl | 4-(CH$_3$O)phenyl | —C(O)(cyclopropyl) |
| 4-methoxyphenyl | 4-(CH$_3$O)phenyl | —C(O)OC(CH$_3$)$_3$ |
| 4-methoxyphenyl | 4-(CH$_3$O)phenyl | —C(O)CH$_2$N(CH$_3$)benzyl |
| 4-methoxyphenyl | 4-(CH$_3$O)phenyl | —C(O)CH$_2$N(CH$_3$)Boc |
| 4-methoxyphenyl | 4-(CH$_3$O)phenyl | —C(O)furan-2-yl |
| 4-methoxyphenyl | 4-(CH$_3$O)phenyl | —C(O)C$_6$H$_5$ |
| 4-methoxyphenyl | 4-(CH$_3$O)phenyl | —C(O)CH$_2$C$_6$H$_5$ |
| 4-methoxyphenyl | 4-(CH$_3$O)phenyl | —C(O)CH$_2$OC$_6$H$_5$ |
| 4-methoxyphenyl | 4-(CH$_3$O)phenyl | —C(O)isoxazol-5-yl |
| 4-methoxyphenyl | 4-(CH$_3$O)phenyl | —C(O)pyrazin-2-yl |

Compounds of the present invention include compounds having Formula XVII, or a pharmaceutically acceptable salt form thereof:

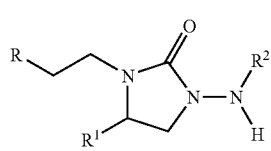

Formula XVII wherein non-limiting examples of R, $R^1$, and $R^2$ are defined herein below in Table IX.

TABLE IX

| R | $R^1$ | $R^2$ |
|---|---|---|
| 4-methoxyphenyl | 3,4-dimethylphenyl | —CH$_2$(cyclopropyl) |
| 4-methoxyphenyl | 3,4-dimethylphenyl | —CH$_2$C$_6$H$_5$ |
| 4-methoxyphenyl | 3,4-dimethylphenyl | —CH$_2$CH$_2$C$_6$H$_5$ |
| 4-methoxyphenyl | 3,4-dimethylphenyl | —CH$_2$C$_6$H$_4$(4-CN) |
| 4-methoxyphenyl | 3,4-dimethylphenyl | —CH$_2$C$_6$H$_4$(4-F) |
| 4-methoxyphenyl | 3,4-dimethylphenyl | —CH$_2$C$_6$H$_4$[4-N(CH$_3$)$_2$] |
| 4-methoxyphenyl | 3,4-dimethylphenyl | —CH$_2$C$_6$H$_4$[4-N(C$_2$H$_5$)$_2$] |
| 4-methoxyphenyl | 3,4-dimethylphenyl | —CH$_2$C$_6$H$_4$(4-imidazolyl) |
| 4-methoxyphenyl | 3,4-dimethylphenyl | —CH$_2$(imidazol-1-yl) |
| 4-methoxyphenyl | 3,4-dimethylphenyl | —CH$_2$(pyridine-2-yl) |
| 4-methoxyphenyl | 3,4-dimethylphenyl | —CH$_2$(pyridine-3-yl) |
| 4-methoxyphenyl | 3,4-dimethylphenyl | —CH$_2$(pyridine-4-yl) |
| 4-methoxyphenyl | 4-tert-butylphenyl | —CH$_2$(cyclopropyl) |
| 4-methoxyphenyl | 4-tert-butylphenyl | —CH$_2$C$_6$H$_5$ |
| 4-methoxyphenyl | 4-tert-butylphenyl | —CH$_2$CH$_2$C$_6$H$_5$ |
| 4-methoxyphenyl | 4-tert-butylphenyl | —CH$_2$C$_6$H$_4$(4-CN) |
| 4-methoxyphenyl | 4-tert-butylphenyl | —CH$_2$C$_6$H$_4$(4-F) |
| 4-methoxyphenyl | 4-tert-butylphenyl | —CH$_2$C$_6$H$_4$[4-N(CH$_3$)$_2$] |
| 4-methoxyphenyl | 4-tert-butylphenyl | —CH$_2$C$_6$H$_4$[4-N(C$_2$H$_5$)$_2$] |
| 4-methoxyphenyl | 4-tert-butylphenyl | —CH$_2$C$_6$H$_4$(4-imidazolyl) |
| 4-methoxyphenyl | 4-tert-butylphenyl | —CH$_2$(imidazol-1-yl) |
| 4-methoxyphenyl | 4-tert-butylphenyl | —CH$_2$(pyridine-2-yl) |
| 4-methoxyphenyl | 4-tert-butylphenyl | —CH$_2$(pyridine-3-yl) |
| 4-methoxyphenyl | 4-tert-butylphenyl | —CH$_2$(pyridine-4-yl) |
| 4-methoxyphenyl | 4-cyclopropylphenyl | —CH$_2$(cyclopropyl) |
| 4-methoxyphenyl | 4-cyclopropylphenyl | —CH$_2$C$_6$H$_5$ |
| 4-methoxyphenyl | 4-cyclopropylphenyl | —CH$_2$CH$_2$C$_6$H$_5$ |
| 4-methoxyphenyl | 4-cyclopropylphenyl | —CH$_2$C$_6$H$_4$(4-CN) |
| 4-methoxyphenyl | 4-cyclopropylphenyl | —CH$_2$C$_6$H$_4$(4-F) |
| 4-methoxyphenyl | 4-cyclopropylphenyl | —CH$_2$C$_6$H$_4$[4-N(CH$_3$)$_2$] |
| 4-methoxyphenyl | 4-cyclopropylphenyl | —CH$_2$C$_6$H$_4$[4-N(C$_2$H$_5$)$_2$] |
| 4-methoxyphenyl | 4-cyclopropylphenyl | —CH$_2$C$_6$H$_4$(4-imidazolyl) |
| 4-methoxyphenyl | 4-cyclopropylphenyl | —CH$_2$(imidazol-1-yl) |
| 4-methoxyphenyl | 4-cyclopropylphenyl | —CH$_2$(pyridine-2-yl) |
| 4-methoxyphenyl | 4-cyclopropylphenyl | —CH$_2$(pyridine-3-yl) |
| 4-methoxyphenyl | 4-cyclopropylphenyl | —CH$_2$(pyridine-4-yl) |
| 4-methoxyphenyl | 4-(CHF$_2$O)phenyl | —CH$_2$(cyclopropyl) |
| 4-methoxyphenyl | 4-(CHF$_2$O)phenyl | —CH$_2$C$_6$H$_5$ |
| 4-methoxyphenyl | 4-(CHF$_2$O)phenyl | —CH$_2$CH$_2$C$_6$H$_5$ |
| 4-methoxyphenyl | 4-(CHF$_2$O)phenyl | —CH$_2$C$_6$H$_4$(4-CN) |
| 4-methoxyphenyl | 4-(CHF$_2$O)phenyl | —CH$_2$C$_6$H$_4$(4-F) |
| 4-methoxyphenyl | 4-(CHF$_2$O)phenyl | —CH$_2$C$_6$H$_4$[4-N(CH$_3$)$_2$] |
| 4-methoxyphenyl | 4-(CHF$_2$O)phenyl | —CH$_2$C$_6$H$_4$[4-N(C$_2$H$_5$)$_2$] |
| 4-methoxyphenyl | 4-(CHF$_2$O)phenyl | —CH$_2$C$_6$H$_4$(4-imidazolyl) |
| 4-methoxyphenyl | 4-(CHF$_2$O)phenyl | —CH$_2$(imidazol-1-yl) |
| 4-methoxyphenyl | 4-(CHF$_2$O)phenyl | —CH$_2$(pyridine-2-yl) |
| 4-methoxyphenyl | 4-(CHF$_2$O)phenyl | —CH$_2$(pyridine-3-yl) |
| 4-methoxyphenyl | 4-(CHF$_2$O)phenyl | —CH$_2$(pyridine-4-yl) |
| 4-methoxyphenyl | 4-(CH$_3$O)phenyl | —CH$_2$(cyclopropyl) |
| 4-methoxyphenyl | 4-(CH$_3$O)phenyl | —CH$_2$C$_6$H$_5$ |
| 4-methoxyphenyl | 4-(CH$_3$O)phenyl | —CH$_2$CH$_2$C$_6$H$_5$ |
| 4-methoxyphenyl | 4-(CH$_3$O)phenyl | —CH$_2$C$_6$H$_4$(4-CN) |
| 4-methoxyphenyl | 4-(CH$_3$O)phenyl | —CH$_2$C$_6$H$_4$(4-F) |
| 4-methoxyphenyl | 4-(CH$_3$O)phenyl | —CH$_2$C$_6$H$_4$[4-N(CH$_3$)$_2$] |
| 4-methoxyphenyl | 4-(CH$_3$O)phenyl | —CH$_2$C$_6$H$_4$[4-N(C$_2$H$_5$)$_2$] |
| 4-methoxyphenyl | 4-(CH$_3$O)phenyl | —CH$_2$C$_6$H$_4$(4-imidazolyl) |
| 4-methoxyphenyl | 4-(CH$_3$O)phenyl | —CH$_2$(imidazol-1-yl) |
| 4-methoxyphenyl | 4-(CH$_3$O)phenyl | —CH$_2$(pyridine-2-yl) |
| 4-methoxyphenyl | 4-(CH$_3$O)phenyl | —CH$_2$(pyridine-3-yl) |
| 4-methoxyphenyl | 4-(CH$_3$O)phenyl | —CH$_2$(pyridine-4-yl) |

Compounds of the present invention include compounds having Formula XVIII or XIX, or a pharmaceutically acceptable salt form thereof:

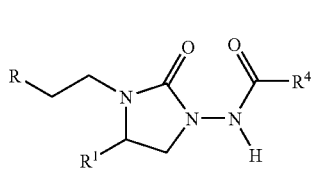

Formula (XVIII)

Formula (XIX)

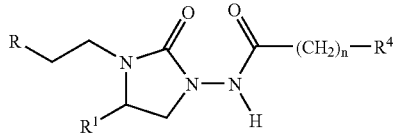

wherein R, R¹, n, and R⁴ are defined herein.

Exemplary compounds of Formula IX can be prepared by the procedures outlined in Example 1 below. The skilled practitioner will know how to substitute the appropriate reagents, starting materials and purification methods known to those skilled in the art, in order to prepare additional compounds of the present invention.

EXAMPLE 1

Compound 1: 1-Amino-3-[2-(4-methoxyphenyl)ethyl]-4-(3,4-dimethylphenyl)-2-imidazolidinone Step A: Preparation of 3,4-dimethyl-[(1E)-2-nitroethenyl]benzene: A solution of 3,4-dimethylbenzaldehyde (20 mL, 0.15 mol), ammonium acetate (12.5 g, 0.16 mol), glacial acetic acid (65 mL), nitromethane (34 mL, 0.63 mol), and acetic anhydride (3.0 mL, 0.032 mol) is refluxed for 2 hours. The reaction is concentrated to an oil, then dichloromethane (100 mL) is added, and the solution is washed with water (2×) and brine. The organic phase is dried (MgSO₄), and concentrated to a dark green solid. This material is re-crystallized (treated with Darco) from 50% cyclohexane/hexanes to afford 17.6 g (66% yield) of the desired compound. ¹H NMR (CDCl₃) δ 8.08 (dd, J=2.4 Hz, 13.5 Hz, 1H), 7.61 (dd, J=2.4 Hz, 13.5 Hz, 1H), 7.31-7.36 (m, 2H), 7.25 (d, J=7.8 Hz, 1H), 2.36 (s, 3H), 2.35 (s, 3H); MS 329 (MH⁺).

Step B: Preparation of N-[2-(4-methoxyphenyl)ethyl]-3,4-dimethyl-(α-nitromethyl)-benzenemethanamine hydrochloride: To a solution of 3,4-dimethyl-[(1E)-2-nitroethenyl]benzene (10.1 g, 0.057 mol) in THF (28 mL) at 21° C. is added 4-methoxyphenylethylamine (3.0 mL, 0.055 mol) dropwise over 6 minutes, keeping the temp below 30° C. with a water bath. The reaction is stirred for 24 minutes at ambient temperature, cooled in an ice bath, diluted with ether (80 mL), and 2 N HCl/ether (34 mL, 0.1068 mol) is added slowly, keeping the temperature below 15° C. The mixture is stirred in the cold for 30 minutes and the off-white solid which forms is collected by filtration to afford 18.4 g (89% yield) of the desired compound. ¹H NMR (CDCl₃) δ 10.7 (m, 1H), 10.3 (m, 1H), 7.39-7.44 (m, 2H), 7.25 (d, J=7.2 Hz, 1H), 7.12 (m, 2H), 6.82 (m, 2H), 5.77 (m, 1H), 5.23 (m, 1H), 4.87 (m, 1H), 3.79 (s, 3H), 3.29 (m, 1H), 3.15 (m, 1H), 3.02 (m, 2H), 2.32 (s, 3H), 2.30 (s, 3H); MS 329 (MH⁺).

Step C: Preparation of N¹-[2-(4-methoxyphenyl)ethyl]-1-(3,4-dimethylphenyl)-1,2-ethanediamine: To a mixture of N-[2-(4-methoxyphenyl)ethyl]-3,4-dimethyl-(α-nitromethyl)-benzenemethanamine in absolute ethanol (76 mL) at room temperature is added concentrated HCl (76 mL) slowly, keeping the temperature at less than 37° C. with a water bath. The mixture is cooled in an ice bath to 5° C. and zinc dust (11 g, 0.17 mol) is added in portions (starting with 0.5 g addition) over 50 minutes at less than 12° C. The reaction is stirred for 5 minutes and the ice bath is removed. The reaction temperature rises quickly to about 20° C. and the reaction is maintained below about 32° C. with an ice bath. The reaction is stirred for 70 minutes at 20° C. to 27° C. and any unreacted zinc is removed by filtration. The volume of the filtrate is reduced in vacuo then diluted with water (25 mL) and dichloromethane (150 mL). To the stirred mixture is added concentrated ammonium hydroxide (140 mL), keeping the temperature below about 32° C. with an ice bath. The organic phase is separated, washed with brine, dried (Na₂SO₄), and concentrated to afford 12 g (quantitative yield) of the desired compound as an oil. MS 299 (MH⁺).

Step D: Preparation of 1-[2-(4-methoxyphenyl)ethyl]-5-(3,4-dimethylphenyl)-2-imidazolidinone: To a solution of N¹-[2-(4-methoxyphenyl)ethyl]-1-(3,4-dimethylphenyl)-1,2-ethanediamine (10.6 g, 0.0356 mol) in dry DMF (55 mL) is added 1,1'-carbonyldiimidazole (6.4 g, 0.0395 mol). The reaction is stirred at 50° C. for 30 minutes, cooled, diluted with ethyl acetate (300 mL), and washed with 0.5 N HCl and brine. The organic phase is dried (MgSO₄), and concentrated. The residue is re-crystallized from ethyl acetate (70 mL) to afford 7.5 g (65% yield) of the desired compound. ¹H NMR (CDCl₃) δ 7.16 (d, J=7.8 Hz, 2H), 7.05 (m, 4H), 6.84 (d, J=7.8 Hz, 2H), 4.50 (t, J=8.1 Hz, 1H), 3.82 (s, 3H), 3.73-3.65 (m, 2H), 3.27 (t, J=8.4 Hz, 1H), 2.91 (m, 1H), 2.78 (m, 1H), 2.68 (m, 1H), 2.30 (s, 6H). MS 325 (MH⁺). Anal. Calcd. For C₂₀H₂₄N₂O₂·¼H₂O: C, 73.03; H, 7.51; N, 8.52. Found: C, 73.29; H, 7.19; N, 8.32.

Step E: Preparation of 1-amino-3-[2-(4-methoxyphenyl)ethyl]-4-(3,4-dimethylphenyl)-2-imidazolidinone hydrochloride: To a solution of 1-[2-(4-methoxyphenyl)ethyl]-5-(3,4-dimethylphenyl)-2-imidazolidinone (2.0 g, 0.0062 mol) in glacial acetic acid (21 mL) is added a solution of sodium nitrite (0.58 g, 0.0084 mol) in H₂O (2.8 mL) at room temperature over 2 minutes. The solution is stirred for 30 minutes and then cooled to 8° C. Zinc dust (0.84 g, 0.013 mol) is added at 8° C. to 18° C. in portions and the mixture is stirred two hours at 12° C. to 18° C. The reaction is cooled in an ice bath and dichloromethane (20 mL) and H₂O (20 mL) are added. Then concentrated ammonium hydroxide (34 mL) is added slowly, maintaining the temperature below 25° C. The organic layer is separated, washed with brine, dried (Na₂SO₄), treated with 2 M HCl/ether (3.3 mL) and concentrated. The residue is heated in ethyl acetate (8 mL) and diluted slowly with hexanes (30 mL). The resulting solid is collected and triturated with 20% ether/hexanes (50 mL). The solid is collected and re-crystallized from ethyl acetate (8 mL) to afford 1.88 g (81% yield) of the desired compound. ¹H NMR (CDCl₃) δ 7.06 (m, 3H), 6.95 (d, J=8.1 Hz, 2H), 6.74 (d, J=8.1 Hz, 2H), 4.42 (m, 1H), 4.25 (m, 1H), 3.90 (m, 1H), 3.75 (s, 3H), 3.60 (m, 1H), 2.89 (m, 1H), 2.71 (m, 1H), 2.58 (m, 1H), 2.21 (s, 3H), 2.20 (s, 3H). MS 340 (MH⁺). Anal. calcd. for C₂₀H₂₅N₃O₂·HCl: C, 63.91, H, 6.97; N, 11.18. Found: C, 63.71, H, 6.67; N, 11.18.

Exemplary compounds of the present invention can be prepared utilizing the following procedure described in Example 2 for preparing intermediates such as N¹-[2-(4-methoxyphenyl)ethyl]-1-(4-methoxyphenyl)-1,2-ethanediamine which can be suitably used to prepare the compounds according to the present invention. This procedure can be coupled with steps (D) and (E) from Example 1 to prepare exemplary 1-N-amino-2-imidazolidinone compounds of the present invention.

EXAMPLE 2

N¹-[2-(4-methoxyphenyl)ethyl]-1-(4-methoxyphenyl)-1,2-ethanediamine

Preparation of (4-methoxyphenyl)-trimethylsilanyloxyacetonitrile: To a solution of 4-methoxybenzaldehyde (1 mL, 8.2 mmol) and trimethylsilyl cyanide (1.3 mL, 10.25 mmol) is added zinc iodide (50 mg, 0.15 mmol). The resulting exothermic reaction is controlled using an ice-bath. The temperature is maintained below 65° C. The reaction is allowed to cool and the crude material is used without isolation.

Preparation of (4-methoxyphenyl)-[2-(4-methoxyphenyl)ethylamino]acetonitrile: 4-Methoxyphenethylamine (1.2 mL, 8.2 mmol) and methanol (0.5 mL) are added to the crude material obtained above. The solution is heated to 125° C. for 15 minutes in a microwave reaction vessel after which the solution is concentrated in vacuo and the crude product obtained is used without further purification.

Preparation of $N^1$-[2-(4-methoxyphenyl)ethyl]-1-(4-methoxyphenyl)-1,2-ethanediamine: The crude (4-methoxyphenyl)-[2-(4-methoxyphenyl)ethylamino]-acetonitrile obtained in the above procedure is dissolved in diethyl ether (20 mL) and this solution is slowly added to an ice-cold solution of lithium aluminum hydride (1.0M, 16 mL, 16 mmol) in diethyl ether. The cooling bath is removed and the solution is allowed to stir for 1 hour. The reaction solution is then re-cooled to 5° C. and water (4 mL) is added, followed by 3N NaOH (3 mL). The ether is then decanted from the resulting solid and the solid is again washed with diethyl ether (20 mL). The combined ether washings are dried ($Na_2SO_4$) and concentrated in vacuo to afford 2.5 g (quantitative yield) of the desired compound. MS (301) ($MH^+$).

The following are non-limiting examples of compounds of Formula IX.

Compound 2: 1-Amino-4-[4-(tert-butyl)phenyl]-3-[2-(4-methoxyphenyl)ethyl]-2-imidazolidinone. An alternative name for this compound is 1-Amino-3-[2-(4-methoxyphenyl)ethyl]-4-[4-(tert-butyl)phenyl]-2-imidazolidinone. $^1$H-NMR (DMSO-$d_6$): δ 7.47 (d, J=8.1 Hz, 2H), 7.33 (d, J=8.1 Hz, 2H), 7.04 (d, J=8.4 Hz, 2H), 6.82 (d, J=8.4 Hz, 2H), 4.67 (t, J=7.8 Hz, 1H), 3.87 (t, J=7.8 Hz, 1H), 3.71 (s, 3H), 3.55 (m, 1H), 3.34 (t, J=8.1 Hz, 1H), 2.64 (m, 5H), 1.29 (s, 9H). MS m/z (ESI, positive): 368 [M+H]$^+$.

Compound 3: 1-Amino-4-(4-methoxyphenyl)-3-[3-(4-methoxyphenyl)propyl]-2-imidazolidinone. An alternative name for this compound is 1-Amino-3-[3-(4-methoxyphenyl)propyl]-4-(4-methoxyphenyl)-2-imidazolidinone: $^1$H NMR (DMSO-$d_6$) δ 7.49 (d, J=8.1 Hz, 2H), 7.32 (d, J=9.0 Hz, 2H), 7.11 (d, J=8.1 Hz, 2H), 7.03 (d, J=8.7 Hz, 2H), 6.99 (d, J=8.4 Hz, 2H), 6.80 (d, J=9.0 Hz, 2H), 4.78 (t, J=7.8 Hz, 1H), 3.86 (t, J=7.8 Hz, 1H), 3.77 (s, 3H), 3.70 (s, 3H), 3.29 (m, 2H), 2.51 (m, 1H), 2.39 (m, 2H), 2.28 (s, 3H), 1.56 (m, 2H). MS 356 (MH$^+$). Anal. Calcd. For $C_{27}H_{33}N_3O_6S$: C, 61.46; H, 6.30; N, 7.96. Found: C, 61.92; H, 6.29; N, 7.86.

Compound 4: 1-Amino-4-(4-cyclopropylphenyl)-3-[3-(4-methoxyphenyl)propyl]-2-imidazolidinone. An alternative name for this compound is 1-Amino-3-[3-(4-methoxyphenyl)propyl]-4-(4-cyclopropylphenyl)-2-imidazolidinone: $^1$H NMR (DMSO-$d_6$) δ 7.55 (d, J=8.1 Hz, 2H), 7.28 (d, J=8.1 Hz, 2H), 7.13 (m, 4H), 7.03 (d, J=8.7 Hz, 2H), 6.81 (d, J=8.7 Hz, 2H), 4.80 (t, J=7.8 Hz, 1H), 3.90 (t, J=7.8 Hz, 1H), 3.71 (s, 3H), 3.32 (m, 2H), 2.67 (m, 1H), 2.40 (m, 2H), 2.29 (s, 3H), 1.93 (m, 1H), 1.57 (m, 2H), 0.96 (m, 2H), 0.69 (m, 2H). MS 366 (MH$^+$). Anal. Calcd. For $C_{29}H_{35}N_3O_5S$: C, 64.78; H, 6.56; N, 7.82. Found: C, 63.90; H, 6.43; N, 7.52.

Compound 5: 1-Amino-3-[2-(4-methoxyphenyl)ethyl]-4-(4-difluoromethoxyphenyl)-2-imidazolidinone 4-methylbenzenesulfonic acid salt. $^1$H NMR (CDCl$_3$) δ 7.79 (d, J=8.1 Hz, 2H), 7.06 (m, 4H), 6.91 (m, 4H), 6.75 (d, J=8.7 Hz, 2H), 6.49 (t, J=73.5 Hz, 1H), 4.27 (t, J=8.1, 1H), 3.98 (t, J=8.1 Hz, 1H), 3.76 (s, 3H), 3.52 (m, 2H), 2.73 (m, 1H), 2.64 (m, 1H), 2.50 (m, 1H), 2.28 (s, 3H). MS 378 (MH$^+$). Anal. calcd. for $C_{19}H_{21}F_2N_3O_3 \cdot C_7H_8O_3S$: C, 56.82, H, 5.32; N, 7.65. Found: C, 57.04, H, 5.22; N, 7.52.

Compound 6: 1-Amino-3-[2-(4-methoxyphenyl)ethyl]-4-(4-cyclopropylphenyl)-2-imidazolidinone 4-methylbenzenesulfonic acid salt. $^1$H NMR (CDCl$_3$) δ 7.50 (m, 2H), 7.27 (d, J=8.4 Hz, 2H), 7.14 (m, 4H), 7.05 (d, J=8.4 Hz, 2H), 6.84 (d, J=8.7 Hz, 2H), 4.68 (t, J=8.1 Hz, 1H), 3.84 (t, J=7.8 Hz, 1H), 3.73 (s, 3H), 3.56 (m, 1H), 3.23 (t, J=8.1 Hz, 1H), 2.77 (m, 1H), 2.65 (m, 1H), 2.62 (m, 1H), 2.21 (s, 3H), 2.30 (s, 3H), 1.95 (m, 1H), 0.98 (m, 2H), 0.71 (m, 2H). MS 352 (MH$^+$). Anal. calcd. for $C_{21}H_{25}N_3O_2 \cdot C_7H_8O_3S \cdot ¼H_2O$: C, 63.68; H, 6.39; N, 7.96. Found: C, 63.65; H, 6.35; N, 7.94.

Exemplary compounds having Formula XI can be prepared by the procedure described in Example 3 herein below. The skilled practitioner will know how to substitute the appropriate reagents, starting materials and purification methods known to those skilled in the art, in order to prepare additional compounds of the present invention.

EXAMPLE 3

Compound 7: 1-(Methylsulfonylamino)-3-[2-(4-methoxyphenyl)ethyl]-4-(3,4-dimethylphenyl)-2-imidazolidinone Preparation of 1-(methylsulfonylamino)-3-[2-(4-methoxyphenyl)ethyl]-4-(3,4-dimethylphenyl)-2-imidazolidinone: A solution of 1-amino-3-[2-(4-methoxyphenyl)-ethyl]-4-(3,4-dimethylphenyl)-2-imidazolidinone hydrochloride (300 mg, 0.80 mmol) in dichloromethane (3.0 mL) and Hunig's base (0.31 mL, 1.8 mmol) is cooled in an ice bath and methanesulfonyl chloride (0.068 mL, 0.88 mmol) is added dropwise. The reaction is stirred cold for 45 minutes and washed with 0.1 N HCl (2×) and H$_2$O. The organic phase is dried (Na$_2$SO$_4$), and concentrated to a white foam. The crude material is purified over silica (1.5% MeOH/dichloromethane) to afford 161 mg (48% yield) of the desired compound. $^1$H NMR (CDCl$_3$) δ 7.17 (d, J=8.1 Hz, 1H), 7.07 (m, 2H), 7.00 (m, 2H), 6.85 (m, 3H), 4.45 (t, J=8.1 Hz, 1H), 3.96 (t, J=8.1 Hz, 1H), 3.81 (s, 3H), 3.74 (m, 1H), 3.33 (t, J=8.4 Hz, 1H), 3.06 (s, 3H), 2.97 (m, 1H), 2.76 (m, 1H), 2.67 (m, 1H), 2.30 (s, 6H).). MS 418 (MH$^+$). Anal. Calcd. for $C_{21}H_{27}N_3O_4S \cdot ¼H_2O$: C, 59.77, H, 6.57; N, 9.96. Found: C, 59.82, H, 6.06; N, 9.85. FAB-HRMS: anal. calcd for $C_{21}H_{27}N_3O_4S$: 418.18005. Found: 418.17960.

The following are non-limiting examples of compounds of Formula XI.

Compound 8: 1-(Aminosulfonylamino)-3-[2-(4-methoxyphenyl)ethyl]-4-(3,4-dimethylphenyl)-2-imidazolidinone: $^1$H-NMR (CDCl$_3$) δ: 7.59 (s, 1H), 7.17 (d, J=8.4 Hz, 2H), 7.06 (m, 4H), 6.84 (d, J=9 Hz, 2H), 5.37 (s, 2H), 4.49 (t, J=8.1 Hz, 1H), 4.00 (t, J=8.1 Hz, 1H), 3.81 (s, 3H), 3.42 (t, J=8.1 Hz, 1H), 2.95 (m, 1H), 2.7 (m, 2H), 2.29 (d, J=2.7 Hz, 6H). MS m/z (ESI, positive): 418 [M+H]$^+$, 440 [M+Na]$^+$. Anal Calcd for $C_{20}H_{26}N_4O_4S$: C, 57.40; H, 6.26; N, 13.39. Found: C, 57.64; H, 6.40; N, 13.10.

Compound 9: 1-(Aminosulfonylamino)-3-[2-(4-methoxyphenyl)ethyl]-4-[4-(tert-butyl)phenyl]-2-imidazolidinone: $^1$H-NMR (CDCl$_3$) δ: 7.93 (s, 1H), 7.39 (d, J=7.2 Hz, 2H), 7.22 (d, J=7.5 Hz, 2H), 7.05 (d, J=7.5 Hz, 2H), 6.81 (d, J=7.2 Hz, 2H), 5.67 (s, 2H), 4.52 (t, J=8.4 Hz, 1H), 4.01 (t, J=8.4 Hz, 1H), 3.78 (s, 3H), 3.65 (m, 1H), 3.44 (t, J=8.4 Hz, 1H), 2.96 (m, 1H), 2.71 (m, 2H), 1.33 (s, 9H). MS m/z (ESI, positive): 447 [M+H]$^+$. Anal calcd for $C_{22}H_{30}N_4O_4S$: C, 59.17; H, 6.77; N, 12.55. Found: C, 59.52; H, 6.98; N, 12.46.

Compound 10: 1-(Aminosulfonylamino)-3-[2-(4-methoxyphenyl)ethyl]-4-[(4-cyclopropyl)-phenyl]-2-imidazolidinone: $^1$H NMR δ (DMSO-$d_6$) 8.6 (s, 1H), 7.25 (d, J=7.8 Hz, 1H), 7.15 (d, J=7.8 Hz, 2H), 7.0 (m, 4H), 6.85 (d, J=7.8 Hz, 2H), 4.55 (t, J=7 Hz, 1H), 3.9 (t, J=6 Hz, 1H), 3.75 (s, 3H), 3.4 (m, 2H), 2.7 (m, 2H), 2.45 (m, 1H), 1.9 (m, 1H), 1.0 (m, 2H), 0.75 (m, 2H). Anal. calcd. for $C_{21}H_{26}N_4O_4S \cdot 0.25H_2O$: C, 57.99; H, 6.13; N, 12.88; found C, 53.11; H, 6.17; N, 12.52. FAB-HRMS calcd. 431.1753; found 431.1757 (MH$^+$).

Compound 11: 1-(Methylsulfonylamino)-3-[2-(4-methoxyphenyl)ethyl]-4-[(4-tert-butyl)benzyl]-2-imidazolidinone: $^1$H NMR (DMSO-d$_6$) δ 9.4 (s, 1H) 7.35 (d, J=7.8 Hz, 2H), 7.2 (d, J=7.8 Hz, 2H), 7.1 (d, J=7.8 Hz, 2H), 6.8 (d, J=7.8 Hz, 2H), 3.8 (m, 1H), 3.7 (s, 3H), 3.5 (m, 1H), 3.3 (m, 1H), 3.25-3.1 (m, 2H), 3.0 (m, 1H), 2.85 (s, 3H), 2.8-2.5 (m, 3H), 1.25 (s, 9H). Anal. calcd. for $C_{24}H_{33}N_3O_4S$: C, 62.72; H, 7.24; N, 9.14; found C, 62.49; H, 7.01; N, 8.91. FAB-HRMS calcd. 460.2270; found 460.2284 (MH$^+$).

Compound 12: 1-(Methylsulfonylamino)-3-[2-(4-methoxyphenyl)ethyl]-4-[(3-methyl-4-methoxy)phenyl]-2-imidazolidinone: $^1$H NMR (DMSO-d$_6$) δ 9.5 (s, 1H), 7.16 (d, J=7.8 Hz, 1H), 7.12 (s, 1H) 7.05 (d, J=7.8 Hz, 2H), 6.95 (d, J=7.8 Hz, 2H), 6.8 (d, J=7.8 Hz, 2H), 4.55 (t, J=8 Hz, 1H), 3.85 (m, 1H), 3.8 (s, 3H), 3.7 (s, 3H), 3.5 (m, 1H), 3.25 (m, 1H), 3.0 (s, 3H), 2.85-2.55 (m, 3H), 2.2 (s, 3H). FAB-HRMS calcd. for $C_{21}H_{27}N_3O_5S$: 434.1750; found 434.1751 (MH$^+$).

Compound 13: 1-(Methylsulfonylamino)-3-[2-(4-methoxyphenyl)ethyl]-4-[(3-methoxy-4-methyl)phenyl]-2-imidazolidinone: $^1$H NMR (DMSO-d$_6$) δ 9.5 (s, 1H), 7.2 (d, J=7.8 Hz, 1H), 7.1 (d, J=8.4 Hz, 2H), 6.95 (s, 1H), 6.85 (m, 3H), 4.6 (t, J=8 Hz, 1H), 3.85 (m, 1H), 3.8 (s, 3H), 3.7 (s, 3H), 3.5 (m, 1H), 3.3 (m, 1H), 3.0 (s, 3H), 2.85-2.55 (m, 3H), 2.2 (s, 3H). Anal. calcd. for $C_{21}H_{28}N_3O_5S$: C, 58.18; H, 6.28; N, 9.69; found C, 57.94; H, 6.45; N, 9.32. FAB-HRMS calcd. 434.1750; found 434.1752 (MH$^+$).

Compound 14: 1-(Methylsulfonylamino)-3-[2-(4-methoxyphenyl)ethyl]-4-[(4-isopropyloxy)-phenyl]-2-imidazolidinone: $^1$H NMR (DMSO-d$_6$) δ 9.5 (s, 1H), 7.3 (d, J=7.8 Hz, 2H), 7.1 (d, J=8.4 Hz, 2H), 7.0 (d, J=8.4 Hz, 2H), 6.9 (d, J=7.8 Hz, 2H), 4.6 (m, 1H), 3.85 (m, 1H), 3.75 (s, 3H), 3.4 (m, 1H), 3.25 (m, 1H), 3.0 (s, 3H), 2.8-2.5 (m, 3H), 1.3 (d, 6H). Anal. calcd. for $C_{22}H_{29}N_3O_5S \cdot 0.25H_2O$: C, 58.46; H, 6.57; N, 9.29; found C, 58.42; H, 6.56; N, 9.15. FAB-HRMS calcd. 448.1906; found 448.1912 (MH$^+$).

Compound 15: 1-(Methylsulfonylamino)-3-[2-(4-methoxyphenyl)ethyl]-4-(benzo[1,3]dioxol-5-yl)-2-imidazolidinone: $^1$H NMR (DMSO-d$_6$) δ 9.45 (s, 1H), 7.05 (d, J=7.8 Hz, 2H), 6.9-6.8 (m, 5H), 6.0 (s, 2H), 4.6 (t, J=6 Hz, 1H), 3.8 (t, J=6 Hz, 1H), 3.7 (s, 3H), 3.5 (m, 1H), 3.3 (t, J=7 Hz, 1H), 3.0 (s, 3H), 2.85-2.55 (m, 3H). Anal. calcd. for $C_{20}H_{23}N_3O_6S \cdot 0.5H_2O$: C, 54.29; H, 5.46; N, 9.49; found C, 54.67; H, 5.31; N, 9.41. FAB-HRMS calcd. 434.1386; found 434.1365 (MH$^+$).

Compound 16: 1-(Methylsulfonylamino)-3-[2-(4-methoxyphenyl)ethyl]-4-(2,2-difluorobenzo-[1,3]dioxol-5-yl)-2-imidazolidinone: $^1$H NMR (DMSO-d$_6$) δ 9.5 (s, 1H), 7.45 (d, J=7.8 Hz, 1H), 7.35 (d, J=7.8 Hz, 1H), 7.25 (d, J=7.8 Hz, 1H), 7.1 (d, J=7.8 Hz, 2H), 6.8 (d, J=7.8 Hz, 2H), 4.7 (t, J=6 Hz, 1H), 3.9 (t, J=7 Hz, 1H), 3.8 (s, 3H), 3.5 (m, 1H), 3.25 (t, J=7 Hz, 1H), 3.0 (s, 3H), 2.9-2.55 (m, 3H). Anal. calcd. for $C_{20}H_{21}F_2N_3O_6S$: C, 51.17; H, 4.51; N, 8.95; found C, 51.20; H, 4.66; N, 8.63. FAB-HRMS calcd. 470.1197; found 470.1190 (MH$^+$).

Compound 17: 1-(Methylsulfonylamino)-3-[2-(4-methoxyphenyl)ethyl]-4-[(2,3-dihydro-benzo[1,4]dioxin-6-yl)]-2-imidazolidinone: $^1$H NMR δ (DMSO-d$_6$) δ 9.5 (s, 1H), 7.1 (d, J=7.8 Hz, 2H), 6.9-6.8 (m, 5H), 4.55 (t, J=8 Hz, 1H), 4.25 (s, 4H), 3.8 (t, J=8 Hz, 1H), 3.7 (s, 3H), 3.5 (m, 1H), 3.25 (t, J=8 Hz, 1H), 2.8-2.55 (m, 3H). Anal. calcd. for $C_{21}H_{25}N_3O_6S \cdot 0.5H_2O$: C, 55.75; H, 5.73; N, 9.20; found C, 55.58; H, 5.67; N, 9.22. FAB-HRMS calcd. 448.1542; found 448.1538 (MH$^+$).

Compound 18: 1-(Methylsulfonylamino)-3-[2-(4-methoxyphenyl)ethyl]-4-(2,2-dimethylbenzo-[1,3]dioxol-5-yl)-2-imidazolidinone: $^1$H NMR (DMSO-d$_6$) δ 9.45 (s, 1H), 7.1 (d, J=7.8 Hz, 2H), 6.9-6.8 (m, 5H), 4.6 (t, J=6 Hz, 1H), 3.8 (t, J=6 Hz, 1H), 3.7 (s, 3H), 3.5 (m, 1H), 3.3 (t, J=7 Hz, 1H), 3.0 (s, 3H), 2.85-2.55 (m, 3H), 1.8 (s, 6H). Anal. calcd. for $C_{22}H_{27}N_3O_6S \cdot 0.2H_2O$: C, 56.81; H, 5.93; N, 9.03; found C, 57.14; H, 5.94; N, 8.68; FAB-HRMS calcd. 462.1699; found 462.1718 (MH$^+$).

Compound 19: 1-(Methylsulfonylamino)-3-[(4-methoxyphenyl)methyl]-4-(4-cyclopropylphenyl)-2-imidazolidinone. $^1$H NMR (CDCl$_3$) δ 7.34 (s, 1H), 7.12 (q, J=8.4 Hz, 6.3 Hz, 4H), 7.01 (d, J=8.1 Hz, 2H), 6.84 (d, J=7.8 Hz, 2H), 4.80 (d, J=14.7 Hz, 1H), 4.34 (t, J=8.4 Hz, 1H), 3.94 (t, J=8.4 Hz, 1H), 3.81 (s, 3H), 3.58 (d, J=14.7 Hz, 1H), 3.40 (t, J=8.4 Hz, 1H), 3.18 (s, 3H), 1.93 (m, 1H), 1.02 (m, 2H), 0.73 (m, 2H). (MS) 416 (MH$^+$), 438 (MNa$^+$). HRMS found for $C_{21}H_{26}N_3O_4S$.

Compound 20: 1-(Methylsulfonylamino)-3-[2-(4-methoxyphenyl)ethyl]-4-(4-methylphenyl)-2-imidazolidinone. $^1$H NMR (CDCl$_3$) δ 7.31 (s, 1H), 7.22 (d, J=8.1 Hz, 2H), 7.17 (d, J=8.4 Hz, 2H), 7.06 (d, J=8.4 Hz, 2H), 6.84 (d, J=8.7 Hz, 2H), 4.47 (t, J=8.4 Hz, 1H), 3.97 (t, J=8.4 Hz, 2H), 3.79 (s, 3H), 3.72 (m, 1H), 3.36 (t, J=8.4 Hz, 1H), 3.08 (s, 3H), 2.96 (m, 1H), 2.76 (m, 1H), 2.66 (m, 1H), 2.39 (s, 3H). MS 404 (MH$^+$). Anal. Calcd for $C_{20}H_{25}N_3O_4S$: C, 59.53; H, 6.25; N, 10.41. Found: C, 59.91; H, 6.44; N, 10.55.

Compound 21: 1-(Methylsulfonylamino)-3-[2-(4-methoxyphenyl)ethyl]-4-(4-chlorophenyl)-2-imidazolidinone. $^1$H NMR (CDCl$_3$) δ 7.37 (d, J=8.4 Hz, 2H), 7.19 (m, 3H), 7.04 (d, J=8.4 Hz, 2H), 6.83 (d, J=8.7 Hz, 2H), 4.44 (t, J=7.8 Hz, 1H), 3.95 (t, J=8.4 Hz, 2H), 3.79 (s, 3H), 3.72 (m, 1H), 3.32 (t, J=8.1 Hz, 1H), 3.07 (s, 3H), 2.93 (m, 1H), 2.69 (m, 2H). MS (424) (MH$^+$), 446 (MNa$^+$), 422 (M-H$^-$). Anal. Calcd for $C_{19}H_{22}ClN_3O_4S$: C, 53.83; H, 5.23; N, 9.91. Found: C, 55.51; H, 5.56; N, 9.38.

Compound 22: 1-(Methylsulfonylamino)-3-[2-(4-methoxyphenyl)ethyl]-4-(4-trifluoromethyl-phenyl)-2-imidazolidinone. $^1$H NMR (CDCl$_3$) δ 7.67 (d, J=8.1 Hz, 2H), 7.37 (d, J=8.1 Hz, 2H), 7.13 (s, 1H), 7.05 (d, J=8.4 Hz, 2H), 6.83 (d, J=8.7 Hz, 2H), 4.50 (t, J=8.1 Hz, 1H), 3.98 (t, J=8.4 Hz, 1H), 3.77 (m, 4H), 3.56 (t, J=8.1 Hz, 1H), 3.08 (s, 3H), 2.94 (m, 1H), 2.72 (m, 2H). (MS) 458 (MH$^+$), 480 (MNa$^+$). HRMS found for $C_{20}H_{23}N_3O_4SF_3$.

Compound 23: 1-(Methylsulfonylamino)-3-[2-(4-methoxyphenyl)ethyl]-4-(4-methoxyphenyl)-2-imidazolidinone: $^1$H NMR (CDCl$_3$) δ 7.20 (d, J=8.7 Hz, 3H), 7.05 (d, J=8.7 Hz, 2H), 6.93 (d, J=8.7 Hz, 2H), 6.84 (d, J=8.7 Hz, 2H), 4.45 (t, J=8.4 Hz, 1H), 3.96 (t, J=8.25 Hz, 1H), 3.84 (s, 3H), 3.80 (s, 3H), 3.69 (m, 1H), 3.35 (t, J=8.55 Hz, 1H), 3.08 (s, 3H), 2.96 (m, 1H), 2.76 (m, 1H), 2.65 (m, 1H). MS (m/z ESI): 420 (MH$^+$), 418 [M-H]$^-$. Anal Calcd for $C_{20}H_{25}N_3O_5S$: C, 57.26; H, 6.01; N, 10.02. Found: C, 57.18; H, 6.06; N, 9.98.

Compound 24: 1-(Methylsulfonylamino)-3-[(4-methoxyphenyl)ethyl]-4-[4-(tert-butyl)phenyl]-imidazolidinone. An alternative name for compound 24 is 1-(Methylsulfonylamino)-3-[(4-methoxyphenyl)ethyl]-4-[4-(tert-butyl)phenyl]-2-imidazolidinone. $^1$H NMR (CDCl$_3$) δ 7.70 (d, J=8.4 Hz, 2H), 7.44 (d, J=8.4 Hz, 2H), 7.21 (d, J=8.4 Hz, 2H), 7.11 (s, 1H), 6.85 (d, J=9 Hz, 2H), 4.49 (t, J=8.4 Hz, 1H), 3.97 (t, J=8.4 Hz, 1H), 3.89 (t, J=8.4 Hz, 1H), 3.81 (s, 3H), 3.76 (m, 1H), 3.08 (s, 3H), 2.99 (m, 1H), 2.71 (m, 2H), 1.36 (s, 9H). MS m/z (ESI, positive): 446 (MH$^+$). Anal Calcd for $C_{23}H_{31}N_3O_4S$: C, 62.00; H, 7.01; N, 9.43. Found: C, 61.93, 61.77; H, 6.62, 6.83; N, 9.11, 9.13.

Compound 25: 1-(Methylsulfonylamino)-3-[2-(4-methoxyphenyl)ethyl]-4-[(4-diethylamino)-phenyl]-2-imidazolidinone: $^1$H NMR (DMSO-d$_6$) δ 9.45 (s, 1H), 7.1 (d, J=7.8 Hz, 2H), 7.0 (d, J=7.8 Hz, 2H), 6.8 (d, J=7.8 Hz, 2H), 6.65 (d, J=7.8 Hz, 2H), 4.5 (t, J=8 Hz, 1H), 3.75 (t, J=8 Hz, 1H), 3.7 (s, 3H), 3.45 (m, 2H), 3.35 (q, J=8 Hz, 4H), 3.2 (t, J=8 Hz, 1H), 3.0 (s, 3H), 2.8-2.6 (m, 2H), 1.1 (t, J=8 Hz, 6H). Anal. calcd. for C$_{23}$H$_{32}$N$_4$O$_4$S. 0.5H$_2$O: C, 58.83; H, 7.07; N, 11.93; found C, 58.85; H, 7.04; N, 11.80. FAB-HRMS calcd. 461.2223; found 461.2243 (MH$^+$).

Compound 26: 1-[(Methylsulfonyl)amino]-3-[2-(4-methoxyphenyl)ethyl]-4-(4-difluoro-methoxyphenyl)-2-imidazolidinone. $^1$H NMR (CDCl$_3$) δ 7.26 (d, J=8.7 Hz, 2H), 7.17 (d, J=8.4 Hz, 3H), 7.05 (d, J=8.7 Hz, 2H), 6.93 (s, 1H), 6.84 (d, J=8.4 Hz, 2H), 6.56 (t, J=73.5 Hz, 1H), 4.76 (t, J=8.1 Hz, 1H), 3.96 (t, J=8.7 Hz, 1H), 3.81 (s, 3H), 3.72 (m, 1H), 3.34 (t, J=8.1 Hz, 1H), 3.07 (s, 3H), 2.96 (m, 1H), 2.75 (m, 1H), 2.71 (m, 1H). MS 456 (MH$^+$). Anal. calcd. for C$_{20}$H$_{23}$F$_2$N$_3$O$_5$S % H$_2$O: C, 52.22, H, 5.15; N, 9.14. Found: C, 52.12, H, 4.87; N, 8.92.

Compound 27: 1-[(Methylsulfonyl)amino]-3-[2-(4-methoxyphenyl)ethyl]-4-(4-trifluoro-methoxyphenyl)-2-imidazolidinone: $^1$H NMR (CDCl$_3$) δ 7.28 (s, 4H), 7.03 (d, J=8.4 Hz, 2H), 6.85 (d, J=8.4 Hz, 2H), 6.72 (s, 1H), 4.47 (t, J=8.4, 1H), 3.97 (t, J=8.4 Hz, 1H), 3.82 (s, 3H), 3.76 (m, 1H), 3.35 (t, J=8.4 Hz, 1H), 3.07 (s, 3H), 2.97 (m, 1H), 2.76 (m, 1H), 2.70 (m, 1H). MS 496 (MH$^+$). Anal. calcd. for C$_{20}$H$_{22}$F$_3$N$_3$O$_5$S: C, 50.74, H, 4.68; N, 8.87. Found: C, 50.74, H, 4.80; N, 8.46.

Compound 28: 1-[(Methylsulfonyl)amino]-3-[(4-methoxyphenyl)ethyl]-4-(4-cyclopropylphenyl)-2-imidazolidinone. $^1$H NMR (CDCl$_3$) δ 7.11 (m, 7H), 6.83 (d, J=8.7 Hz, 2H), 4.45 (t, J=8.4 Hz, 1H), 3.95 (t, J=8.4 Hz, 1H), 3.80 (s, 3H), 3.72 (m, 1H), 3.34 (t, J=8.4 Hz, 1H), 3.07 (s, 3H), 2.97 (m, 1H), 2.68 (m, 2H), 1.93 (m, 1H), 1.02 (m, 2H), 0.74 (m, 2H). MS m/z (ESI, positive): 430 (MH$^+$). Anal calcd for C$_{22}$H$_{27}$N$_3$O$_4$S: C, 61.52: H, 6.34; N, 9.78. Found: C, 61.74; H, 6.20; N, 9.91.

Compound 29: 1-(Cyclopropylsulfonylamino)-3-[(4-methoxyphenyl)ethyl]-4-(4-methoxyphenyl)-2-imidazolidinone. $^1$H NMR (CDCl$_3$) δ 7.37 (s, 1H), 7.17 (d, J=8.1 Hz, 2H), 7.04 (d, J=8.1 Hz, 2H), 6.91 (d, J=7.8 Hz, 2H), 6.81 (d, J=7.8 Hz, 2H) 4.40 (t, J=8.1 Hz, 1H), 3.91 (t, J=8.1 Hz, 1H), 3.81 (s, 3H), 3.75 (m, 5H), 3.34 (t, J=8.1 Hz, 1H), 2.93 (m, 1H), 2.71 (m, 1H), 2.63 (m, 2H), 1.23 (m, 2H), 1.05 (m, 2H). MS 446 (MH$^+$).

Compound 30: 1-(Propylsulfonylamino)-3-[(4-methoxyphenyl)ethyl]-4-(4-cyclopropylphenyl)-2-imidazolidinone: $^1$H NMR (CDCl$_3$) δ 7.11 (m, 6H), 6.84 (m, 3H), 4.45 (t, J=8.4 Hz, 1H), 3.96 (t, J=8.4 Hz, 1H), 3.81 (s, 3H), 3.72 (m, 1H), 3.34 (t, J=8.4 Hz, 1H), 3.16 (t, J=7.8 Hz, 2H), 2.96 (m, 1H), 2.71 (m, 2H), 1.99 (m, 3H), 1.12 (t, J=7.5 Hz, 3H), 1.02 (m, 2H), 0.75 (m, 2H). MS m/z (ESI, positive): 458 (MH$^+$), (ESI negative): 456 [M−H]$^−$. Anal calcd for C$_{24}$H$_{31}$N$_3$O$_4$S: C, 63.00; H, 6.83; N, 9.18. Found: C, 62.84; H, 7.05; N, 9.31.

Compound 31: 1-(Butylsulfonylamino)-3-[(4-methoxyphenyl)ethyl]-4-(4-cyclopropylphenyl)-2-imidazolidinone: $^1$H NMR (CDCl$_3$) δ 7.07 (m, 6H), 6.84 (m, 3H), 4.43 (t, J=8.4 Hz, 1H), 3.94 (t, J=8.4 Hz, 1H), 3.80 (s, 3H), 3.70 (m, 1H), 3.33 (t, J=8.4 Hz, 1H), 3.18 (t, J=7.8 Hz, 2H), 2.94 (m, 1H), 2.68 (m, 2H), 1.92 (m, 3H), 1.50 (m, 2H), 1.00 (m, 5H), 0.72 (m, 2H). MS m/z (ESI, positive): 472 (MH$^+$), 494 [M+Na]$^+$. Anal calcd for C$_{25}$H$_{33}$N$_3$O$_4$S: C, 63.67; H, 7.05; N, 8.91. Found: C, 63.92; H, 6.80; N, 9.04.

Compound 32: 1-(Butylsulfonylamino)-3-[(4-methoxyphenyl)-ethyl]-4-[4-(tert-butyl)phenyl]-2-imidazolidinone: $^1$H NMR (CDCl$_3$) δ 7.43 (d, J=8.1 Hz, 2H), 7.20 (d, J=8.4 Hz, 2H), 7.05 (m, 2H), 6.84 (m, 3H), 4.47 (t, J=8.1 Hz, 1H), 3.97 (t, J=8.1 Hz, 1H), 3.81 (s, 3H), 3.72 (m, 1H), 3.39 (t, J=8.4 Hz, 1H), 3.21 (t, J=7.8 Hz, 2H), 2.98 (m, 1H), 2.75 (m, 2H), 1.95 (m, 2H), 1.52 (m, 2H), 1.36 (s, 9H), 1.02 (t, J=7.5 Hz, 3H). MS m/z (ESI, positive): 488 (MH$^+$), 510 [M+Na]$^+$, (ESI negative): 486 [M−H]$^−$. Anal calcd for C$_{26}$H$_{37}$N$_3$O$_4$S: C, 64.04; H, 7.65; N, 8.62. Found: C, 63.94; H, 7.48; N, 8.90.

Compound 33: 1-(Vinylsulfonylamino)-3-[2-(4-methoxyphenyl)ethyl]-4-[(2,3-dihydrobenzo-[1,4]dioxin-6-yl)]-2-imidazolidinone: $^1$H NMR (DMSO-d$_6$) δ 9.7 (s, 1H), 7.1 (d, J=7.8 Hz, 2H), 6.9-6.9 (m, 6H), 6.2 (d, J=9 Hz, 1H), 6.1 (d, J=8 Hz, 1H), 4.5 (m, 1H), 4.25 (s, 4H), 3.8 (m, 1H), 3.75 (s, 3H), 3.4 (m, 2H), 3.2 (m, 1H), 2.75 (m, 2H). FAB-HRMS calcd. for C$_{22}$H$_{25}$N$_3$O$_6$S: 460.1542; found 460.1554 (MH$^+$).

Compound 34: 1-(Fluoromethylsulfonylamino)-3-[2-(4-methoxyphenyl)ethyl]-4-(4-cyclopropyl-phenyl)-2-imidazolidinone: $^1$H NMR (DMSO-d$_6$) δ 10.2 (s, 1H), 7.2 (d, J=7.8 Hz, 2H), 7.15 (d, J=7.8 Hz, 2H), 7.0 (d, J=7.8 Hz, 2H), 6.8 (d, J=7.8 Hz, 2H), 5.5 (m, 1H), 5.3 (m, 1H), 4.6 (t, J=8 Hz, 1H), 3.8 (t, J=8 Hz, 1H), 3.65 (s, 3H), 3.4 (m, 1H), 3.2 (m, 1H), 2.8-2.6 (m, 2H) 1.9 (m, 1H), 0.9 (d, J=8 Hz, 2H), 0.7 (d, J=4 Hz, 2H). Anal. calcd. for C$_{22}$H$_{26}$FN$_3$O$_4$S: C, 59.04; H, 5.86; N, 9.39; found C, 59.02; H, 5.62; N, 9.11. FAB-HRMS calcd. 448.1706; found 448.1710 (MH$^+$).

Compound 35: 1-(Fluoromethylsulfonylamino)-3-[2-(4-methoxyphenyl)ethyl]-4-(4-methoxy-phenyl)-2-imidazolidinone: $^1$H NMR (DMSO-d$_6$) δ 10.2 (s, 1H), 7.3 (d, J=7.8 Hz, 2H), 7.05 (d, J=7.8 Hz, 2H), 7.0 (d, J=7.8 Hz, 2H), 6.85 (s, J=7.8 Hz, 2H), 5.5 (m, 1H), 5.35 (m, 1H), 4.6 (t, J=8 Hz, 1H), 3.8 (t, J=8 Hz, 1H), 3.75 (s, 3H), 3.7 (s, 3H), 3.4 (m, 1H), 3.35 (s, 1H), 3.2 (t, J=8 Hz, 1H), 2.8-2.6 (m, 2H). Anal. calcd. for C$_{20}$H$_{24}$FN$_3$O$_5$S: C, 54.91; H, 5.53; N, 9.60; found, C, 54.63; H, 5.43; N, 9.67. FAB-HRMS calcd. 438.1449; found 438.1509 (MH$^+$).

Compound 36: 1-(Fluoromethylsulfonylamino)-3-[2-(4-methoxyphenyl)ethyl]-4-(4-tert-butyl-phenyl)-2-imidazolidinone: $^1$H NMR (DMSO-d$_6$) δ 10.2 (s, 1H), 7.5 (d, J=7.8 Hz, 2H), 7.3 (d, J=7.8 Hz, 2H), 7.05 (d, J=7.8 Hz, 2H), 6.8 (d, J=7.8 Hz, 2H), 5.5 (m, 1H), 5.3 (m, 1H), 4.6 (t, J=8 Hz, 1H), 3.85 (t, J=8 Hz, 1H), 3.75 (s, 3H), 3.5 (m, 1H), 3.3 (t, J=8 Hz, 1H), 2.8-2.6 (m, 2H) 1.3 (s, 9H). Anal. calcd. for C$_{23}$H$_{30}$FN$_3$O$_4$S: C, 59.59; H, 6.52; N, 9.06; found C, 59.61; H, 6.55; N, 8.89. FAB-HRMS calcd. 464.2019; found 464.2023 (MH$^+$).

Compound 37: 1-(Fluoromethylsulfonylamino)-3-[2-(4-methoxyphenyl)ethyl]-4-[(2,3dihydro-benzo[b][1,4]dioxin-6-yl)]-2-imidazolidinone: $^1$H NMR (DMSO-d$_6$) δ 10.2 (s, 1H), 7.05 (d, J=7.8 Hz, 2H), 6.9 (d, J=7.8 Hz 1H), 6.85 (m, 4H), 5.55 (m, 1H), 5.35 (m, 1H), 4.55 (t, J=7 Hz, 1H), 4.25 (s, 4H), 3.8 (t, J=7 Hz, 1H), 3.7 (s, 3H), 3.5 (m, 2H), 3.2 (t, J=7 Hz, 1H), 2.8-2.55 (m, 2H). Anal. calcd. for C$_{21}$H$_{24}$FN$_3$O$_6$S: C, 54.18; H, 5.20; N, 9.03; found C, 54.53; H, 5.24; N, 8.78. FAB-HRMS calcd. 466.1448; found 466.1458 (MH$^+$).

Compound 38: 1-(2,2,2-Trifluoroethanesulfonylamino)-4-[4-(tert-butyl)phenyl]-3-[2-(4-methoxyphenyl)ethyl]-2-imidazolidinone. $^1$H NMR (CDCl$_3$) δ 8.04 (s, 1H), 7.44 (d, J=8.1 Hz, 2H), 7.22 (d, J=8.1 Hz, 2H), 7.08 (d, J=8.4 Hz, 2H), 6.85 (d, J=8.1 Hz, 2H), 4.54 (t, J=8.7 Hz, 1H), 4.04 (m, 3H), 3.79 (s, 3H), 3.74 (m, 1H), 3.40 (t, J=8.4 Hz, 1H), 2.99 (m, 1H), 2.70 (m, 2H), 1.36 (s, 9H). MS m/z (ESI, positive): 514 (MH$^+$), 536 [M+Na]$^+$, (ESI negative): 512 [M−H]$^−$.

Compound 39: 1-(Chloromethylsulfonylamino)-3-[2-(4-methoxyphenyl)ethyl]-4-(4-tert-butyl-phenyl)-2-imidazolidinone: $^1$H NMR (CDCl$_3$) δ 7.45 (d, J=7.8 Hz, 2H), 7.2 (d, J=7.8 Hz, 2H), 7.1 (s, 1H), 7.05 (d, J=7.8 Hz, 2H), 6.85 (d, J=7.8 Hz, 2H), 4.65 (m, 2H), 4.45 (t, J=8 Hz, 1H), 3.95 (t, J=8 Hz, 1H), 3.8 (s, 3H), 3.7 (m, 1H), 3.4 (t, J=8 Hz, 1H), 3.0 (m, 1H), 2.8-2.6 (m, 2H) 1.5 (s, 9H). Anal. calcd. for $C_{23}H_{30}ClN_3O_4S$: C, 57.55; H, 6.30; N, 8.75; found C, 57.71; H, 6.13; N, 8.50. FAB-HRMS calcd. 480.1724; found 480.1737 (MH$^+$).

Compound 40: 1-(Cyanomethylsulfonylamino)-3-[2-(4-methoxyphenyl)ethyl]-4-[(2,3-dihydro-benzo[b][1,4]dioxin-6-yl)]-2-imidazolidinone: $^1$H NMR (DMSO-d$_6$) δ 10.45 (s, 1H), 7.05 (d, J=7.8 Hz, 2H), 6.9 (m, 5H), 4.75 (d, J=9 Hz, 2H), 4.6 (t, J=7 Hz, 1H), 4.3 (s, 4H), 3.8 (t, J=7 Hz, 1H), 3.7 (s, 3H), 3.45 (m, 1H), 3.2 (t, J=7 Hz, 1H), 2.7 (m, 2H), 2.55 (m, 1H). Anal. calcd. for $C_{22}H_{24}N_4O_6S$. 0.8H$_2$O: C, 54.27; H, 5.29; N, 11.50; found C, 54.45; H, 5.12; N, 11.25. FAB-HRMS calcd. 473.1495; found 473.1501 (MH$^+$).

Compound 41: 1-(Cyanomethylsulfonylamino)-3-[2-(4-methoxyphenyl)ethyl]-4-[(4-methoxy)-phenyl]-2-imidazolidinone. An alternative name for this compound is 1-cyano-N-{4-(4-methoxyphenyl)-3-[2-(4-methoxyphenyl)ethyl]-2-oxoimidazolidin-1-yl}methanesulfonamide. $^1$H NMR (DMSO-d$_6$) δ 10.5 (s, 1H), 7.3 (d, J=7.8 Hz, 2H), 6.9 (m, 4H), 6.8 (d, J=7.8 Hz, 2H), 4.8 (d, J=9 Hz, 2H), 4.6 (t, J=7 Hz, 1H), 3.9 (m, 1H), 3.8 (s, 3H), 3.75 (s, 3H), 3.5 (m, 2H), 3.3 (m, 1H), 2.75 (m, 2H). Anal calcd. for $C_{21}H_{24}N_4O_5S$: C, 56.74; H, 5.44; N, 12.60; found C, 56.91; H, 5.66; N, 12.42. FAB-HRMS calcd. 445.1546; found 445.1562 (MH$^+$).

Compound 42: 1-[(N-3-Pyridinylmethylsulfonyl)amino]-3-[2-(4-methoxyphenyl)ethyl]-4-(4-difluoromethoxyphenyl)-2-imidazolidinone. $^1$H NMR (CDCl$_3$) δ 8.84 (s, 1H), 8.60 (s, 1H), 8.19 (d, J=7.8 Hz, 1H), 8.10 (bs, 1H), 7.48 (m, 1H), 7.29 (d, J=8.4 Hz, 2H), 7.17 (d, J=8.7 Hz, 2H), 7.08 (d, J=8.4 Hz, 2H), 6.84 (d, J=8.4 Hz, 2H), 6.56 (t, J=73.8 Hz, 1H), 4.51 (s, 2H), 4.48 (m, 1H), 4.00 (t, J=8.1 Hz, 1H), 3.74 (s, 3H), 3.72 (m, 1H), 3.43 (t, J=8.1 Hz, 1H), 2.96 (m, 1H), 2.76 (m, 1H), 2.70 (m, 1H). MS 533 (MH$^+$). Anal. Calcd. for $C_{25}H_{26}F_2N_4O_5S$: C, 56.38, H, 4.92; N, 10.52. Found: C, 56.08, H, 4.82; N, 10.28.

Compound 43: 1-[(Phenylmethyl)sulfonylamino]-3-[2-(4-methoxyphenyl)ethyl]-4-(3,4-dimethyl-phenyl)-2-imidazolidinone. $^1$H NMR (CDCl$_3$) δ 7.55 (m, 2H), 7.43 (m, 3H), 7.20 (d, J=7.5 Hz, 1H), 7.12 (d, J=8.1 Hz, 2H), 7.04 (m, 2H), 6.86 (m, 3H), 4.48 (t, J=8.4 Hz, 1H), 4.44 (s, 2H), 3.99 (t, J=8.4 Hz, 1H), 3.80 (m, 1H), 3.72 (s, 3H), 3.36 (t, J=8.4 Hz, 1H), 3.01 (m, 1H), 2.78 (m, 1H), 2.71 (m, 1H), 2.32 (s, 6H). MS 494 (MH$^+$). Anal. Calcd. for $C_{27}H_{31}N_3O_4S$: C, 65.70, H, 6.33; N, 8.51. Found: C, 65.45, H, 6.19; N, 8.38.

Example 4 describes the synthesis of exemplary compounds having Formula XII. 1-[3-(4-methoxyphenyl)propyl]-5-[(4-methoxy)-phenyl]-2-imidazolidinone can be prepared by the procedures described in Examples 1 and 2 herein above by substituting 3-(4-methoxyphenyl)propyl amine for 2-(4-methoxyphenyl)ethyl amine. The skilled practitioner will know how to substitute the appropriate reagents, starting materials and purification methods known to those skilled in the art, in order to prepare additional compounds of the present invention.

EXAMPLE 4

Compound 44: 1-(Sulfamoylamino)-3-[3-(4-methoxyphenyl)propyl]-4-[(4-methoxy)phenyl]-2-imidazolidinone. An alternative name for this compound is 1-(Aminosulfonylamino)-3-[3-(4-methoxyphenyl)propyl]-4-[(4-methoxy)phenyl]-2-imidazolidinone.

5-(4-Methoxy-phenyl)-1-[3-(4-methoxy-phenyl)-propyl]-imidazolidin-2-one and iterations thereof can be prepared by substituting 3-(4-methoxyphenyl)propyl amine into step (b) of Examples 1 or 2 as described herein above. The formulator can, for example, without undue experimentation substitute other 3-(substituted aryl)propyl amines for 3-(4-methoxyphenyl)ethyl amine in order to prepare exemplary analogs encompassed within formula XII, inter alia, 3-(4-tert-butylphenyl)propyl amine and 3-(4-methoxyphenyl)-1-methylpropyl amine.

Preparation of 1-amino-3-[3-(4-methoxyphenyl)propyl]-4-[(4-methoxy)phenyl]-2-imidazolidinone: To a solution of 1-[3-(4-methoxyphenyl)propyl]-5-[(4-methoxy)-phenyl]-2-imidazolidinone (0.6 g, 1.75 mmol) in acetic acid (15 mL) is added dropwise a solution of NaNO$_2$ (0.12 g, 1.8 mmol) in water (1 mL). The mixture is cooled in an ice bath to 5° C. and zinc dust (0.6 g, 9 mmol) is added in portions (starting with 0.5 g addition) over 50 minutes at less than 12° C. The reaction is stirred for 5 minutes and the ice bath is removed. The reaction temperature rises quickly to about 20° C. and the reaction is maintained below about 32° C. with an ice bath. The reaction is stirred for 70 minutes at 20° C. to 27° C. and any unreacted zinc is removed by filtration. The volume of the filtrate is reduced in vacuo then diluted with dichloromethane (15 mL). To the stirred mixture is added concentrated ammonium hydroxide (2 mL), keeping the temperature below about 32° C. with an ice bath. The organic phase is separated, washed with brine, dried (Na$_2$SO$_4$), and concentrated to afford 0.68 g (quantitative yield) of the desired compound as a colorless oil which is used without further purification.

Preparation of 1-(Sulfamoylamino)-3-[3-(4-methoxyphenyl)propyl]-4-[(4-methoxy)phenyl]-2-imidazolidinone: To a solution of chlorosulfonylisocyanate (0.175 mL, 2 mmol) in CH$_2$Cl$_2$ (3 mL) at −30° C. is added dropwise a solution of tert-butanol (150 mg, 2 mmol) in CH$_2$Cl$_2$ (1 mL). This solution is allowed to warm to 0° C. for 3 minutes and then re-cooled to −20° C. 1-Amino-3-[3-(4-methoxyphenyl)propyl]-4-[(4-methoxy)phenyl]-2-imidazolidinone prepared in the above procedure and triethylamine (0.28 mL, 2 mmol) are dissolved in CH$_2$Cl$_2$ (2 mL) and this solution is added to the reaction vessel containing the reactive isocyanate intermediate. The combined ingredients are then allowed to warm to room temperature after which the solvent is removed under reduced pressure and the crude product purified over silica (hexane/EtOAc) to afford 0.67 g of a white powder which is dissolved in CH$_2$Cl$_2$ (3 mL), cooled to 5° C. and trifluoroacetic acid (1 mL) is added. The solution is allowed to warm to room temperature and stir for about 30 minutes after which the solution is concentrated to dryness, re-dissolved in CH$_2$Cl$_2$, washed with saturated aqueous NaHCO$_3$ and concentrated to afford 0.27 g (32% yield) of the desired product. $^1$H NMR (DMSO-d$_6$) δ 8.5 (s, 1H), 7.3 (d, J=7.8 Hz, 1H), 7.05 (d, J=7.8 Hz, 2H), 7.0 (s, 2H), 6.95 (d, J=7.8 Hz, 2H), 6.8 (d, J=7.8 Hz, 2H), 4.7 (t, J=7 Hz, 1H), 3.9 (t, J=6 Hz, 1H), 3.8 (s, 3H), 3.7 (s, 3H), 3.3 (m, 2H), 2.7 (m, 1H), 2.5 (m, 2H), 1.7 (m, 2H). Anal. calcd. for $C_{20}H_{26}N_4O_5S$. 0.8H$_2$O: C, 53.51; H, 6.19; N, 12.48; found C, 53.86; H, 5.98; N, 12.08. FAB-HRMS calcd. 435.1702; found 435.1706 (MH$^+$).

The following are non-limiting examples of compounds having Formula XII.

Compound 45: 1-(Methylsulfonylamino)-3-(3-phenylpropyl)-4-(4-cyclopropylphenyl)-2-imidazolidinone: $^1$H NMR (CDCl$_3$) δ 7.23 (m, 6H), 7.11 (m, 3H), 4.56 (t, J=8.1 Hz, 1H), 3.94 (t, J=8.1 Hz, 1H), 3.46 (m, 2H), 3.17 (s, 3H), 2.86 (m, 1H), 2.56 (t, J=7.8 Hz, 2H), 1.93 (m, 1H), 1.77 (m, 2H), 1.03 (m, 2H), 0.75 (m, 2H). MS m/z (ESI, positive): 414 (MH$^+$), 436 [M+Na]$^+$, (ESI negative): 412 [M−H]$^-$. Anal Calcd for $C_{22}H_{27}N_3O_3S$: C, 63.90; H, 6.58; N, 10.16. Found: C, 64.07; H, 6.71; N, 10.22.

Compound 46: 1-(Methylsulfonylamino)-3-(3-phenylpropyl)-4-(4-methoxyphenyl)-2-imidazolidinone: $^1$H-NMR (CDCl$_3$) δ 7.20 (m, 8H), 6.93 (d, J=8.4 Hz, 2H), 4.55 (t, J=8.1 Hz, 1H), 3.94 (t, J=8.4 Hz, 1H), 3.85 (s, 3H), 3.46 (m, 2H), 3.17 (s, 3H), 2.86 (m, 1H), 2.56 (t, J=7.8 Hz, 1H), 1.75 (m, 2H). (MS) 404 (MH$^+$), 402 (M−H$^−$). Anal. Calcd for $C_{20}H_{25}N_3O_4S$: C, 59.53; H, 6.25; N, 10.41. Found: C, 59.90; H, 6.39; N, 10.50.

Compound 47: 1-(Methylsulfonylamino)-3-(3-phenylpropyl)-4-[4-(tert-butyl)phenyl]-2-imidazolidinone: $^1$H NMR (CDCl$_3$) δ 7.44 (d, J=8.4 Hz, 2H), 7.26 (m, 5H), 7.13 (m, 2H), 6.90 (s, 1H), 4.59 (t, J=8.1 Hz, 1H), 3.94 (t, J=8.4 Hz, 1H), 3.48 (m, 2H), 3.18 (s, 3H), 2.90 (m, 1H), 2.58 (t, J=7.8 Hz, 2H), 1.76 (m, 2H), 1.37 (s, 9H). MS m/z (ESI, positive): 430 (MH$^+$). Anal calcd for $C_{23}H_{31}N_3O_3S$: C, 64.31; H, 7.27; N, 9.78. Found: C, 64.52; H, 7.56; N, 9.90.

Compound 48: 1-(Methylsulfonylamino)-3-[3-(4-methoxyphenyl)propyl]-4-[(4-cyclopropyl)-phenyl]-2-imidazolidinone: $^1$H NMR (DMSO-d$_6$) δ 9.45 (s, 1H), 7.25 (d, J=7.8 Hz, 2H), 7.1 (d, J=7.8 Hz, 2H), 7.0 (d, J=7.8 Hz, 2H), 6.8 (d, J=7.8 Hz, 2H), 4.65 (t, J=6 Hz, 1H), 3.85 (t, J=6 Hz, 1H), 3.7 (s, 3H), 3.25 (m, 2H), 3.0 (s, 3H), 2.65 (m, 1H), 2.4 (m, 2H), 1.95 (m, 1H), 1.6 (m, 2H), 0.9 (m, 2H), 0.7 (m, 2H). Anal. calcd. for $C_{23}H_{29}N_3O_4S \cdot 0.25H_2O$: C, 61.65; H, 6.69; N, 9.37; found C, 61.52; H, 6.49; N, 9.35. FAB-HRMS calcd. 444.1957; found 444.1955 (MH$^+$).

Compound 49: 1-(Methylsulfonylamino)-3-[3-(4-methoxyphenyl)propyl]-4-[(4-methoxy)-phenyl]-2-imidazolidinone: $^1$H NMR (DMSO-d$_6$) δ 9.5 (s, 1H), 7.3 (d, J=7.8 Hz, 2H), 7.05 (d, J=7.8 Hz, 2H), 6.95 (d, J=7.8 Hz, 2H), 6.8 (d, J=7.8 Hz, 2H), 4.65 (t, J=8.1 Hz, 1H), 3.85 (t, J=8.1 Hz, 1H), 3.8 (s, 3H), 3.7, (s, 3H), 3.25 (m, 2H), 3.05 (s, 3H), 2.65 (m, 1H), 2.4 (m, 2H), 1.6 (m, 2H). Anal. calcd. for $C_{21}H_{27}N_3O_5S \cdot 0.25H_2O$: C, 57.58; H, 6.32; N, 9.59; found C, 57.73; H, 6.26; N, 9.54. FAB-HRMS calcd. 434.1750; found 434.1763. (MH$^+$).

Compound 50: 1-(Methylsulfonylamino)-3-[3-(4-methoxyphenyl)propyl]-4-[(4-tert-butyl)phenyl]-2-imidazolidinone: $^1$H NMR (DMSO-d$_6$) δ 10.2 (s, 1H) 7.5 (d, J=7.8 Hz, 2H), 7.3 (d, J=7.8 Hz, 2H), 7.05 (d, J=7.8 Hz, 2H), 6.8 (d, J=7.8 Hz, 2H), 5.5 (m, 1H), 5.3 (m, 1H), 4.6 (t, J=8 Hz, 1H), 3.8 (t, J=8 Hz, 1H), 3.7 (s, 3H), 3.5 (m, 1H), 3.3 (t, J=8 Hz, 1H), 2.8-2.6 (m, 2H) 1.3 (s, 9H). FAB-HRMS calcd. for $C_{24}H_{33}N_4O_3S$: 460.2270; found 460.2275 (MH$^+$).

Example 5 describes the synthesis of exemplary compounds having Formula XIII. The skilled practitioner will know how to substitute the appropriate reagents, starting materials and purification methods known to those skilled in the art, in order to prepare additional compounds of the present invention.

EXAMPLE 5

Compound 51: 1-[[2-(Cyclopropylamino)-2-oxoethyl]sulfonylamino]-3-[2-(4-methoxyphenyl)ethyl]-4-(4-cyclopropylphenyl)-2-imidazolidinone Preparation of 9H-fluoren-9-ylmethyl chlorosulfonylacetate. A solution of 9-(fluorenyl)methyl alcohol (4.8 g, 0.0245 mol) in dichloromethane (65 mL) is added slowly over 11 minutes to a solution of chlorosulfonylacetyl chloride (2.6 mL, 0.0245 mol) in dichloromethane (24 mL) at −23° C. to −19° C. The reaction is stirred in an ice bath for 6.5 hours, then stirred at ambient temperature for 20 minutes, and concentrated. The residue is dissolved in diethyl ether (13 mL) and slowly diluted with hexanes (26 mL). The mixture is stirred for 30 minutes and the solid which forms is collected by filtration to afford 5.96 g (72% yield) of the desired compound. $^1$H NMR (CDCl$_3$) δ 7.81 (d, J=7.5 Hz, 2H), 7.65 (d, J=7.5 Hz, 2H), 7.47 (m, 2H), 7.37 (m, 2H), 4.67 (d, J=6.6 Hz, 2H), 4.64 (s, 2H), 4.31 (t, J=12.9 Hz, 1H).

Preparation of 1-[[2-(9H-fluoren-9-ylmethoxy)-2-oxoethyl]sulfonylamino]-3-[2-(4-methoxyphenyl)ethyl]-4-(4-cyclopropylphenyl)-2-imidazolidinone. To a solution of 1-amino-3-[2-(4-methoxyphenyl)ethyl]-4-(4-cyclopropylphenyl)-2-imidazolidinone p-toluenesulfonic acid salt (2.61 g, 0.0050 mol), dichloromethane (12 mL), and N-methylmorpholine (1.53 mL, 0.014 mol) is added a solution of 9H-fluoren-9-ylmethyl chlorosulfonylacetate, 14, (1.76 g, 0.0052 mol) in dichloromethane (7 mL) slowly over 7 minutes at 15° C. to 20° C. The reaction is stirred at ambient temperature for 45 minutes, and then washed twice with 0.1 N HCl and water. The organic phase is dried (sodium sulfate) and concentrated to a foamy solid. The residue is purified over silica (0%-50% ethyl acetate/hexanes gradient) to afford 2.1 g of the desired compound. $^1$H NMR (CDCl$_3$) δ 7.81 (d, J=7.5 Hz, 2H), 7.69 (d, J=7.5 Hz, 2H), 7.45 (m, 2H), 7.36 (m, 2H), 7.27 (s, 1H), 7.17 (m, 2H), 7.10 (m, 2H), 7.02 (m, 2H), 6.82 (m, 2H), 4.63 (m, 2H), 4.45 (t, J=8.4 Hz, 1H), 4.35 (m, 3H), 3.94 (t, J=8.4 Hz, 1H), 3.78 (s, 3H), 3.65 (m, 1H), 3.38 (t, J=8.1 Hz, 1H), 2.92 (m, 1H), 2.74 (m, 1H), 2.64 (m, 1H), 1.94 (m, 1H), 1.03 (m, 2H), 0.74 (m, 2H). MS 652 (MH$^+$). Anal. calcd. for $C_{37}H_{37}N_3O_6S \cdot \frac{3}{4}H_2O$: C, 66.80; H, 5.83; N, 6.32. Found: C, 66.78; H, 5.72; N, 6.30.

Preparation of [[[4-(4-cyclopropylphenyl)-3-[2-(4-methoxyphenyl)ethyl]-2-oxo-imidazolidin-1-yl]amino]sulfonyl]acetic acid. To a solution of 1-[[[(9H-fluoren-9-ylmethyloxy)carbonylmethyl]sulfonylamino]-3-[2-(4-methoxyphenyl)ethyl]-4-(4-cyclopropylphenyl)-2-imidazolidinone (2.0 g, 0.0031 mol) in DMF (15 mL) at room temperature is added 1,8-diazabycyclo[5.4.0]undec-7-ene (0.35 mL). The reaction is stirred for approximately one hour, diluted with ice-cold 0.1 N HCl and extracted with ethyl acetate. The organic phase is washed with brine, dried (sodium sulfate) and concentrated. The residue is warmed in approximately 20 mL of ether and diluted slowly with approximately 20 mL of hexanes. The liquid is decanted and the resulting material is dried under vacuum to afford 1.08 g of the desired compound. $^1$H NMR (CDCl$_3$) δ 8.03 (bs, 1H), 7.19 (d, J=8.4 Hz, 2H), 7.11 (d, J=8.1 Hz, 2H), 7.05 (m, 2H), 6.84 (m, 2H), 4.51 (t, J=8.4 Hz, 1H), 4.30 (s, 2H), 4.01 (t, J=8.7 Hz, 1H), 3.81 (s, 3H), 3.66 (m, 1H), 3.51 (m, 1H), 2.95 (m, 1H), 2.64 (m, 1H), 1.93 (m, 1H), 1.02 (m, 2H), 0.74 (m, 2H). MS 652 (MH$^+$). Anal. calcd. for $C_{23}H_{27}N_3O_6S \cdot \frac{1}{4}C_4H_{10}O$: C, 58.58; H, 6.04; N, 8.54. Found: C, 58.37; H, 6.01; N, 8.35.

Preparation of 1-{[2-(cyclopropylamino)-2-oxoethyl]sulfonylamino}-3-[2-(4-methoxyphenyl)ethyl]-4-(4-cyclopropylphenyl)-2-imidazolidinone. To a solution of [[4-(4-cyclopropylphenyl)-3-[2-(4-methoxyphenyl)ethyl]-2-oxo-imidazolidin-1-yl]-amino]sulfonyl]acetic acid (459 mg, 0.97 mmol) in dichloromethane (20 mL) at 10° C. is added benzotriazol-1-yloxytripyrrolidino-phosphonium hexafluorophosphate (PyBOP) (1053 mg, 2.0 mmol), Hunig's base (0.51 mL, 2.9 mmol), and cyclopropylamine (0.20 mL, 2.9 mmol). The reaction is stirred at ambient temperature for one hour, and is washed with 1.0 N HCl, water, and brine. The organic phase is dried (sodium sulfate) and concentrated to a solid. The residue is purified over a C18 reverse phase chromatographic column (eluting with 15%-95% acetonitrile/water (0.1% TFA)) to afford 289 mg of the desired compound. $^1$H NMR (CDCl$_3$) δ 8.43 (d, J=3.6 Hz, 1H), 7.12 (m, 5H), 7.06 (m, 2H), 6.83 (m, 2H), 4.49 (t, J=8.4 Hz, 1H), 4.00 (m, 3H), 3.80 (s, 3H), 3.68 (m, 1H), 3.42 (m, 1H), 3.42 (m, 1H), 2.95 (m, 1H), 2.86 (m, 1H), 2.72 (m, 1H), 2.65 (m, 1H), 1.93 (m, 1H), 1.01 (m, 2H), 0.83 (m, 2H), 0.74 (m, 2H), 0.64 (m, 2H). MS 513 (MH$^+$). Anal. calcd. for $C_{26}H_{32}N_4O_5S \cdot \frac{1}{2}H_2O$: C, 59.87; H, 6.38; N, 10.74. Found: C, 59.62; H, 6.14; N, 10.49.

The following are non-limiting examples of compounds having formula XIII.

Compound 52: 1-[(2-Amino-2-oxoethyl)sulfonylamino]-3-[2-(4-methoxyphenyl)ethyl]-4-(4-cyclopropylphenyl)-2-imidazolidinone: $^1$H NMR (CDCl$_3$) δ 8.86 (d, J=12.9 Hz, 2H), 7.19 (d, J=8.1 Hz, 2H), 7.11 (d, J=8.4 Hz, 2H), 7.07 (m, 2H), 6.88 (s, 1H), 6.83 (m, 2H), 4.50 (t, J=8.4 Hz, 1H), 4.11 (m, 2H), 3.99 (t, J=8.4 Hz, 1H), 3.80 (s, 3H), 3.66 (m, 1H), 3.48 (m, 1H), 2.94 (m, 1H), 2.75 (m, 1H), 2.64 (m, 1H), 1.94 (m, 1H), 1.02 (m, 2H), 0.74 (m, 2H). MS 473 (MH$^+$). FAB-HRMS: anal. calcd for C$_{23}$H$_{28}$N$_4$O$_5$S: 473.1859. Found: 473.1875.

Compound 53: 2-(N-(4-(4-cyclopropylphenyl)-3-(4-methoxyphenethyl)-2-oxoimidazolidin-1-yl)sulfamoyl)-N-(3-hydroxy-3-methylbutan-2-yl)acetamide: $^1$H NMR (CDCl$_3$) δ 9.63 (d, J=4.5 Hz, 1H), 8.16 (d, J=8.7 Hz, 1H), 7.26 (d, J=8.1 Hz, 2H), 7.14 (J=8.4 Hz, 2H), 7.04 (d, J=8.4 Hz, 2H), 6.83 (d, J=8.7 Hz, 2H), 4.65 (t, J=8.1 Hz, 1H), 4.36 (d, J=5.7 Hz, 1H), 4.03 (m, 2H), 3.89 (m, 1H), 3.77 (m, 1H), 3.72 (s, 3H), 3.48 (m, 1H), 3.33 (m, 2H), 2.73 (m, 2H), 2.57 (m, 1H), 1.95 (m, 1H), 1.82 (m, 1H), 1.11 (s, 3H), 1.08 (s, 3H), 1.07 (s, 1.5H), 1.05 (s, 1.5H), 0.97 (m, 2H), 0.70 (m, 2H). MS 559 (MH$^+$). FAB-HRMS: anal. calcd for C$_{28}$H$_{38}$N$_4$O$_6$S: 559.2590. Found: 559.2593.

Compound 54: 1-[[2-(Dimethylamino)-2-oxoethyl]sulfonylamino]-3-[2-(4-methoxyphenyl)ethyl]-4-(4-cyclopropylphenyl)-2-imidazolidinone: $^1$H NMR (CDCl$_3$) δ 8.21 (s, 1H), 7.16 (d, J=8.1 Hz, 2H), 7.10 (d, J=8.4 Hz, 2H), 7.03 (d, J=8.4 Hz, 2H), 6.83 (d, J=8.4 Hz, 2H), 4.44 (m, 3H), 3.98 (t, J=8.4 Hz, 1H), 3.81 (s, 3H), 3.61 (m, 1H), 3.48 (t, J=8.1 Hz, 1H), 3.07 (s, 3H), 3.06 (s, 3H), 2.90 (m, 1H), 2.70 (m, 1H), 2.64 (m, 1H), 1.93 (m, 1H), 1.02 (m, 2H), 0.73 (m, 2H). MS 501 (MH$^+$). FAB-HRMS: anal. calcd for C$_{25}$H$_{32}$N$_4$O$_5$S: 501.2172. Found: 501.2175.

Compound 55: 1-[[2-(Dimethylamino)-2-oxoethyl]sulfonylamino]-3-[2-(4-methoxyphenyl)-ethyl]-4-(4-methoxyphenyl)-2-imidazolidinone: $^1$H NMR (CDCl$_3$) δ 8.21 (s, 1H), 7.21 (m, 2H), 7.02 (m, 2H), 6 93 (m, 2H), 6 83 (m, 2H), 4.43 (m, 2H), 3.98 (t, J=8.7 Hz, 1H), 3.85 (s, 3H), 3.81 (s, 3H), 3.61 (m, 1H), 3.49 (t, J=8.4 Hz, 1H), 3.07 (s, 6H), 2.90 (m, 1H), 2.73 (m, 1H), 2.63 (m, 1H). MS 491 (MH$^+$). Anal. Calcd. For C$_{23}$H$_{30}$N$_4$O$_6$S·½H$_2$O: C, 55.30; H, 6.25; N, 11.21. Found: C, 55.11; H, 6.13; N, 11.12.

Compound 56: 1-[[2-(Cyclopropylamino)-2-oxoethyl]sulfonylamino]-3-[2-(4-methoxyphenyl)-ethyl]-4-(4-methoxyphenyl)-2-imidazolidinone: $^1$H NMR (CDCl$_3$) δ 8.81 (d, J=3.6 Hz, 1H), 7.63 (s, 1H), 7.21 (, J=8.4 Hz, 2H), 7.04 (d, J=8.4 Hz, 2H), 6.93 (d, J=8.4 Hz, 2H), 6.83 (d, J=8.4 Hz, 2H), 4.50 (t, J=8.7 Hz, 1H), 4.07 (s, 2H), 4.00 (t, J=8.4 Hz, 1H), 3.84 (s, 3H), 3.79 (s, 3H), 3.64 (m, 1H), 3.47 (m, 1H), 2.94 (m, 1H), 2.87 (m, 1H), 2.71 (m, 1H), 2.64 (m, 1H). MS 503 (MH$^+$). FAB-HRMS: anal. calcd for C$_{24}$H$_{30}$N$_4$O$_6$S: 503.1964. Found: 503.1956.

Compound 57: 1-[[2-[(Cyclopropylmethyl)amino]-2-oxoethyl]sulfonylamino]-3-[2-(4-methoxy-phenyl)ethyl]-4-(4-methoxyphenyl)-2-imidazolidinone: $^1$H NMR (CDCl$_3$) δ 8.33 (m, 1H), 7.22 (m, 2H), 7.07 (m, 2H), 6.95 (m, 2H), 6.85 (m, 2H), 4.50 (t, J=8.4 Hz, 1H), 4.07 (s, 2H), 4.00 (t, J=8.4 Hz, 1H), 3.86 (s, 3H), 3.80 (s, 3H), 3.68 (m, 1H), 3.45 (m, 1H), 3.24 (m, 2H), 2.97 (m, 1H), 2.74 (m, 1H), 2.68 (m, 1H), 1.08 (m, 1H), 0.57 (m, 2H), 0.30 (m, 2H). MS 517 (MH$^+$). Anal. calcd. for C$_{25}$H$_{32}$N$_4$O$_6$S·¾H$_2$O: C, 56.64; H, 6.37; N, 10.57. Found: C, 56.77; H, 6.07; N, 10.49.

Compound 58: N-(cyclopropylmethyl)-2-(N-(4-(4-cyclopropylphenyl)-3-(4-methoxyphenethyl)-2-oxoimidazolidin-1-yl)sulfamoyl)acetamide. $^1$H NMR (CDCl$_3$) δ 8.24 (t, J=4.8 Hz, 1H), 7.16 (d, J=8.4 Hz, 2H), 7.12 (d, J=8.4 Hz, 2H), 7.07 (m, 2H), 6.98 (s, 1H), 6.84 (m, 2H), 4.50 (t, J=8.4 Hz, 1H), 4.05 (m, 2H), 4.00 (t, J=8.4 Hz, 1H), 3.81 (s, 3H), 3.71 (m, 1H), 3.43 (m, 1H), 3.24 (m, 2H), 2.97 (m, 1H), 2.74 (m, 1H), 2.67 (m, 1H), 1.94 (m, 1H), 1.05 (m, 3H), 0.74 (m, 2H), 0.56 (m, 2H), 0.30 (m, 2H). MS 527 (MH$^+$). Anal. calcd. for C$_{27}$H$_{34}$N$_4$O$_5$S·½H$_2$O: C, 60.54; H, 6.59; N, 10.75. Found: C, 57.69; H, 6.19 N, 10.46.

Compound 59: 1-[[2-(Cyclobutylamino)-2-oxoethyl]sulfonylamino]-3-[2-(4-methoxyphenyl)-ethyl]-4-(4-methoxyphenyl)-2-imidazolidinone: $^1$H NMR (CDCl$_3$) δ 8.47 (d, J=7.2 Hz, 1H), 7.22 (d, J=8.7 Hz, 2H), 7.08 (d, J=8.7 Hz, 2H), 6.98 (s, 1H), 6.95 (d, J=8.7 Hz, 2H), 6.84 (d, J=8.4 Hz, 2H), 4.48 (m, 2H), 4.01 (m, 3H), 3.86 (s, 3H), 3.80 (s, 3H), 3.71 (m, 1H), 3.43 (m, 1H), 2.98 (m, 1H), 2.74 (m, 1H), 2.65 (m, 1H), 2.37 (m, 2H), 2.03 (m, 2H), 1.79 (m, 2H). MS 517 (MH$^+$). Anal. calcd. for C$_{27}$H$_{34}$N$_4$O$_5$S·H$_2$O: C, 56.17; H, 6.41; N, 10.48. Found: C, 56.18; H, 6.07 N, 10.33.

Compound 60: 1-[[2-[(Bis(methoxyethyl)amino)]-2-oxoethyl]sulfonylamino]-3-[2-(4-methoxy-phenyl)ethyl]-4-(4-cyclopropylphenyl)-2-imidazolidinone: $^1$H NMR (CDCl$_3$) δ 8.13 (bs, 1H), 7.16 (m, 2H), 7.08 (m, 2H), 7.03 (m, 2H), 6.83 (m, 2H), 4.68 (d, J=15.3 Hz, 1H), 4.59 (d, J=15.3 Hz, 1H), 4.41 (t, J=8.4 Hz, 1H), 3.96 (t, J=8.4 Hz, 1H), 3.61 (s, 3H), 3.67-3.53 (m, 9H), 3.47 (m, 1H), 3.38 (s, 3H), 3.38 (s, 3H), 2.90 (m, 1H), 2.73 (m, 1H), 2.64 (m, 1H), 1.93 (m, 1H), 1.02 (m, 2H), 0.73 (m, 2H). MS 589 (MH$^+$). Anal. calcd. for C$_{29}$H$_{40}$N$_4$O$_7$S: C, 59.16; H, 6.85; N, 9.52. Found: C, 58.78; H, 6.72; N, 9.55.

The following are non-limiting examples of compounds having Formula XIV. Exemplary compounds having Formula XIV can be prepared according to the procedures outlined herein above in Example 3 by adjusting the conditions in a manner known to the artisan of ordinary skill.

Compound 61: 1-[(Methylsulfonylmethyl)sulfonyl]amino-3-[2-(4-methoxyphenyl)ethyl]-4-(4-Cyclopropylphenyl)-2-imidazolidinone. $^1$H NMR (CDCl$_3$) δ 8.11 (s, 1H), 7.18 (d, J=8.1 Hz, 2H), 7.10 (d, J=8.1 Hz, 2H), 7.05 (d, J=8.4 Hz, 2H), 6.84 (d, J=8.7 Hz, 2H), 4.95 (m, 2H), 4.49 (t, J=8.4 Hz, 1H), 3.96 (t, J=8.4 Hz, 1H), 3.81 (s, 3H), 3.70 (m, 1H), 3.41 (t, J=8.1 Hz, 1H), 3.26 (s, 3H), 2.93 (m, 1H), 2.65 (m, 2H), 1.93 (m, 1H), 1.02 (m, 2H), 0.74 (m, 2H). MS 508 (MH$^+$), 506 (MH$^-$). Anal. Calcd for C$_{23}$H$_{29}$N$_3$O$_6$S$_2$: C, 54.42; H, 5.76; N, 8.28. Found: C, 53.99: h, 5.74; N, 7.97.

Example 6 describes the synthesis of exemplary compounds having formula XV. The skilled practitioner will know how to substitute the appropriate reagents, starting materials and purification methods known to those skilled in the art, in order to prepare additional compounds of the present invention.

EXAMPLE 6

Compound 62: 1-[(Pyridin-3-yl)sulfonylamino]-3-[2-(4-methoxyphenyl)ethyl]-4-(4-methoxyphenyl)-2-imidazolidinone 1-[(Pyridin-3-yl)sulfonylamino]-3-[2-(4-methoxyphenyl)ethyl]-4-(4-methoxyphenyl)-2-imidazolidinone: 1-Amino-3-[2-(4-methoxyphenyl)ethyl]-4-(4-methoxyphenyl)-2-imidazolidinone toluenesulfonic acid (0.3 g, 0.58 mmol) is stirred in dichloromethane (6 mL) and 3-pyridylsulfonylchloride HCl (135 mg, 0.63 mmol) is added followed by 4-methylmorpholine (0.2 mL). The mixture is heated in a microwave oven at 80° C. for 25 minutes. The mixture is evaporated and purified over silica (hexane/ethylacetate) to give the afford 0.12 g (41% yield) of the desired product as a white solid. $^1$H NMR (DMSO-d$_6$) δ 10.3 (s, 1H), 9.0 (s, 1H), 8.9 (d, J=6 Hz, 1H), 8.2 (d, J=7.8 Hz, 1H), 7.65 (m, 1H), 7.2 (d, J=7.8 Hz, 2H), 7.05, (d, J=7.8 Hz, 2H), 6.95 (d, J=7.8 Hz, 2H), 6.8 (d, J=7.8 Hz, 2H), 4.5 (t, J=7 Hz, 1H), 3.8 (s, 3H), 3.75 (s, 3H), 3.3 (m, 1H), 3.2 (m, 1H), 2.75 (m, 2H), 2.4 (m, 2H). Anal. calcd. for $C_{24}H_{26}N_4O_5S$: C, 59.74; H, 5.43; N, 11.61; found C, 59.60; H, 5.47; N, 11.37. FAB-HRMS calcd. 483.1702; found 483.1720 (MH$^+$).

Compound 63: 1-[(Phenylmethyl)sulfonylamino]-3-[2-(4-methoxyphenyl)ethyl]-4-(4-methoxyphenyl)-2-imidazolidinone. $^1$H NMR (CDCl$_3$) δ 7.55 (m, 2H), 7.42 (m, 3H), 7.21 (d, J=8.4 Hz, 2H), 7.10 (m, 3H), 6.94 (d, J=8.4 Hz, 2H), 6.84 (d, J=8.1 Hz, 2H), 4.47 (m, 3H), 3.97 (t, J=8.3 Hz, 1H), 3.86 (s, 3H), 3.72 (m, 4H), 3.36 (t, J=8.3 Hz, 1H), 2.99 (m, 1H), 2.76 (m, 1H), 2.68 (m, 1H). (MS) 496 (MH$^+$), 494 (M−H$^−$). Anal. Calcd for $C_{26}H_{29}N_3O_5S$: C, 63.01; H, 5.90; N, 8.48. Found: C, 62.57; H, 5.82; N, 8.14.

Compound 64: 1-[(Pyridin-3-yl)methanesulfonyl]amino-3-[(4-methoxyphenyl)ethyl]-4-(4-cyclopropylphenyl)-imidazolidin-2-one: $^1$H-NMR (CDCl$_3$) δ: 8.78 (s, 1H), 8.54 (d, J=7.8 Hz, 1H), 7.94 (d, J=7.8 Hz, 1H), 7.32 (m, 1H), 7.17 (m, 2H), 7.09 (t, J=7.8 Hz, 4H), 6.82 (d, J=8.7 Hz, 2H), 4.48 (m, 3H), 3.98 (t, J=8.4 Hz, 1H), 3.74 (m, 4H), 3.39 (t, J=8.4 Hz, 1H), 2.97 (m, 1H), 2.72 (m, 2H), 1.93 (m, 1H), 1.03 (m, 2H), 0.74 (m, 2H). MS m/z (ESI, positive): 507 [M+H]$^+$. Anal calcd for $C_{27}H_{30}N_4O_4S$: C, 64.01; H, 5.97; N, 11.06. Found: C, 63.82; H, 5.70; N, 11.24.

Compound 65: 1-[(Pyridin-3-yl)methylsulfonyl]amino-3-[(4-methoxyphenyl)ethyl]-4-(4-methylphenyl)-2-imidazolidinone: $^1$H NMR (CDCl$_3$) δ 8.80 (s, 1H), 8.48 (d, J=4.8 Hz, 1H), 7.92 (d, J=8.1 Hz, 1H), 7.19 (m, 6H), 7.06 (d, J=7.8 Hz, 2H), 6.81 (d, J=8.1 Hz, 2H), 4.49 (m, 2H), 3.99 (t, J=8.1 Hz, 1H), 3.74 (m, 4H), 3.42 (t, J=8.4 Hz, 1H), 2.95 (m, 1H), 2.76 (m, 1H), 2.66 (m, 1H), 2.37 (s, 3H). MS 481 (MH$^+$), 479 (M−H$^−$). Anal. Calcd for $C_{25}H_{28}N_4O_4S$: C, 62.48; H, 5.87; N, 11.66. Found: C, 62.59; H, 6.03; N, 11.54.

Compound 66: 1-[(Pyridin-3-yl)methylsulfonyl]amino-3-[2-(4-methoxyphenyl)ethyl]-4-(4-methoxyphenyl)-2-imidazolidinone. $^1$H NMR (CDCl$_3$) δ 8.79 (s, 1H), 8.49 (d, J=4.2 Hz, 1H), 7.92 (d, J=7.8 Hz, 1H), 7.28 (m, 1H), 7.19 (dd, J=2.1, 8.7 Hz, 2H), 7.05 (dd, J=2.1, 8.4 Hz, 6.90 (dd, J=2.1, 8.7 Hz, 2H), 6.80 (dd, J=2.1, 8.7 Hz, 2H), 4.47 (m, 3H), 3.97 (t, J=8.4 Hz, 1H), 3.82 (ss, J=2.1 Hz, 3H), 3.69 (m, 4H), 3.40 (t, J=8.4 Hz, 1H), 2.93 (m, 1H), 2.67 (m, 2H). (MS) 497 (MH$^+$), 495 (M−H$^−$). Anal. Calcd for $C_{25}H_{28}N_4O_5S$: C, 60.47; H, 5.68; N, 11.28. Found: C, 60.59; H, 5.83; N, 11.20.

Example 7 describes the synthesis of exemplary compounds of the present invention wherein R$^3$ is —SO$_2$[C(R$^{5a}$R$^{5b}$)]$_j$R$^4$. The skilled practitioner will know how to substitute the appropriate reagents, starting materials and purification methods known to those skilled in the art, in order to prepare additional compounds of the present invention.

EXAMPLE 7

Compound 67: 1-[(N-methyl-N-benzylsulfonyl)amino]-3-[2-(4-methoxy-phenyl)ethyl]-4-(3,4-dimethylphenyl)-2-imidazolidinone Preparation of 1-[(N-methyl-N-benzylsulfonyl)amino]-3-[2-(4-methoxy-phenyl)ethyl]-4-(3,4-dimethylphenyl)-2-imidazolidinone. A solution of 1-[(N-benzylsulfonyl)amino]-3-[2-(4-methoxyphenyl)ethyl]-4-(3,4-dimethylphenyl)-2-imidazolidinone (500 mg, 1.0 mmol) in dry DMF (5.5 mL) is cooled in an ice bath and 60% NaH in mineral oil (52 mg, 1.3 mmol) is added. The reaction is stirred cold for 15 minutes and methyl iodide (0.082 mL, 1.3 mmol) is added. The ice bath is removed and the reaction is stirred for 30 minutes. The reaction is diluted with EtOAc, and washed with water and brine. The organic phase is dried (Na$_2$SO$_4$) and concentrated. The residue is purified over silica (0% to 60% EtOAc/hexanes gradient) to afford 253 mg of the desired product. $^1$H NMR (CDCl$_3$) δ 7.61 (m, 2H), 7.42 (m, 3H), 7.14 (d, J=8.1 Hz, 1H), 7.10 (d, J=8.1 Hz, 3H), 7.01 (bs, 1H), 6.85 (d, J=8.7 Hz, 2H), 4.76-4.30 (m, 3H), 3.95 (m, 0.5H), 3.84-3.66 (m, 4H), 3.29 (m, 0.5H), 3.09 (m, 3H), 2.97 (m, 1H), 2.78 (m, 1H), 2.72 (m, 1H), 2.31 (s, 6H). MS 508 (MH$^+$). Anal. Calcd. For $C_{28}H_{33}N_3O_4S$: C, 66.25; H, 6.55; N, 8.28. Found: C, 66.26; H, 6.44; N, 8.21.

The following are non-limiting examples of compounds of the present invention wherein R$^3$ is —SO$_2$[C(R$^{5a}$R$^{5b}$)]$_j$R$^4$.

Compound 68: 1-[(N-Methoxyethyl-N-methylsulfonyl)amino]-3-[2-(4-methoxyphenyl)ethyl]-4-(4-cyclopropylphenyl)-2-imidazolidinone $^1$H NMR (CDCl$_3$) δ 7.26 (d, J=8.1 Hz, 2H), 7.13 (m, 2H), 7.09 (m, 2H), 6.83 (m, 2H), 4.65 (m, 1H), 3.90 (t, J=9.0 Hz, 0.5H), 3.84 (t, J=8.4 Hz, 0.5H), 3.73 (s, 1.5H), 3.72 (s, 1.5H), 3.67 (m, 2H), 3.48 (m, 2H), 3.40 (m, 2H), 3.28 (s, 1.5H), 3.23 (s, 1.5H), 3.18 (s, 1.5H), 3.04 (s, 1.5H), 2.66 (m, 2H), 2.56 (m, 1H), 1.94 (m, 1H), 0.97 (m, 2H), 0.70 (m, 2H). MS 488 (MH$^+$). FAB-HRMS: anal. calcd for $C_{25}H_{33}N_3O_5S$: 488.2219. Found: 488.2213.

Example 8 describes one method of preparing exemplary compounds having Formula XVII. The skilled practitioner will know how to substitute the appropriate reagents, starting materials and purification methods known to those skilled in the art, in order to prepare additional compounds of the present invention.

EXAMPLE 8

Compound 69: 1-(Acetylamino)-3-[2-(4-methoxyphenyl)ethyl]-4-(3,4-dimethylphenyl)-2-imidazolidinone Preparation of 1-(acetylamino)-3-[2-(4-methoxyphenyl)ethyl]-4-(3,4-dimethyl-phenyl)-2-imidazolidinone: A solution of compound 1-amino-3-[2-(4-methoxy-phenyl)ethyl]-4-(3,4-dimethylphenyl)-2-imidazolidinone hydrochloride (300 mg, 0.80 mmol) in dichloromethane (3.0 mL) is cooled in an ice bath and triethylamine (0.26 mL, 1.8 mmol) is added, followed by dropwise addition of acetyl chloride (0.068 mL, 0.96 mmol). The reaction is stirred in the cold for 45 minutes and washed with 0.1 N aqueous HCl, H$_2$O, 10% aqueous NaHCO$_3$, and brine. The organic phase is dried (Na$_2$SO$_4$) and concentrated under reduced pressure. The residue is purified over silica (2.5% methanol/dichloromethane) to afford 237 mg (78% yield) of the desired compound. $^1$H NMR (CDCl$_3$) δ 9.18 (s, 1H), 7.12 (m, 3H), 7.07 (d, J=8.4 Hz, 2H), 6.83 (d, J=8.4 Hz), 4.41 (t, J=8.4 Hz, 1H), 3.91 (t, J=8.4 Hz, 1H), 3.81 (s, 3H), 3.71 (m, 1H), 3.59 (t, J=8.1 Hz, 1H), 2.94 (m, 1H), 2.80 (m, 1H), 2.67 (m, 2H), 2.29 (s, 6H), 2.09 (s, 3H). MS 382 (MH$^+$). Anal. Calcd. For $C_{22}H_{27}N_3O_3$·¼H$_2$O: C, 68.46, H, 7.18; N, 10.89. Found: C, 68.72, H, 6.97; N, 10.85.

The following are non-limiting examples of compounds having Formula XVII.

Compound 70: {2-Oxo-3-[2-(4-methoxyphenyl)ethyl]-4-(3,4-dimethylphenyl)-imidazolidin-1-yl}-urea: $^1$H NMR (CDCl$_3$) δ 8.87 (bs, 1H), 7.12 (m, 5H), 6.85 (m, 2H), 6.31 (bs, 2H), 4.44 (t, J=8.4 Hz, 1H), 3.92 (t, J=8.4 Hz, 1H), 3.81 (s, 3H), 3.66 (m, 2H), 2.97 (m, 1H), 2.80 (m, 1H), 2.72 (m, 1H), 2.31 (s, 6H). MS 383 (MH$^+$). Anal. Calcd. for $C_{21}H_{26}N_4O_3$·H$_2$O: C, 62.98; H, 7.05; N, 13.99. Found: C, 63.34; H, 6.92; N, 13.66.

Compound 71: 1-(Acetylamino)-3-[2-(4-methoxyphenyl)ethyl]-4-[(4-tert-butyl)benzyl]-2-imidazolidinone: $^1$H NMR (DMSO-d$_6$) δ 9.65 (s, 1H) 7.3 (d, J=7.8 Hz, 2H), 7.15 (d, J=7.8 Hz, 2H), 7.0 (d, J=7.8 Hz, 2H), 6.8 (d, J=7.8 Hz, 2H), 3.75 (m, 2H), 3.7 (s, 3H), 3.45 (m, 1H), 3.25 (m, 1H), 3.2-3.0 (m, 3H), 2.65 (m, 1H), 2.6 (m, 1H), 2.5 (s, 3H), 1.3 (s, 9H).

Anal. calcd. for $C_{25}H_{33}N_3O_5$: C, 70.89; H, 7.85; N, 9.92; found C, 71.12; H, 7.98; N, 9.76. FAB-HRMS calcd. 424.2600; found 424.2615 (MH$^+$).

Compound 72: Cyclopropanecarboxylic acid N-{3-[2-(4-methoxyphenyl)ethyl]-4-(3,4-dimethylphenyl)-2-oxo-imidazolidin-1-yl}-amide: $^1$H NMR (CDCl$_3$) δ 9.00 (s, 1H), 7.11 (m, 4H), 6.83 (m, 3H), 4.43 (t, J=9.0 Hz, 1H), 3.84 (m, 4H), 3.68 (m, 1H), 3.61 (m, 1H), 2.91 (m, 1H), 2.78 (m, 1H), 2.67 (m, 1H), 2.30 (s, 6H), 1.68 (m, 1H), 1.11 (m, 2H), 0.86 (m, 2H). MS 408 (MH$^+$). Anal. Calcd. For $C_{24}H_{29}N_3O_3 \cdot \frac{1}{4}H_2O$: C, 69.96, H, 7.22; N, 10.20. Found: C, 70.14, H, 6.83; N, 9.95.

Compound 73: 1-Cyclopropanecarbonylamino-4-[4-(tert-butyl)phenyl]-3-[2-(4-methoxy-phenyl)ethyl]-2-imidazolidinone: $^1$H-NMR (CDCl$_3$) δ: 7.42 (d, J=8.4 Hz, 2H), 7.33 (d, J=8.1 Hz, 2H), 7.05 (d, J=8.4 Hz, 2H), 6.83 (d, J=8.4 Hz, 2H), 3.87 (t, J=8.4 Hz, 1H), 3.80 (s, 3H), 3.64 (m, 2H), 2.95 (m, 1H), 2.80 (m, 1H), 2.66 (m, 1H), 1.70 (m, 1H), 1.34 (s, 6H), 1.09 (m, 2H), 0.86 (m, 2H). MS m/z (ESI, positive): 436 [M+H]$^+$. Anal Calcd for $C_{26}H_{33}N_3O_3$: C, 71.70; H, 7.64; N, 9.65. Found: C, 71.51; H, 7.84; N, 9.71.

Compound 74: 1-(2-Furanoylamino)-3-[2-(4-Methoxyphenyl)ethyl]-4-(3,4-dimethylphenyl)-2-imidazolidinone: $^1$H NMR (CDCl$_3$) δ 8.96 (bs, 1H), 7.97 (s, 1H), 7.78 (m, 1H), 7.71 (s, 1H), 7.58 (m, 5H), 7.31 (d, J=7.2 Hz, 2H), 7.00 (s, 1H), 4.88 (t, J=8.7 Hz, 1H), 4.41 (t, J=7.8 Hz, 1H), 4.29 (s, 3H), 4.21 (m, 1H), 4.09 (m, 1H), 3.41 (m, 1H), 3.29 (m, 1H), 3.18 (m, 1H), 2.77 (s, 9H). MS 434 (MH$^+$). Anal. Calcd. For $C_{25}H_{27}N_3O_4 \cdot \frac{1}{4}H_2O$: C, 68.56, H, 6.33; N, 9.59. Found: C, 68.74, H, 6.02; N, 9.19.

Compound 75: 1-(Benzoylamino)-3-[2-(4-Methoxyphenyl)ethyl]-4-(3,4-dimethylphenyl)-2-imidazolidinone: $^1$H NMR (CDCl$_3$) δ 9.49 (s, 1H), 7.85 (m, 2H), 7.46 (m, 1H), 7.38 (m, 2H), 7.17 (s, 3H), 7.10 (m, 2H), 6.86 (m, 2H), 4.46 (t, J=8.7 Hz, 1H), 3.94 (t, J=8.4 Hz, 1H), 3.82 (s, 3H), 3.75 (m, 1H), 3.68 (m, 1H), 2.94 (m, 1H), 2.86 (m, 1H), 2.74 (m, 1H), 2.31 (s, 6H). MS 444 (MH$^+$). Anal. Calcd. For $C_{27}H_{29}N_3O_3 \cdot \frac{1}{4}H_2O$: C, 72.38, H, 6.64; N, 9.38. Found: C, 72.51, H, 6.09; N, 9.16. FAB-HRMS: anal. Calcd for $C_{27}H_{29}N_3O_3$: 444.2287. Found: 444.2298.

Compound 76: N-{3-[2-(4-Methoxyphenyl)ethyl]-4-(3,4-dimethylphenyl)-2-oxo-imidazolidin-1-yl}-2-phenoxyacetamide: $^1$H NMR (CDCl$_3$) δ 8.45 (s, 1H), 7.37 (t, J=6 Hz, 2H), 7.16 (d, J=7.5 Hz, 1H), 7.08 (m, 5H), 6.99 (m, 2H), 6.84 (d, J=8.4 Hz, 2H), 4.65 (s, 2H), 4.38 (t, J=8.1 Hz, 1H), 3.90 (t, J=8.1 Hz, 1H), 3.82 (s, 3H), 3.76 (m, 1H), 3.53 (t, J=8.1 Hz, 1H), 2.94 (m, 1H), 2.84 (m, 1H), 2.70 (m, 1H), 2.30 (s, 6H). MS 474 (MH$^+$). Anal. Calcd. For $C_{28}H_{31}N_3O_4$: C, 71.01, H, 6.60; N, 8.87. Found: C, 70.68, H, 6.46; N, 8.67.

Compound 77: N-{3-[2-(4-Methoxyphenyl)ethyl]-4-[(3,4-dimethylphenyl)]-2-oxo-imidazolidin-1-yl}-2-phenylacetamide: $^1$H NMR (CDCl$_3$) δ 9.49 (s, 1H), 7.85 (m, 2H), 7.46 (m, 1H), 7.35 (m, 2H), 7.17 (s, 3H), 7.10 (m, 2H), 6.86 (m, 2H), 4.46 (t, J=8.7 Hz, 1H), 3.94 (t, J=8.4 Hz, 1H), 3.82 (s, 3H), 3.75 (m, 1H), 3.68 (t, J=8.1 Hz, 1H), 2.94 (m, 1H), 2.86 (m, 1H), 2.74 (m, 1H), 2.31 (s, 6H). MS 444 (MH$^+$). Anal. Calcd. For $C_{27}H_{29}N_3O_3 \cdot \frac{1}{4}H_2O$: C, 72.38, H, 6.64; N, 9.38. Found: C, 72.43, H, 6.08; N, 9.18. FAB-HRMS: anal. Calcd for $C_{27}H_{29}N_3O_3$: 444.2287. Found: 444.2298.

Compound 78: 1-(Isoxazol-5-ylcarbonylamino)-3-[2-(4-methoxyphenyl)-ethyl]-4-(3,4-dimethylphenyl)-2-imidazolidinone: $^1$H-NMR (CDCl$_3$): δ 9.90 (s, 1H), 8.31 (s, 1H), 7.09 (m, 6H), 6.84 (d, J=8.4 Hz, 2H), 4.46 (t, J=8.4 Hz, 1H), 3.94 (t, J=8.4 Hz, 1H), 3.80 (s, 3H), 3.69 (m, 5H), 2.98 (m, 1H), 2.82 (m, 1H), 2.70 (m, 1H), 2.29 (s, 6H). MS m/z (ESI, positive): 435 [M+H]$^+$, (ESI negative): 433 [M−H]$^−$. Anal Calcd for $C_{24}H_{26}N_4O_4$: C, 66.34; H, 6.03; N, 12.89. Found: C, 66.62; H, 5.80; N, 13.04.

Compound 79: 1-(Isoxazol-5-ylcarbonylamino)-3-[2-(4-methoxyphenyl)-ethyl]-4-[4-(tert-butyl)phenyl]-2-imidazolidinone: $^1$H-NMR (CDCl$_3$): δ 9.78 (s, 1H), 8.32 (d, J=1.8 Hz, 1H), 7.42 (d, J=8.4 Hz, 2H), 7.32 (d, J=8.4 Hz, 2H), 7.01 (d, J=1.8 Hz, 1H), 6.84 (d, J=8.4 Hz, 2H), 4.49 (t, J=8.4 Hz, 1H), 3.96 (t, J=8.4 Hz, 1H), 3.80 (s, 3H), 3.67 (m, 2H), 3.00 (m, 1H), 2.84 (m, 1H), 2.68 (m, 1H), 1.34 (s, 9H). MS m/z (ESI, positive): 463 [M+H]$^+$, (ESI negative): 461 [M−H]$^−$. Anal Calcd for $C_{26}H_{30}N_4O_4$: C, 67.51; H, 6.54; N, 12.11. Found: C, 67.80; H, 6.26; N, 12.31.

Compound 80: 1-(Methoxycarbonylamino)-3-[2-(4-methoxyphenyl)ethyl]-4-[4-(tert-butyl)phenyl]-2-imidazolidinone: $^1$H NMR (CDCl$_3$) δ 7.21 (d, J=7.8 Hz, 2H), 7.06 (m, 4H), 6.98 (bs, 1H), 6.85 (m, 2H), 4.34 (t, J=8.4 Hz, 1H), 3.83 (m, 1H), 3.81 (s, 6H), 3.68 (m, 1H), 3.48 (m, 1H), 2.89 (m, 1H), 2.78 (m, 1H), 2.67 (m, 1H), 1.92 (m, 1H), 1.01 (m, 2H), 0.73 (m, 2H). MS 410 (MH$^+$). Anal. Calcd. for $C_{23}H_{27}N_3O_4 \cdot \frac{1}{4}H_2O$: C, 66.73; H, 6.70; N, 10.15. Found: C, 66.81; H, 6.62; N, 10.12.

Compound 81: 2-(Benzylmethylamino)-N-{4-[4-(tert-butyl)phenyl]-3-[2-(4-methoxyphenyl)-ethyl]-2-oxo-imidazolidin-1-yl}-acetamide: $^1$H-NMR (CDCl$_3$): δ 8.73 (s, 1H), 7.36 (m, 8H), 7.07 (d, J=8.4 Hz, 2H), 6.83 (d, J=8.7 Hz, 2H), 4.39 (t, J=8.1 Hz, 1H), 3.83 (m, 4H), 3.69 (m, 3H), 3.48 (t, J=7.8 Hz, 2H), 3.21 (m, 2H), 2.87 (m, 2H), 2.65 (m, 1H), 2.42 (s, 3H), 1.35 (s, 9H). MS m/z (ESI, positive): 529 [M+H]$^+$. Anal Calcd for $C_{32}H_{40}N_4O_3$: C, 72.70; H, 7.63; N, 10.60. Found: C, 72.61; H, 7.80; N, 10.65.

Compound 82: N-(4-(4-cyclopropylphenyl)-3-(4-methoxyphenethyl)-2-oxoimidazolidin-1-yl)-2-(N,N-dimethylsulfamoyl)acetamide. $^1$H NMR (CDCl$_3$) δ 8.92 (s, 0.5H), 8.31 (s, 0.5H), 7.19 (m, 2H), 7.08 (m, 2H), 7.03 (d, J=8.4 Hz, 2H), 6.82 (m, 2H), 4.44 (s, 1H), 4.42 (m, 1H), 4.03 (s, 1H), 3.98 (t, J=8.7 Hz, 0.5H), 3.88 (t, J=8.4 Hz, 0.5H), 3.80 (s, 3H), 3.62 (m, 1H), 3.50 (m, 1H), 3.08 (s, 1.5H), 3.06 (s, 1.5H), 2.99 (s, 3H), 2.90 (m, 1H), 2.72 (m, 1H), 2.63 (m, 1H), 1.92 (m, 1H), 1.01 (m, 2H), 0.73 (m, 2H). MS 501 (MH$^+$). FAB-HRMS: anal. calcd for $C_{25}H_{32}N_4O_5S$: 501.2172. Found: 501.2161.

Examples 9 and 10 describe additional methods for preparing exemplary compounds which have Formula XVII. The skilled practitioner will know how to substitute the appropriate reagents, starting materials and purification methods known to those skilled in the art, in order to prepare additional compounds of the present invention.

EXAMPLE 9

Compound 83: 1-[(4-Cyanophenylmethyl)amino]-3-[2-(4-methoxyphenyl)ethyl]-4-(3,4-dimethylphenyl)-2-imidazolidinone Preparation of 1-[(4-cyanophenylmethyl)amino]-3-[2-(4-methoxyphenyl)ethyl]-4-(3,4-dimethylphenyl)-2-imidazolidinone: To a solution of 1-amino-3-[2-(4-methoxy-phenyl)ethyl]-4-(3,4-dimethylphenyl)-2-imidazolidinone hydrochloride (350 mg, 0.93 mmol), THF (4.5 mL), and 4-cyanobenzaldehyde (131 mg, 1.0 mmol) is stirred at 50° C. for 30 minutes, then cooled in an ice bath and glacial acetic acid (3.5 mL) is added. To the resulting mixture is added NaCNBH$_3$ (183 mg, 2.9 mmol). The reaction is stirred in the cold for 2 hours and ethyl acetate and H$_2$O are added. The mixture is made basic with solid NaHCO$_3$, and the organic phase is washed with 10% aqueous NaHCO$_3$ and brine. The organic phase is dried (Na$_2$SO$_4$) and concentrated under reduced pressure. The residue is purified over silica (45% ethyl acetate/hexanes) to afford 167 mg (40% yield) of the desired product. $^1$H NMR (CDCl$_3$) δ 7.65 (m, 2H), 7.56 (d, J=8.4 Hz, 2H), 7.12 (d, J=7.8 Hz, 1H), 7.05 (m, 2H), 6.89 (m, 2H), 6.84 (m, 2H), 4.20 (m, 3H), 3.82 (s, 3H), 3.67 (m, 1H), 3.48 (t, J n=8.4 Hz, 1H), 3.06 (t, J=8.1 Hz, 1H), 2.91 (m, 1H), 2.76 (m, 1H), 2.67 (m, 1H), 2.29 (s, 3H), 3.26 (s, 3H). MS 455 (MH$^+$). Anal. Calcd. For $C_{28}H_{30}N_4O_2$: C, 73.98, H, 6.65; N, 12.33. Found: C, 73.68, H, 6.65; N, 12.08.

EXAMPLE 10

Compound 84: 4-(3,4-Dimethylphenyl)-3-[2-(4-methoxyphenyl)ethyl]-1-[(pyridin-4-ylmethyl)amino]-imidazolidin-2-one Compound 85: {4-(3,4-dimethylphenyl)-3-[2-(4-methoxyphenyl)ethyl]-2-oxo-imidazolidin-1-yl}-carbamic acid tert-butyl ester Preparation of {4-(3,4-dimethylphenyl)-3-[2-(4-methoxyphenyl)ethyl]-2-oxo-imidazolidin-1-yl}-carbamic acid tert-butyl ester: To a solution of 1-amino-3-[2-(4-methoxyphenyl)ethyl]-4-(3,4-dimethylphenyl)-2-imidazolidinone hydrochloride (500 mg, 1.3 mmol) in $CH_2Cl_2$ (2.0 mL) is added Hunig's base (0.28 mL, 1.6 mmol), followed by a solution of di-tert-butyldicarbonate (312 mg, 1.4 mmol) in $CH_2Cl_2$ (1.0 mL). The solution is stirred for 18 hours and washed with 0.1 N aqueous HCl (2×) and 10% aqueous $NaHCO_3$. The organic phase is dried ($Na_2SO_4$) and concentrated. The residue is triturated in hexanes, cooled briefly at −20° C., the solvent decanted and the resulting solid collected to afford 500 mg (87% yield) of the desired compound. $^1$H NMR (CDCl$_3$) δ 7.16 (d, J=8.4 Hz, 1H), 7.05 (m, 4H), 6.82 (m, 2H), 4.35 (t, J=8.4 Hz, 1H), 3.80 (s, 3H), 3.70 (m, 2H), 3.46 (m, 1H), 2.89 (m, 1H), 2.75 (m, 1H), 2.67 (m, 1H), 2.29 (s, 6H), 1.53 (s, 9H). MS 440 (MH$^+$). Anal. calcd. for $C_{25}H_{33}N_3O_4$: C, 68.31, H, 7.57; N, 9.56. Found: C, 68.09, H, 7.48; N, 9.24.

Preparation of N-{4-(3,4-dimethylphenyl)-3-[2-(4-methoxyphenyl)ethyl]-2-oxo-imidazolidin-1-yl}-3,3-dimethyl-N-pyridin-4-ylmethylbutyramide: A mixture of {4-(3,4-dimethylphenyl)-3-[2-(4-methoxyphenyl)ethyl]-2-oxo-imidazolidin-1-yl}-carbamic acid tert-butyl ester (459 mg, 1.04 mmol), 4-picolyl chloride hydrochloride (257 mg, 1.57 mmol), and DMF (5.5 mL) is cooled in an ice bath and 60% NaH in mineral oil (165 mg, 4.13 mmol) is added. The reaction is stirred in the ice bath for 3 hours and quenched with ice/water. The resulting mixture is extracted with ethyl acetate and the ethyl acetate layer is washed with pH 5.8 phosphate buffer and brine. The organic phase is dried ($Na_2SO_4$) and concentrated under reduced pressure. The crude product is purified over silica (80% ethyl acetate/hexanes) to afford 210 mg (38% yield) of the desired compound which is used directly for the next step. MS 531 (MH$^+$).

Preparation of 4-(3,4-dimethylphenyl)-3-[2-(4-methoxyphenyl)ethyl]-1-[(pyridin-4-ylmethyl)amino]-imidazolidin-2-one: A solution of N-{4-(3,4-dimethylphenyl)-3-[2-(4-methoxyphenyl)ethyl]-2-oxo-imidazolidin-1-yl}-3,3-dimethyl-N-pyridin-4-ylmethyl-butyramide (205 mg, 0.386 mmol) in $CH_2Cl_2$ (1.5 mL) is cooled in an ice bath and triethylsilane (0.129 mL, 0.81 mmol) is added, followed by trifluoroacetic acid (1.5 mL). The ice bath is removed and the reaction is stirred at ambient temperature for 2.5 hours. The reaction is concentrated to an oil, dissolved in ethyl acetate, and washed with 10% aqueous $NaHCO_3$, and brine. The organic phase is dried ($Na_2SO_4$), treated with 2N HCl/ether (0.7 mL), and concentrated under reduced pressure. The solid which results is re-crystallized from dichloromethane/ether to afford 174 mg (76% yield) of the desired compound. $^1$H NMR (DMSO-d$_6$) δ 8.92 (d, J=6.0 Hz, 2H), 8.21 (d, J=6.0 Hz, 2H), 7.14 (d, J=7.5 Hz, 1H), 7.00 (m, 4H), 6.82 (d, J=8.1 Hz, 2H), 4.38 (m, 3H), 3.74 (s, 3H), 3.72 (m, 1H), 3.44 (m, 1H), 3.14 (t, J=7.8 Hz, 1H), 2.68 (m, 1H), 2.52 (m, 1H), 2.24 (s, 3H), 2.20 (s, 3H). MS 431 (MH$^+$). Anal. calcd. for $C_{26}H_{30}N_4O_2 \cdot 2HCl$: C, 62.03, H, 6.41; N, 11.13. Found: C, 61.99, H, 6.41; N, 11.13.

The following are non-limiting examples of compounds which have formula IV.

Compound 86: 1-(Cyclopropylmethylamino)-3-[2-(4-methoxyphenyl)ethyl]-4-(3,4-dimethylphenyl)-2-imidazolidinone: $^1$H-NMR (CDCl$_3$) δ: 7.53 (s, 2H), 7.15 (d, J=7.5 Hz, 1H), 7.03 (m, 4H), 6.82 (d, J=8.7 Hz, 2H), 4.32 (t, J=8.1 Hz, 1H), 3.84 (t, J=8.1 Hz, 1H), 3.80 (s, 3H), 3.68 (m, 1H), 3.38 (t, J=8.1 Hz, 1H), 2.95 (m, 3H), 2.69 (m, 2H), 2.28 (s, 6H), 1.05 (m, 1H), 0.58 (m, 2H), 0.32 (m, 2H). Anal calcd for $C_{26}H_{32}F_3N_3O_4$: C, 61.53; H, 6.35; N, 8.28. Found: C, 61.89; H, 6.57; N, 8.04.

Compound 87: 1-Benzylamino-3-[2-(4-methoxyphenyl)ethyl]-4-[4-(tert-butyl)phenyl]-2-imidazolidinone: $^1$H-NMR (CDCl$_3$) δ: 7.39 (m, 6H), 7.11 (d, J=8.1 Hz, 2H), 7.04 (d, J=8.4 Hz, 2H), 6.83 (d, J=8.7 Hz, 2H), 5.35 (s, 2H), 4.24 (t, J=8.1 Hz, 1H), 4.17 (d, J=3.3 Hz, 1H), 3.81 (s, 3H), 3.66 (m, 1H), 3.53 (t, J=8.1 Hz, 1H), 3.13 (t, J=8.1 Hz, 1H), 2.79 (m, 3H), 1.37 (s, 9H). MS m/z (ESI, positive): 458 [M+H]$^+$. Anal calcd for $C_{31}H_{35}F_3N_3O_3$: C, 67.13; H, 6.36; N, 7.58. Found: C, 67.40; H, 6.09; N, 7.76.

Compound 88: 1-Benzylamino-4-(3,4-dimethylphenyl)-3-[2-(4-methoxyphenyl)ethyl]-2-imidazolidinone: $^1$H-NMR (CDCl$_3$) δ: 7.44 (d, J=8.4 Hz, 1H), 7.34 (m, 3H), 7.11 (d, J=7.2 Hz, 1H), 7.04 (d, J=8.7 Hz, 2H), 6.89 (m, 5H), 4.18 (m, 3H), 3.81 (s, 3H), 3.66 (m, 1H), 3.53 (t, J=8.4 Hz, 1H), 3.12 (t, J=8.1 Hz, 1H), 2.91 (m, 1H), 2.70 (m, 2H), 2.27 (d, J=5.4 Hz, 6H). MS m/z (ESI, positive): 430 [M+H]$^+$. Anal calcd for $C_{29}H_{32}F_3N_3O_4$: C, 66.15; H, 5.93; F, 10.82; N, 7.98. Found: C, 66.50; H, 6.09; F, 11.13; N, 8.21.

Compound 89: 1-[(4-Fluorophenylmethyl)amino]-3-[2-(4-methoxyphenyl)ethyl]-4-(3,4-dimethylphenyl)-2-imidazolidinone: $^1$H NMR (CDCl$_3$) δ 7.38 (m, 2H), 7.12 (d, J=7.5 Hz, 1H), 7.05 (m, 4H), 6.93 (m, 2H), 6.83 (m, 2H), 4.20 (t, J=8.1 Hz, 1H), 4.14 (d, J=12.3 Hz, 1H), 4.08 (d, J=12.6 Hz, H), 3.81 (s, 3H), 3.68 (m, 1H), 3.48 (t, J=8.4 Hz, 1H), 2.93 (m, 1H), 2.76 (m, 1H), 2.68 (m, 1H), 2.29 (s, 3H), 2.27 (s, 3H). MS 448 (MH$^+$). Anal. calcd. For $C_{27}H_{30}FN_3O_2$: C, 72.46, H, 6.76; N, 9.39. Found: C, 72.36, H, 6.42; N, 9.12.

Compound 90: 1-[(4-(Dimethylamino)phenylmethyl)amino]-3-[2-(4-methoxyphenyl)ethyl]-4-(4-methoxyphenyl)-2-imidazolidinone. $^1$H NMR (CDCl$_3$) δ 7.47 (d, J=7.8 Hz, 2H), 7.22 (d, J=8.4 Hz, 4H), 6.98 (m, 5H), 6.82 (d, J=8.4 Hz, 2H), 4.55 (t, J=7.8 Hz, 1H), 4.25 (d, J=13.2 Hz, 1H), 4.19 (d, J=13.2 Hz, 1H), 3.81 (m, 1H), 3.77 (s, 3H), 3.71 (s, 3H), 3.43 (m, 1H), 3.30 t, J=7.8 Hz, 1H), 3.04 (m, 1H), 3.01 (s, 6H), 2.68 (m, 2H). MS 475 (MH$^+$). Anal. calcd. for $C_{28}H_{34}N_4O_3 \cdot ½HCl$: C, 63.54; H, 6.76; N, 10.59. Found: C, 63.19; H, 6.65; N, 10.30.

Compound 91: 1-[(4-(Dimethylamino)phenylmethyl)amino]-3-[2-(4-methoxyphenyl)ethyl]-4-[4-(tert-butyl)phenyl]-2-imidazolidinone: $^1$H NMR (CDCl$_3$) δ 7.90 (s, 4H), 7.37 (d, J=8.4 Hz, 2H), 7.20 (d, J=8.1 Hz, 2H), 6.94 (d, J=8.4 Hz, 2H), 6.77 (d, J=8.7 Hz, 2H), 4.68 (m, 2H), 4.37 (t, J=8.1 Hz, 1H), 3.98 (t, J=7.8 Hz, 1H), 3.78 (m, 4H), 3.60 (m, 1H), 3.16 (s, 6H), 2.72 (m, 3H), 1.29 (s, 9H). MS m/z (ESI, positive): 501 (MH$^+$). Anal calcd for $C_{31}H_{42}Cl_2N_4O_2$: C, 64.91; H, 7.38; N, 9.77. Found: C, 65.24; H, 7.71; N, 10.02.

Compound 92: 1-[(4-(Dimethylamino)phenylmethyl)amino]-3-[2-(4-methoxyphenyl)ethyl]-4-(3,4-dimethylphenyl)-2-imidazolidinone: $^1$H NMR (CDCl$_3$) δ 7.52 (d, J=7.8 Hz, 2H), 7.33 (bs, 2H), 7.16 (d, J=7.8 Hz, 4H), 6.82 (d, J, 8.4 Hz, 2H), 4.53 (t, J=7.8 Hz, 1H), 4.27 (d, J=13.5 Hz, 1H), 4.22 (d, J=13.5 Hz, 1H), 3.84 (t, J=8.1 Hz, 1H), 3.71 (s, 3H), 3.50

(m, 1H), 3.34 (t, J=7.5 Hz, 1H), 3.07 (m, 1H), 3.03 (s, 6H), 2.73 (m, 1H), 2.64 (m, 1H), 2.23 (s, 3H), 2.21 (s, 3H). MS 473 (MH$^+$). Anal. calcd. For $C_{29}H_{36}N_4O_2$2HCl: C, 63.85, H, 7.02; N, 10.27. Found: C, 64.18, H, 6.78; N, 10.07.

Compound 93: 1-[(Pyridin-2-ylmethyl)amino]-3-[2-(4-methoxyphenyl)ethyl]-4-(3,4-dimethylphenyl)-2-imidazolidinone: $^1$H NMR (CDCl$_3$) δ 8.78 (s, 1H), 8.43 (m, 2H), 7.89 (bs, 3H), 7.08 (d, J=7.5 Hz, 1H), 6.96 (m, 4H), 6.74 (d, J=8.1 Hz, 2H), 4.86 (s, 2H), 4.41 (m, 1H), 4.10 (m, 1H), 3.76 (s, 3H), 3.56 (m, 1H), 3.42 (m, 1H), 2.84 (m, 1H), 2.61 (m, 1H), 2.53 (m, 1H), 2.24 (s, 3H), 2.23 (s, 3H). MS 431 (MH$^+$). Anal. calcd. for $C_{26}H_{30}N_4O_2$2HCl H$_2$O: C, 59.89, H, 6.58; N, 10.74. Found: C, 59.73, H, 6.62; N, 10.48.

Compound 94: 1-[(Pyridin-3-ylmethyl)amino]-3-[2-(4-methoxyphenyl)ethyl]-4-(3,4-dimethylphenyl)-2-imidazolidinone: $^1$H NMR (DMSO-d$_6$+1% TFA-d) δ 9.07 (s, 1H), 8.91 (d, J=5.7 Hz, 1H), 8.67 (d, J=8.1 Hz, 1H), 8.10 (dd, J=5.7, 7.8 Hz, 1H), 7.13 (d, J=7.5 Hz, 1H), 6.95 (m, 4H), 6.79 (d, J=8.4 Hz, 2H), 4.37 (t, J=8.1 Hz, 1H), 4.27 (s, 2H), 3.71 (s, 3H), 3.69 (m, 1H), 3.42 (m, 1H), 3.13 (t, J=7.8 Hz, 1H), 2.69 (m, 1H), 2.58 (m, 1H), 2.46 (m, 1H), 2.21 (s, 3H), 2.19 (s, 3H).). MS 431 (MH$^+$). Anal. calcd. for $C_{26}H_{30}N_4O_2$2HCl 3H$_2$O: C, 56.01, H, 6.87, N, 10.05. Found: C, 56.19, H, 6.47; N, 9.81.

Compound 95: 1-[(Pyridin-4-ylmethyl)amino]-3-[2-(4-methoxyphenyl)ethyl]-4-(4-(tert-butyl)phenyl)-2-imidazolidinone: $^1$H NMR (DMSO-d$_6$) δ 8.89 (d, J=6.3 Hz, 2H), 8.17 (d, J=6.6 Hz, 2H), 7.39 (2H, J=8.4 Hz, 2H), 7.18 (d, J=8.1 Hz, 2H), 6.98 (d, J=8.4 Hz, 2H), 6.78 (d, J=8.7 Hz, 2H), 4.39 (t, J=8.1 Hz, 1H), 4.34 (s, 2H), 3.71 (s, 3H), 3.69 (m, 1H), 3.43 (m, 1H), 3.12 (m, 1H), 2.72 (m, 1H), 2.49 (m, 1H), 1.29 (s, 9H). MS 459 (MH$^+$). Anal. Calcd. For $C_{28}H_{34}N_4O_2$2HCl½H$_2$O: C, 62.22; H, 6.90; N, 10.37. Found: C, 62.54; H, 6.69; N, 10.18.

For the following compound, the starting material, 3-chloromethylquinoline hydrochloride, is prepared according to the method of *J. Am. Chem. Soc.* (1955), Vol. 77, 1054-1055, included herein by reference.

Compound 96: 4-(3,4-Dimethylphenyl)-3-[2-(4-methoxyphenyl)ethyl]-1-[(quinolin-3-ylmethyl)-amino]-2-imidazolidinone: $^1$H NMR (DMSO-d$_6$) δ 9.44 (d, J=1.5 Hz, 1H), 9.19 (s, 1H), 8.49 (d, J=8.4 Hz, 1H), 8.34 (d, J=8.1 Hz, 1H), 8.16 (t, J=7.2 Hz, 1H), 7.98 (t, J=7.5 Hz, 1H), 7.09 (d, J=7.8 Hz, 1H), 6.92 (m, 4H), 6.74 (d, J=8.7 Hz, 2H), 4.45 (s, 2H), 4.40 (t, J=8.1 Hz, 1H), 3.79 (t, J=8.1 Hz, 1H), 3.67 (s, 3H), 3.40 (m, 1H), 3.24 (t, J=7.8 Hz, 1H), 2.65 (m, 1H), 2.58 (m, 1H), 2.40 (m, 1H), 2.19 (s, 3H), 2.13 (s, 3H). MS 481 (MH$^+$). FAB-HRMS: anal. calcd for $C_{30}H_{32}N_4O_2$: 481.2604. Found: 481.2583.

Compound 97: 1-[(Phenylethyl)amino]-3-[2-(4-methoxyphenyl)ethyl]-4-(3,4-dimethylphenyl)-2-imidazolidinone: $^1$H NMR (CDCl$_3$) δ 7.34 (m, 2H), 7.28 (m, 3H), 7.21 (d, J=7.8 Hz, 1H), 7.12 (m, 2H), 7.05 (m, 2H), 6.84 (m, 2H), 4.60 (t, J=8.1 Hz, 1H), 3.88 (t, J=8.1 Hz, 1H), 3.70 (s, 3H), 3.52 (m, 1H), 3.31 (m, 3H), 2.88 (m, 2H), 2.78 (m, 1H), 2.65 (m, 1H), 2.56 (m, 1H, overlap with DMSO), 2.25 (s, 6H). MS 444 (MH$^+$). FAB-HRMS: anal. calcd for $C_{28}H_{33}N_3O_2$: 444.2651. Found: 444.2636.

Compound 98: 1-[(4-(1H-imidazol-1-yl)phenylmethyl)amino]-3-[2-(4-methoxyphenyl)ethyl]-4-(3,4-dimethylphenyl)-2-imidazolidinone: $^1$H NMR (DMSO-d$_6$+1% TFA) δ 9.85 (s, 1H), 8.39 (d, J=1.5 Hz, H), 8/01 (d, J=1.8 Hz, H), 7.91 (d, J=8.7 Hz, 2H), 7.80 (d, J=8.4 Hz, 2H), 7.19 (d, J=7.2 Hz, 1H), 7.06 (m, 4H), 7.84 (d, J=7.5 Hz, 2H), 4.60 (t, J=7.5 Hz, 1H), 4.47 (m, 2H), 3.72 (s, 3H), 3.54 (m, 1H), 2.79 (m, 1H), 2.65 (m, 1H), 2.58 (m, 1H, overlap with DMSO), 2.25 (s, 3H), 2.23 (s, 3H). MS 496 (MH$^+$). Anal. Calcd. For $C_{30}H_{33}N_5O_2$2HCl½H$_2$O: C, 62.39, H, 6.28; N, 12.13. Found: C, 62.72, H, 6.27; N, 11.75.

The following are non-limiting examples of compounds according to the present invention.

Compound 99: 1-N-[2-(Imidazol-1-yl)ethyl]-N-[iso-butyroyl]amino-3-[2-(4-methoxyphenyl)-ethyl]-4-[(4-tert-butyl)phenyl]-2-imidazolidinone. $^1$H NMR (DMSO-d$_6$) 7.8 (brd, 1H), 7.6 (brd, 1H), 7.4 (brm, 4H), 7.25 (brd, 1H), 7.1 (brd, 2H), 6.9 (brd, 2H), 4.4 (m, 2H), 4.0 (m, 2H), 3.75 (s, 3H), 3.7 (m, 4H), 2.8-2.4 (m, 3H), 1.3 (brs, 15H). FAB-HRMS calcd. for $C_{31}H_{41}N_5O_3$: 532.3288; found 532.3267 (MH$^+$).

Compound 100: 1-N-[2-(Imidazol-1-yl)ethyl]-N-[acetyl]amino-3-[2-(4-methoxyphenyl)ethyl]-4-[(4-tert-butyl)phenyl]-2-imidazolidinone. $^1$H NMR (DMSO-d$_6$) δ 7.6 (brs, 1H), 7.45 (brm, 3H), 7.33-7.2 (brm, 2H), 7.05 (brm, 2H), 6.8 (brm, 3H), 4.6 (brm, 1H), 4.3-4.0 (brm, 2H), 3.8 (brm, 1H), 3.65 (s, 3H), 3.5 (brm, 2H), 3.3 (brm, 3H), 2.8-2.6 (brm, 2H), 1.8 (m, 3H) 1.3 (s, 9H). FAB-HRMS calcd. for $C_{29}H_{37}N_5O_3$: 504.2975; found 504.2959 (MH$^+$).

Compound 101: 1-[(Pyridin-3-yl)methylsulfonyl]amino-3-(3-phenylpropyl)-4-(4-methoxyphenyl)-2-imidazolidinone: $^1$H NMR (CDCl$_3$) δ 8.84 (d, J=1.5 Hz, 1H), 8.47 (dd, J=1.2, 3.6 Hz, 1H), 7.95 (dt, J=1.8, 7.8 Hz, 1H), 7.23 (m, 6H), 7.11 (d, J=8.4 Hz, 2H), 6.92 (d, J=8.4 Hz, 2H), 4.60 (s, 2H), 4.54 (t, J=8.4 Hz, 1H), 3.97 (m, 1H), 3.83 (s, 3H), 3.46 (m, 2H), 2.86 (m, 1H), 2.56 M, 2H), 1.74 (m, 2H). (MS) 481 (MH$^+$), 479 (M−H$^-$). Anal. Calcd for $C_{25}H_{28}N_4O_4S$: C, 62.48; H, 5.87; N, 11.66. Found: C, 62.89; H, 5.93; N, 11.58.

Compound 102: 1-[[2-(9H-fluoren-9-ylmethoxy)-2-oxoethyl]sulfonylamino]-3-[2-(4-methoxyphenyl)ethyl]-4-(4-cyclopropylphenyl)-2-imidazolidinone. HPLC retention time 6.011 minutes, (MS) 652 (MH$^+$).

Compound 103: N-{4-(3,4-dimethylphenyl)-3-[2-(4-methoxyphenyl)ethyl]-2-oxo-imidazolidin-1-yl}-3,3-dimethyl-N-pyridin-4-ylmethylbutyramide.

Compound 104: 1-[(2-Amino-2-oxoethyl)sulfonylamino]-3-[3-(4-methoxyphenyl)propyl]-4-(4-cyclopropylphenyl)-2-imidazolidinone: $^1$H NMR (CDCl$_3$) δ 8.82 (s, 1H), 8.67 (s, 1H), 7.21 (d, J=8.1 Hz, 2H), 7.10 (d, J=8.1 Hz, 2H), 7.02 (d, J=8.7 Hz, 2H), 6.81 (d, J=8.7 Hz, 2H), 6.60 (s, 1H), 4.57 (t, J=8.1 Hz, 1H), 4.18 (m, 2H), 3.98 (t, J=8.7 Hz, 1H), 3.80 (s, 3H), 3.54 (m, 1H), 3.41 (m, 1H), 2.82 (m, 1H), 2.49 (m, 2H), 1.93 (m, 1H), 1.70 (m, 2H), 1.03 (m, 2H), 0.73 (m, 2H). MS 487 (MH$^+$). Anal. calcd. for $C_{24}H_{30}N_4O_5S$¾H$_2$O: C, 57.64; H, 6.35; N, 11.20. Found: C, 57.73; H, 6.11; N, 10.91.

Enantio-Selective Synthesis

The compounds of the present invention can be prepared in enhanced enantiomeric purity by preparing the 1-N-amino-2-imidazolidinone intermediates utilizing the process outlined in Schemes I and Example 11 herein below. Example 12 exemplifies a procedure for converting chiral compounds to Kv1.5 potassium channel inhibitors of the present invention having enhanced enantiomeric purity. What is meant herein by the term "enhanced enantiomeric purity" is a final product wherein the final 2-oxazolidinone formed in step (c) of the present process has at least 90% of the material isolated existing as one optical isomer; either the R or S enantiomer. In many instances, the optical purity is at least 95% one optical isomer, and in the procedure described herein below in Example 11, 99.5% of the material isolated had the R configuration. However, by using procedures known to the artisan, the optical purity of the products formed in step (c) can be further enhanced in their enantiomeric purity.

Scheme I

The following is a first iteration of the procedure for preparing exemplary compounds of the present invention having enhanced enantiomeric purity. The units R, $R^1$, and L are the same as defined herein above.

a) (i) reacting a chiral 2-aminoamide having the formula:

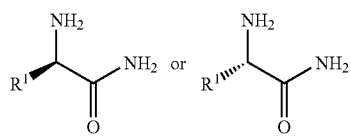

with an acid chloride having the formula:

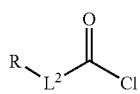

$L^2$ is a unit having the formula $—[C(R^{9a}R^{9b})]_j—$, the index j is 1 or 2; in the presence of a base to form a chiral di-amide having the formula:

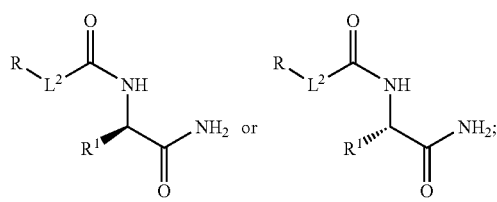

b) reacting the chiral di-amide formed in step (a) with a reducing agent to form a di-amine having the formula:

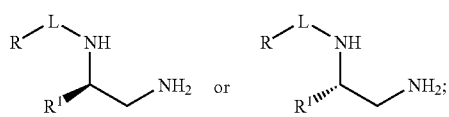

c) reacting the di-amine formed in step (b) with a reagent which is capable of introducing a carbonyl group to form a 2-imidazolidinone having the formula:

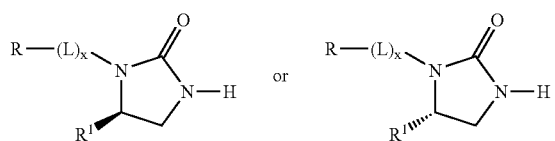

wherein said 2-imidazolidinone has at least 90% of the same configuration as the chiral 2-aminoamide of step (a); and d) reacting the 2-imidazolidinone formed in step (c) with a reagent capable of introducing an amino unit onto the imidazolidinone ring to form a 1-N-amino-2-imidazolidinone.

Or in a second iteration of the present process, step (a)(i) can be suitably modified to be replaced by the following:

a)(ii) reacting a chiral 2-aminoamide having the formula:

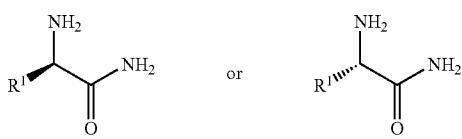

with an acid having the formula:

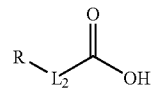

$L^2$ is a unit having the formula $—[C(R^{9a}R^{9b})]_j—$, the index j is 1 or 2; in the presence of a peptide coupling reagent to form a chiral di-amide having the formula:

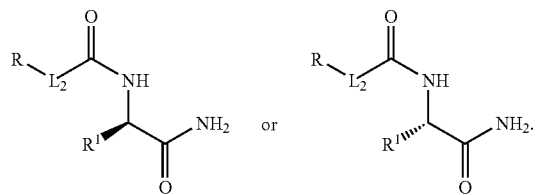

The following is a description of the steps comprising the process of the present invention.

Step (a) Formation of a chiral di-amide having the formula:

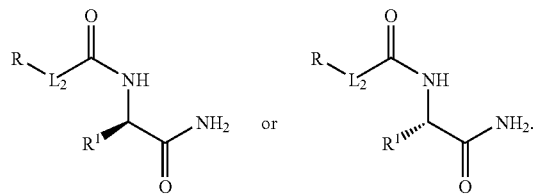

Step (a)(i) is the first iteration of the process of the present invention and relates to the coupling of a 2-aminoamide and an acid chloride to form a chiral di-amide.

This step may optionally be conducted in the presence of a solvent which does not react with the either the acid chloride or the 2-aminoamide. Non-limiting examples of said solvents include solvents chosen from dimethylformamide, dimethylacetamide, tetrahydrofuran, methylenechloride, chloroform, 1,2-dichloroethane, 1,1,1-trichloroethane, 1,2-dimethoxyethane, tert-butyl methyl ether, 2-methyltetrahydrofuran, diethylene glycol dimethyl ether, dioxane, and dimethylsulfoxide. In another iteration, water can be used as a co-solvent for this reaction under certain known to the artisan conditions.

Step (a)(i) is conducted in the presence of a base. As a first iteration of step (a)(i), non limiting examples of bases which can be used in the process of the present invention include bases chosen from triethylamine, N-methylmorpholine, diisopropylmethylamine, diisopropyl-ethylamine, pyridine, lutidine, and N-methylpiperidine. In a second iteration of step (a)(i), and in certain conditions wherein water is present as a co-solvent, non limiting examples of bases which can be used in the process of the present invention include bases chosen from sodium bicarbonate, sodium carbonate, sodium hydroxide, potassium carbonate, and potassium hydroxide.

Step (a)(ii) is a second iteration of the process of the present invention and relates to the coupling of a 2-aminoamide and an acid in the presence of a peptide coupling reagent to form a chiral di-amide.

The coupling reagents which can be utilized for this step are those well known by the artisan, and which include the following non-limiting examples:

i) Benzotriazole-1-yl-oxy-tris-(dimethylamino)-phosphonium hexafluorophosphate (BOP);
ii) N,N'-Carbonyldiimidazole (CDI);
iii) Dicyclohexylcarbodiimide (DCC);
iv) 3-(Diethoxyphosphoryloxy)-3H-benzo[d][1,2,3]triazin-4-one (DEPBT);
v) N,N'-Diisopropylcarbodiimide (DIC);
vi) 1-Ethyl-3-(3-dimethyllaminopropyl)carbodiimide hydrochloride (EDC);
vii) 2-(1H-7-Azabenzotriazol-1-yl)-1,1,3,3-tetramethyl uronium hexafluorophosphate Methanaminium; HATU);
viii) O-Benzotriazole-N,N,N',N'-tetramethyl-uronium-hexafluoro-phosphate (HBTU);
ix) 1H-Benzotriazolium 1-[bis(dimethylamino)methylene]-5-chloro-hexa-fluorophosphate (1-),3-oxide (HCTU);
x) Benzotriazol-1-yl-oxytripyrrolidinophosphonium hexafluorophosphate (PyBOP);
xi) O-(Benzotriazol-1-yl)-N,N,N',N'-tetramethyluronium tetrafluoroborate (TBTU); and
xii) 4,5-Dicyanoimidazole.

This step may optionally be conducted in the presence of a solvent, non-limiting examples of said solvents include solvents chosen from dimethylformamide, dimethylacetamide, tetrahydrofuran, methylenechloride, chloroform, 1,2-dichloroethane, 1,1,1-trichloroethane, 1,2-dimethoxyethane, tert-butyl methyl ether, 2-methyltetrahydrofuran, diethylene glycol dimethyl ether, dioxane, and dimethylsulfoxide. In another iteration, water can be used as a co-solvent for this reaction under certain known to the artisan conditions.

Step (b) Formation of a di-amine having the formula:

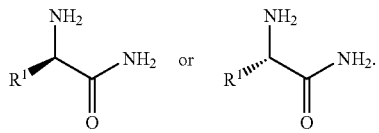

Step (b) relates to reacting the chiral di-amide formed in step (a) with a reducing agent to form a chiral diamine. Non-limiting examples of reducing agents suitable for use in step (b) include chosen from $BH_3$:DMS, $BH_3$:THF, $B_2H_6$, $AlH_3$, $AlCl_3$—$LiAlH_4$, $NaBH_4$-organic acid complexes, $NaBH_4$—$BF_3Et_2O$, and sodium bis(2-methoxyethoxy)-aluminum hydride.

This step may optionally be conducted in the presence of a solvent, non-limiting examples of said solvents include solvents chosen from tetrahydrofuran, diethyl ether, and tert-butyl methyl ether.

Step (c) Formation of a chiral 2-imidazolidinone having the formula:

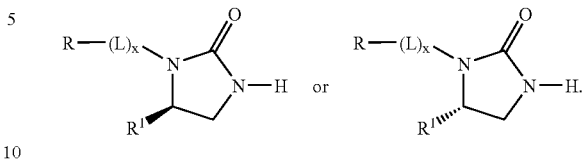

Step (c) relates to reacting the di-amine formed in step (b) with a reagent which is capable of introducing a carbonyl group. Non-limiting examples of reagents which are capable of introducing a carbonyl group and thereby resulting in the cyclization of the compound formed in step (b) into a 2-imidazolidinone are reagents chosen from 1,1'-carbonyldiimidazole, phosgene, triphosgene, dimethylpyrocarbonate, and di-tert-butyl-pyrocarbonate.

This step may optionally be conducted in the presence of a solvent, non-limiting examples of said solvents include solvents chosen from acetonitrile, dimethylformamide, dimethylacetamide, tetrahydrofuran, methylenechloride, chloroform, 1,2-dichloroethane, 1,1,1-trichloroethane, 1,2-dimethoxyethane, tert-butyl methyl ether, 2-methyltetrahydro-furan, diethylene glycol dimethyl ether, dioxane, and dimethylsulfoxide.

Step (d) Formation of a 1-N-amino-2-imdazolidinone intermediate having the formula:

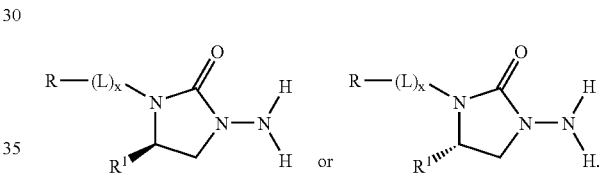

Step (d) relates to reacting the 2-imidazolidinone formed in step (c) under conditions wherein an amino group is formed at the 1-position of the 2-imidazolidinone ring.

A first iteration of this step relates to the introduction of an amino unit by way of a two step process, the first step (d)(i) encompasses the reaction of the chiral 2-imizolidinone with sodium nitrite in the presence of an organic acid, for example, glacial acetic acid. The reaction intermediate thus formed in step (d)(i) is then reduced in a second step (d)(ii). A non-limiting example of a reducing reagent suitable for use includes zinc metal. In this iteration, the organic acid in step (d)(i) can serve as a suitable solvent for both steps.

The chiral 1-N-amino-2-imidazolidinone in one iteration is present in greater than 99% enantiomeric excess and is suitable for use directly in preparation of the Kv 1.5 potassium channel blockers of the present invention.

The following is a specific example of the preparation of a compound according to the present invention having enhanced enantiomeric purity. The skilled practitioner will know how to substitute the appropriate reagents, starting materials and purification methods known to those skilled in the art, in order to prepare additional compounds of the present invention having enhanced enantiomeric purity.

EXAMPLE 11

Compound 105: 1-Amino-3-[2-(4-methoxyphenyl)ethyl]-4-(R)-(4-methoxyphenyl)-2-imidazolidinone Preparation of 2-(R)-(4-methoxyphenyl)-2-[2-(4-methoxyphenyl)acetylamino]-acetamide: A solution of (R)-2- amino-2-(4-methoxyphenyl)acetamide (200 g, 1.11 mol), triethylamine (124 g, 1.22 mol) in dimethylformamide (2 L) is cooled to 5° C. in an ice bath and (4-methoxyphenyl)acetyl chloride (225 g, 187 mL, 1.22 mol) is added dropwise at a rate which maintains the temperature in a range from 5° C. to 7° C. After 1.5 hours the additional stirring in the cold, the reaction solution is transferred to a vessel containing water (12 L). The solid which forms upon standing is collected and rinsed several times with water. The material collected is dried to a constant weight affording 323.9 g (89% yield) of the desired product. Analysis by chiral HPLC indicates 98.6% enantiomeric purity.

Preparation of 1-(R)-(4-methoxyphenyl)-$N^1$-[2-(4-methoxyphenyl)ethyl]ethane-1,2-diamine: A solution of 2-(R)-(4-methoxyphenyl)-2-[2-(4-methoxyphenyl)-acetylamino]-acetamide (316 g, 0.96 mol) in THF (2 L) is heated to 35° C. and borane dimethyl sulfide (428 mL, 4.28 mol) is added over approximately 1 hour after which the reaction is heated to reflux for 18 hours. After cooling the reaction solution to 8° C. sufficient 3N HCl (approx. 400 mL) is added until the pH of the solution is approximately 1. The reaction solution is then heated to reflux for 1 hour. The reaction is then cooled and the pH adjusted to 8 by the slow addition of 25% aqueous NaOH (300 mL). The entire reaction solution is poured into a vessel containing a mixture of $CH_2Cl_2$ (3 L) and water (1.5 L). The organic layer is decanted and the water layer treated with $CH_2Cl_2$ (1.5 L). The organic layers are combined, washed with brine (2.5 L) then dried over $Na_2SO_4$. The solvent in removed in vacuo to afford 302 g (quantitative yield) of the desired product as an amber colored oil.

Preparation of 5-(R)-(4-methoxyphenyl)-1-[2-(4-methoxyphenyl)ethyl]-2-imidazolidinone: A solution of 1-(R)-(4-methoxyphenyl)-$N^1$-[2-(4-methoxyphenyl)ethyl]ethane-1,2-diamine (446 g, 1.48 mol) in ethyl acetate (2.25 L) is placed in a water bath and 1,1'-carbonyldiimidazole (264 g, 1.62 mol) is added in portions. The reaction is then heated to reflux for 1.5 hours after which the solution is cooled, treated with 1N HCl (2×1.5 L), brine (2×1.5 L), dried over $Na_2SO_4$ and set aside in the cold. After standing the precipitate which forms is removed by filtration and the solvent removed under reduced pressure to afford 468 g (96% yield) of the desired product. Chiral HPLC of the product thus obtained to have 99.5% of the desired (R) enantiomer present.

Preparation of 1-amino-3-[2-(4-methoxyphenyl)ethyl]-4-(R)-(4-methoxyphenyl)-2-imidazolidinone: A solution of 5-(R)-(4-methoxyphenyl)-1-[2-(4-methoxy-phenyl)ethyl]-2-imidazolidinone (257 g, 0.79 mol) in glacial acetic acid (2.2 L) is cooled to 13° C. A solution of sodium nitrite (76 g, 1.1 mol) in water (380 mL) is added dropwise and the reaction is stirred an additional 1.5 hours. The solution is then cooled to 5° C. and Zn dust (194 g, 297 g-atm) is added in portions over about 90 minutes. The resulting suspension is then poured into water (2 L) and $CH_2Cl_2$ (2 L) is added. The reaction mixture is then cooled in an ice bath and treated with concentrated $NH_4OH$ (2480 mL). The solution is agitated and the organic phase decanted. The aqueous layer is treated with an additional amount of $CH_2Cl_2$ (2 L), the organic washings are combined, washed with brine, dried over $Na_2SO_4$, and the solvent removed under reduced pressure to a crude product. $^1$H NMR (300 MHz, $CDCl_3$) δ 7.14 (d, J=8.81, 2H, ArH), 7.00 (d, J=8.81, 2H, ArH), 6.88 (d, J=8.51, 2H, ArH), 6.79 (d, J=8.51, 2H, ArH), 4.24 (m, 1H), 3.81 (s, 3H, $CH_3$), 3.77 (s, 3H, $CH_3$), 3.51-3.72 (m, 2H), 3.13 (m, 1H), 2.51-2.95 (m, 3H), 1.48-1.80 (br s, 2H).

The following is a non-limiting example of a chiral 1-N-amino-2-imidazolidinone formed by the process of the present invention.

EXAMPLE 12

Compound 106: 1-(Methylsulfonylamino)-3-[2-(4-methoxyphenyl)ethyl]-4-(R)-(4-methoxyphenyl)-2-imidazolidinone Preparation of 1-(methylsulfonylamino)-3-[2-(4-Methoxyphenyl)ethyl]-4-(R)-(4-methoxyphenyl)-2-imidazolidinone: A solution of 1-amino-3-[2-(4-methoxyphenyl)-ethyl]-4-(R)-(4-methoxyphenyl)-2-imidazolidinone (247 g, 0.72 mol) in dichloromethane (2.35 L) and pyridine (174 mL, 2.15 mol) is cooled in an ice bath to 18° C. Methanesulfonyl chloride (73 mL, 0.94 mol) is added dropwise. The reaction is stirred cold for 2.5 hours then washed with 0.5 N HCl (2×1.5 L), brine (2×1.5 L) and dried ($Na_2SO_4$). The solvent is then removed in vacuo to afford a mixture of the desired product (75%) and unreacted starting material (25%) which is separated by liquid chromatography. $[\alpha]^{20}_D$ −39.83 (c 0.89, $CHCl_3$) $^1$H NMR (300 MHz, $CDCl_3$) δ 7.16 (d, J=8.81, 2H, ArH), 7.02 (d, J=8.51, 2H, ArH), 6.91 (d, J=8.81, 2H, ArH), 6.80 (d, J=8.81, 2H, ArH), 4.41 (m, 1H), 3.92 (m, 1H), 3.82 (s, 3H, $CH_3$), 3.77 (s, 3H, $CH_3$), 3.60-3.72 (m, 1H), 3.30 (m, 1H), 3.03 (s, 3H, $CH_3$), 2.87-2.98 (m, 1H), 2.53-2.79 (m, 3H). MS 418 ($MH^+$). Anal. Calcd. for $C_{21}H_{27}N_3O_4S\cdot¼H_2O$: C, 59.77, H, 6.57; N, 9.96. Found: C, 59.82, H, 6.06; N, 9.85. FAB-HRMS: anal. calcd for $C_{21}H_{27}N_3O_4S$: 418.18005. Found: 418.17960.

Further compounds according to the present invention include:

Compound 107: N-{(4S)-4-(4-methoxyphenyl)-3-[2-(4-methoxyphenyl)ethyl]-2-oxoimidazolidin-1-yl}methanesulfonamide; HRMS: calcd for $C_{20}H_{25}N_3O_5S$+H+, 420.15877; found (ESI, [M+H]+Obs'd), 420.1592; HPLC Retention time, 2.8 min.

Compound 108: tert-butyl {4-(3,4-dimethylphenyl)-3-[2-(4-methoxyphenyl)ethyl]-2-oxoimidazolidin-1-yl}(quinolin-3-ylmethyl)carbamate; HRMS: calcd for $C_{35}H_{40}N_4O_4$+H+, 581.31223; found (ESI, [M+H]+Obs'd), 581.3127; HPLC Retention time, 3.4 min.

Compound 109: tert-butyl [2-({4-(4-tert-butylphenyl)-3-[2-(4-methoxyphenyl)ethyl]-2-oxoimidazolidin-1-yl}amino)-2-oxoethyl]methylcarbamate; CHN anaylsis: C, 71.75; H, 6.83; N, 9.38, Calculated $C_{35}H_{40}N_4O_4$+0.25$H_2O$, C, 71.83; H, 6.98, N, 9.57; HPLC Retention time, 5.95 min.

Compound 110: 1-amino-3-[2-(4-methoxyphenyl)ethyl]-4-[4-(trifluoromethoxy)phenyl]imidazolidin-2-one; HRMS: calcd for $C_{19}H_{20}F_3N_3O_3$+H+, 396.15295; found (ESI, $[M+H]^+$), 396.1535; HPLC Retention time, 2.9 min.

Compound 111: N-{4,4-diethyl-3-[2-(4-methoxyphenyl)ethyl]-2-oxoimidazolidin-1-yl}methanesulfonamide; HRMS: calcd for $C_{17}H_{27}N_3O_4S$+H+, 370.17950; found (ESI, [M+H]+Obs'd), 370.1799; HPLC Retention time, 2.8 min.

Compound 112: 4-(4-tert-butylphenyl)-3-[2-(4-methoxyphenyl)ethyl]-1-piperazin-1-ylimidazolidin-2-one; HRMS: calcd for $C_{26}H_{36}N_4O_2$+H+, 437.29110; found (ESI, [M+H]+Obs'd), 437.2917; HPLC Retention time, 3.0 min.

Compound 113: N-{3-[2-(4-ethoxyphenyl)ethyl]-4-(4-methoxyphenyl)-2-oxoimidazolidin-1-yl}methanesulfonamide; HRMS: calcd for $C_{21}H_{27}N_3O_5S$+H+, 434.17442; found (ESI, [M+H]+Obs'd), 434.1746; HPLC Retention time, 2.9 min.

Compound 114: N-{4-(4-cyclopropylphenyl)-3-[2-(4-methoxyphenyl)ethyl]-2-oxoimidazolidin-1-yl}-2-(methylsulfonyl)ethanesulfonamide; HRMS: calcd for $C_{24}H_{31}N_3O_6S_2$+H+, 522.17270; found (ESI, [M+H]+Obs'd), 522.1730; HPLC Retention time, 3.0 min.

Compound 115: 2-({4-(4-methoxyphenyl)-3-[2-(4-methoxyphenyl)ethyl]-2-oxoimidazolidin-1-yl}sulfamoyl)acetamide; HRMS: calcd for $C_{21}H_{26}N_4O_6S+H+$, 463.16458; found (ESI, [M+H]+Obs'd), 463.1651; HPLC Retention time, 2.7 min.

Compound 116: tert-butyl ({4-(3,4-dimethylphenyl)-3-[2-(4-methoxyphenyl)ethyl]-2-oxoimidazolidin-1-yl}sulfamoyl)carbamate; HRMS: calcd for $C_{25}H_{34}N_4O_6S+H+$, 519.22718; found (ESI, [M+H]+Obs'd), 519.2282; HPLC Retention time, 2.9 min.

Compound 117: 4-{4-(4-tert-butylphenyl)-3-[2-(4-methoxyphenyl)ethyl]-2-oxoimidazolidin-1-yl}-N-methylpiperazine-1-carboxamide; HRMS: calcd for $C_{28}H_{39}N_5O_3+H+$, 494.31257; found (ESI, [M+H]+Obs'd), 494.3130; HPLC Retention time, 3.0 min.

Compound 118: N-[4-(4-tert-butylphenyl)-3-(2-{4-[2-(dimethylamino)ethoxy]phenyl}ethyl)-2-oxoimidazolidin-1-yl]methanesulfonamide; HRMS: calcd for $C_{26}H_{38}N_4O_4S+H+$, 503.26865; found (ESI, [M+H]+ Calc'd), 503.2686; HPLC Retention time, 2.9 min.

Compound 119: 1-amino-4-(4-tert-butylphenyl)-3-[3-(4-methoxyphenyl)propyl]imidazolidin-2-one; HRMS: calcd for $C_{23}H_{31}N_3O_2+H+$, 382.24890; found (ESI, [M+H]+Obs'd), 382.2495; HPLC Retention time, 3.1 min.

Compound 120: N-{4-(4-fluorobenzyl)-3-[2-(4-methoxyphenyl)ethyl]-2-oxoimidazolidin-1-yl}methanesulfonamide; HRMS: calcd for $C_{20}H_{24}FN_3O_4S+H+$, 422.15443; found (ESI, [M+H]+Obs'd), 422.1551; HPLC Retention time, 2.9 min.

Compound 121: 4-(4-tert-butylphenyl)-1-{[2-(1H-imidazol-1-yl)ethyl]amino}-3-[2-(4-methoxyphenyl)ethyl]imidazolidin-2-one; HRMS: calcd for $C_{27}H_{35}N_5O_2+H+$, 462.28635; found (ESI, [M+H]+Obs'd), 462.2868; HPLC Retention time, 3.1 min.

Compound 122: N-{4-(4-cyclopropylphenyl)-3-[2-(4-methoxyphenyl)ethyl]-2-oxoimidazolidin-1-yl}-2-pyridin-3-ylacetamide; HRMS: calcd for $C_{28}H_{30}N_4O_3+H+$, 471.23907; found (ESI, [M+H]+Obs'd), 471.2397; HPLC Retention time, 2.9 min.

Compound 123: 4-(4-tert-butylphenyl)-1-{[4-(diethylamino)benzyl]amino}-3-[2-(4-methoxyphenyl)ethyl]imidazolidin-2-one; HRMS: calcd for $C_{33}H_{44}N_4O_2+H+$, 529.35370; found (ESI, [M+H]+Obs'd), 529.3545; HPLC Retention time, 3.6 min.

Compound 124 4-(4-cyclopropylphenyl)-1-(1,1-dioxidoisothiazolidin-2-yl)-3-[2-(4-methoxyphenyl)ethyl]imidazolidin-2-one; HRMS: calcd for $C_{24}H_{29}N_3O_4S+H+$, 456.19515; found (ESI, [M+H]+Obs'd), 456.1958; HPLC Retention time, 3.0 min.

Compound 125: N-{4-(2,3-dihydro-1,4-benzodioxin-6-yl)-3-[2-(4-methoxyphenyl)ethyl]-2-oxoimidazolidin-1-yl}-2-morpholin-4-ylethanesulfonamide; HRMS: calcd for $C_{26}H_{34}N_4O_7S+H+$, 547.22210; found (ESI, [M+H]+Obs'd), 547.2225; HPLC Retention time, 2.7 min.

Compound 126: N-{4-(4-methoxyphenyl)-3-[3-(4-methoxyphenyl)propyl]-2-oxoimidazolidin-1-yl}-1-(methylsulfonyl)methanesulfonamide; HRMS: calcd for $C_{22}H_{29}N_3O_7S_2+H+$, 512.15197; found (ESI, [M+H]+Obs'd), 512.1520; HPLC Retention time, 2.8 min.

Compound 127: N-{4-(4-cyclopropylphenyl)-3-[3-(4-methoxyphenyl)propyl]-2-oxoimidazolidin-1-yl}-1-(methylsulfonyl)methanesulfonamide; HRMS: calcd for $C_{24}H_{31}N_3O_6S_2+H+$, 522.17270; found (ESI, [M+H]+Obs'd), 522.1728; HPLC Retention time, 3.0 min.

Compound 128: N-{4-butyl-3-[2-(4-methoxyphenyl)ethyl]-2-oxoimidazolidin-1-yl}methanesulfonamide; HRMS: calcd for $C_{17}H_{27}N_3O_4S+H+$, 370.17950; found (ESI, [M+H]+Obs'd), 370.1799; HPLC Retention time, 2.9 min.

Compound 129: 1-amino-4-(4-fluorobenzyl)-3-[2-(4-methoxyphenyl)ethyl]imidazolidin-2-one; HRMS: calcd for $C_{19}H_{22}FN_3O_2+H+$, 344.17688; found (ESI, [M+H]+Obs'd), 344.1774; HPLC Retention time, 2.8 min.

Compound 130: 4-{4-(4-tert-butylphenyl)-3-[2-(4-methoxyphenyl)ethyl]-2-oxoimidazolidin-1-yl}-N,N-dimethylpiperazine-1-carboxamide; HRMS: calcd for $C_{29}H_{41}N_5O_3+H+$, 508.32822; found (ESI, [M+H]+Obs'd), 508.3286; HPLC Retention time, 3.1 min.

Compound 131: 1-amino-4-(4-methoxyphenyl)-3-(3-phenylpropyl)imidazolidin-2-one. An alternative name for this compound is 1-Amino-3-(3-phenylpropyl)-4-(4-methoxyphenyl)-2-imidazolidinone; HRMS: calcd for $C_{19}H_{23}N_3O_2+H+$, 326.18630; found (ESI, [M+H]+Obs'd), 326.1863; HPLC Retention time, 2.8 min.

Compound 132: 2-(N-(4-(4-cyclopropylphenyl)-3-(4-methoxyphenethyl)-2-oxoimidazolidin-1-yl)sulfamoyl)-N-(2-(dimethylamino)-2-oxoethyl)-N-methylacetamide; HRMS: calcd for $C_{28}H_{37}N_5O_6S+H+$, 572.25373; found (ESI, [M+H]+Obs'd), 572.2541; HPLC Retention time, 2.9 min.

Compound 133: N-{4-(3,4-dimethylphenyl)-3-[2-(4-methoxyphenyl)ethyl]-2-oxoimidazolidin-1-yl}-N-(phenylsulfonyl)benzenesulfonamide; HRMS: calcd for $C_{32}H_{33}N_3O_6S_2+H+$, 620.18835; found (ESI, [M+H]+Obs'd), 620.1885; HPLC Retention time, 3.5 min.

Compound 134: N-{3-[2-(4-methoxyphenyl)ethyl]-2-oxo-4-(1-phenylcyclopropyl)imidazolidin-1-yl}-1-pyridin-3-ylmethanesulfonamide; HRMS: calcd for $C_{27}H_{30}N_4O_4S+H+$, 507.20605; found (ESI, [M+H]+Obs'd), 507.2064; HPLC Retention time, 2.9 min.

Compound 135: methyl 3-amino-4-({4-(3,4-dimethylphenyl)-3-[2-(4-methoxyphenyl)ethyl]-2-oxoimidazolidin-1-yl}amino)benzoate; HRMS: calcd for $C_{28}H_{32}N_4O_4+H+$, 489.24963; found (ESI, [M+H]$^+$), 489.2495; HPLC Retention time, 3.1 min.

Compound 136: N-(cyclopropylmethyl)-2-({(4R)-4-(4-methoxyphenyl)-3-[2-(4-methoxyphenyl)ethyl]-2-oxoimidazolidin-1-yl}sulfamoyl)acetamide; HRMS: calcd for $C_{25}H_{32}N_4O_6S+H+$, 517.21153; found (ESI, [M+H]+Obs'd), 517.2118; HPLC Retention time, 2.9 min.

Compound 137: N-{4-(4-fluorophenyl)-3-[2-(4-methoxyphenyl)ethyl]-2-oxoimidazolidin-1-yl}methanesulfonamide; HRMS: calcd for $C_{19}H_{22}FN_3O_4S+H+$, 408.13878; found (ESI, [M+H]+Obs'd), 408.1394; HPLC Retention time, 2.8 min.

Compound 138: 4-(3,4-dimethylphenyl)-3-[2-(4-methoxyphenyl)ethyl]-1-{[(1-methyl-1H-imidazol-2-yl)methyl]amino}imidazolidin-2-one; HRMS: calcd for $C_{25}H_{31}N_5O_2+H+$, 434.25505; found (ESI, [M+H]+Obs'd), 434.2550; HPLC Retention time, 2.9 min.

Compound 139: N-{4-(4-fluorophenyl)-3-[2-(4-methoxyphenyl)ethyl]-2-oxoimidazolidin-1-yl}-1-pyridin-3-ylmethanesulfonamide; HRMS: calcd for $C_{24}H_{25}FN_4O_4S+H+$, 485.16533; found (ESI, [M+H]+Obs'd), 485.1660; HPLC Retention time, 2.9 min.

Compound 140: N-{3-[2-(4-methoxyphenyl)ethyl]-2-oxo-4-(1-phenylcyclopropyl)imidazolidin-1-yl}methanesulfonamide; HRMS: calcd for $C_{22}H_{27}N_3O_4S+H+$, 430.17950; found (ESI, [M+H]+Obs'd), 430.1801; HPLC Retention time, 2.9 min.

Compound 141: 1-amino-4-[4-(2-methoxyethoxy)phenyl]-3-[2-(4-methoxyphenyl)ethyl]imidazolidin-2-one;

HRMS: calcd for $C_{21}H_{27}N_3O_4$+H+, 386.20743; found (ESI, [M+H]+Obs'd), 386.2077; HPLC Retention time, 2.6 min.

Compound 142: N-[3-{2-[4-(difluoromethoxy)phenyl]ethyl}-4-(4-methoxyphenyl)-2-oxoimidazolidin-1-yl]methanesulfonamide; HRMS: calcd for $C_{20}H_{23}F_2N_3O_5S$+H+, 456.13992; found (ESI, [M+H]+Obs'd), 456.1402; HPLC Retention time, 2.9 min.

Compound 143: N-{3-[2-(4-methoxyphenyl)ethyl]-2-oxo-4-quinolin-6-ylimidazolidin-1-yl}methanesulfonamide; HRMS: calcd for $C_{22}H_{24}N_4O_4S$+H+, 441.15910; found (ESI, [M+H]+Obs'd), 441.1595; HPLC Retention time, 2.6 min.

Compound 144: N-{4-(2,3-dihydro-1,4-benzodioxin-6-yl)-3-[2-(3,4-dimethoxyphenyl)ethyl]-2-oxoimidazolidin-1-yl}methanesulfonamide; HRMS: calcd for $C_{22}H_{27}N_3O_7S$+H+, 478.16425; found (ESI, [M+H]+Obs'd), 478.1648; HPLC Retention time, 2.6 min.

Compound 145: N-{4-cyclohexyl-3-[2-(4-methoxyphenyl)ethyl]-2-oxoimidazolidin-1-yl}methanesulfonamide; HRMS: calcd for $C_{19}H_{29}N_3O_4S$+H+, 396.19515; found (ESI, [M+H]+Obs'd), 396.1959; HPLC Retention time, 3.0 min.

Compound 146: tert-butyl {4-(4-tert-butylphenyl)-3-[2-(4-methoxyphenyl)ethyl]-2-oxoimidazolidin-1-yl}[2-(1H-imidazol-1-yl)ethyl]carbamate; HRMS: calcd for $C_{32}H_{43}N_5O_4$+H+, 562.33878; found (ESI, [M+H]+Obs'd), 562.3392; HPLC Retention time, 3.3 min.

Compound 147: N-{4-(4-tert-butylphenyl)-3-[2-(4-methoxyphenyl)ethyl]-2-oxoimidazolidin-1-yl}pyrazine-2-carboxamide; HRMS: calcd for $C_{27}H_{31}N_5O_3$+H+, 474.24997; found (ESI, [M+H]+Obs'd), 474.2505; HPLC Retention time, 3.1 min.

Compound 148: N-{4-(4-tert-butylphenyl)-3-[2-(4-methoxyphenyl)ethyl]-2-oxoimidazolidin-1-yl}-1,1,1-trifluoromethanesulfonamide; HRMS: calcd for $C_{23}H_{28}F_3N_3O_4S$+H+, 500.18254; found (ESI, [M+H]+Obs'd), 500.1827; HPLC Retention time, 2.9 min.

Compound 149: N-{3-[2-(4-methoxyphenyl)ethyl]-4-(6-methoxypyridin-3-yl)-2-oxoimidazolidin-1-yl}methanesulfonamide; HRMS: calcd for $C_{19}H_{24}N_4O_5S$+H+, 421.15402; found (ESI, [M+H]+Obs'd), 421.1547; HPLC Retention time, 2.6 min.

Compound 150: 4-{4-(4-tert-butylphenyl)-3-[2-(4-methoxyphenyl)ethyl]-2-oxoimidazolidin-1-yl}piperazine-1-carboxamide; HRMS: calcd for $C_{27}H_{37}N_5O_3$+H+, 480.29692; found (ESI, [M+H]+Obs'd), 480.2971; HPLC Retention time, 3.0 min.

Compound 151: N-{4-[4-(2-methoxyethoxy)phenyl]-3-[2-(4-methoxyphenyl)ethyl]-2-oxoimidazolidin-1-yl}methanesulfonamide; HRMS: calcd for $C_{22}H_{29}N_3O_6S$+H+, 464.18498; found (ESI, [M+H]+Obs'd), 464.1854; HPLC Retention time, 2.8 min.

Compound 152: N-[4-(4-methoxyphenyl)-2-oxo-3-{2-[4-(trifluoromethoxy)phenyl]ethyl}imidazolidin-1-yl]methanesulfonamide; HRMS: calcd for $C_{20}H_{22}F_3N_3O_5S$+H+, 474.13050; found (ESI, [M+H]+Obs'd), 474.1309; HPLC Retention time, 3.1 min.

Compound 153: N-{4-(4-methoxyphenyl)-3-[2-(4-methoxyphenyl)ethyl]-2-oxoimidazolidin-1-yl}-1-(methylsulfonyl)methanesulfonamide; HRMS: calcd for $C_{21}H_{27}N_3O_7S_2$+H+, 498.13632; found (ESI, [M+H]+Obs'd), 498.1366; HPLC Retention time, 2.8 min.

Compound 154: 1-amino-3-{2-[4-(difluoromethoxy)phenyl]ethyl}-4-(4-methoxyphenyl)imidazolidin-2-one; HRMS: calcd for $C_{19}H_{21}F_2N_3O_3$+H+, 378.16237; found (ESI, [M+H]+Obs'd), 378.1627; HPLC Retention time, 2.8 min.

Compound 155: 1-{4-(3,4-dimethylphenyl)-3-[2-(4-methoxyphenyl)ethyl]-2-oxoimidazolidin-1-yl}-3-phenylurea; HRMS: calcd for $C_{27}H_{30}N_4O_3$+H+, 459.23907; found (ESI, [M+H]+), 459.2393; HPLC Retention time, 3.1 min.

Compound 156: 1-amino-3-[2-(4-methoxyphenyl)ethyl]-4-(1-phenylcyclopropyl)imidazolidin-2-one; HRMS: calcd for $C_{21}H_{25}N_3O_2$+H+, 352.20195; found (ESI, [M+H]+Obs'd), 352.2025; HPLC Retention time, 2.8 min.

Compound 157: N-{4-(3,4-dimethylphenyl)-3-[2-(4-methoxyphenyl)ethyl]-2-oxoimidazolidin-1-yl}-N-[(1-methyl-1H-imidazol-2-yl)methyl]methanesulfonamide; HRMS: calcd for $C_{26}H_{33}N_5O_4S$+H+, 512.23260; found (ESI, [M+H]+Obs'd), 512.2333; HPLC Retention time, 3.0 min.

Compound 158: N-{4-(3,4-dimethoxyphenyl)-3-[2-(4-methoxyphenyl)ethyl]-2-oxoimidazolidin-1-yl}methanesulfonamide; HRMS: calcd for $C_{21}H_{27}N_3O_6S$+H+, 450.16933; found (ESI, [M+H]+Obs'd), 450.1695; HPLC Retention time, 2.7 min.

Compound 159: 1-amino-3-[2-(4-methoxyphenyl)ethyl]-4-(4-methylphenyl)imidazolidin-2-one. An alternative name for this compound is 1-Amino-3-[2-(4-methoxyphenyl)ethyl]-4-(4-methylphenyl)-2-imidazolidinone; HRMS: calcd for $C_{19}H_{23}N_3O_2$+H+, 326.18630; found (ESI, [M+H]+Obs'd), 326.1866; HPLC Retention time, 2.8 min.

Compound 160: N-{4-butyl-3-[2-(4-methoxyphenyl)ethyl]-2-oxoimidazolidin-1-yl}-1-pyridin-3-ylmethanesulfonamide; HRMS: calcd for $C_{22}H_{30}N_4O_4S$+H+, 447.20605; found (ESI, [M+H]+Obs'd), 447.2066; HPLC Retention time, 2.9 min.

Compound 161: 4-(3,4-dimethylphenyl)-3-[2-(4-methoxyphenyl)ethyl]-1-{[(1-oxidopyridin-4-yl)methyl]amino}imidazolidin-2-one; HRMS: calcd for $C_{26}H_{30}N_4O_3$+H+, 447.23907; found (ESI, [M+H]+), 447.2398; HPLC Retention time, 2.7 min.

Compound 162: N-{4,4-diethyl-3-[2-(4-methoxyphenyl)ethyl]-2-oxoimidazolidin-1-yl}-1-pyridin-3-ylmethanesulfonamide; HRMS: calcd for $C_{22}H_{30}N_4O_4S$+H+, 447.20605; found (ESI, [M+H]+Obs'd), 447.2065; HPLC Retention time, 2.8 min.

Compound 163: 1-amino-4-[1-(4-fluorophenyl)cyclopropyl]-3-[2-(4-methoxyphenyl)ethyl]imidazolidin-2-one; HRMS: calcd for $C_{21}H_{24}FN_3O_2$+H+, 370.19253; found (ESI, [M+H]+Obs'd), 370.1929; HPLC Retention time, 2.8 min.

Compound 164: 1-amino-4-(4-isopropoxyphenyl)-3-[2-(4-methoxyphenyl)ethyl]imidazolidin-2-one; HRMS: calcd for $C_{21}H_{27}N_3O_3$+H+, 370.21252; found (ESI, [M+H]+Obs'd), 370.2131; HPLC Retention time, 2.9 min.

Compound 165: N-{4-[1-(4-fluorophenyl)cyclopropyl]-3-[2-(4-methoxyphenyl)ethyl]-2-oxoimidazolidin-1-yl}methanesulfonamide; HRMS: calcd for $C_{22}H_{26}FN_3O_4S$+H+, 448.17008; found (ESI, [M+H]+Obs'd), 448.1707; HPLC Retention time, 2.9 min.

Compound 166: N-{4-(3,4-dimethylphenyl)-3-[2-(4-methoxyphenyl)ethyl]-2-oxoimidazolidin-1-yl}-4-methylpiperazine-1-sulfonamide; HRMS: calcd for $C_{25}H_{35}N_5O_4S$+H+, 502.24825; found (ESI, [M+H]+Obs'd), 502.2489; HPLC Retention time, 8.6 min.

Compound 167: N-{4-(4-methoxyphenyl)-3-[2-(4-methoxyphenyl)ethyl]-2-oxoimidazolidin-1-yl}sulfamide; HRMS: calcd for $C_{19}H_{24}N_4O_5S$+H+, 421.15402; found (ESI, [M+H]+Obs'd), 421.1539; HPLC Retention time, 2.7 min.

Compound 168: 2-(4-acetylpiperazin-1-yl)-N-{4-(4-methoxyphenyl)-3-[2-(4-methoxyphenyl)ethyl]-2-oxoimidazolidin-1-yl}-2-oxoethanesulfonamide; HRMS: calcd for $C_{27}H_{35}N_5O_7S+H+$, 574.23300; found (ESI, [M+H]+Obs'd), 574.2327; HPLC Retention time, 2.7 min.

Compound 169: N-[4-(4-tert-butylphenyl)-3-{2-[4-(2-morpholin-4-ylethoxy)phenyl]ethyl}-2-oxoimidazolidin-1-yl]methanesulfonamide; HRMS: calcd for $C_{28}H_{40}N_4O_5S+$H+, 545.27922; found (ESI, [M+H]+Obs'd), 545.2797; HPLC Retention time, 3.0 min.

Compound 170: N-{(4R)-4-[4-(difluoromethoxy)phenyl]-3-[2-(4-methoxyphenyl)ethyl]-2-oxoimidazolidin-1-yl}methanesulfonamide: MS 456 (MH$^+$); HPLC Retention time, 9.2 minutes with an Xterra RP18, 3.5 u, 150×4.6 mm column with a gradient of 85/15-5/95 (Ammon. Form. Buff. Ph=3.5/ACN+MeOH) for 10 min, hold 4 min.

Compound 171: N-{(4S)-4-[4-(difluoromethoxy)phenyl]-3-[2-(4-methoxyphenyl)ethyl]-2-oxoimidazolidin-1-yl}methanesulfonamide. MS 456 (MH$^+$); HPLC Retention time, 9.2 minutes with an Xterra RP18, 3.5 u, 150×4.6 mm column with a gradient of 85/15-5/95 (Ammon. Form. Buff. Ph=3.5/ACN+MeOH) for 10 min, hold 4 min.

Compound 172: N-{(4R)-4-(4-tert-butylphenyl)-3-[2-(4-methoxyphenyl)ethyl]-2-oxoimidazolidin-1-yl}methanesulfonamide; MS 446 (M+H), HPLC Retention time: 10.5 minutes in an HPLC with an Xterra RP18, 3.5 u, 150×4.6 mm column with a gradient of 85/15-5/95 (Ammon. Form. Buff. Ph=3.5/ACN+MeOH) for 10 min, hold 4 min.

Compound 173: N-{(4S)-4-(4-tert-butylphenyl)-3-[2-(4-methoxyphenyl)ethyl]-2-oxoimidazolidin-1-yl}methanesulfonamide; MS 446 (M+H), HPLC Retention time: 10.5 minutes in an HPLC with an Xterra RP18, 3.5 u, 150×4.6 mm column with a gradient of 85/15-5/95 (Ammon. Form. Buff. Ph=3.5/ACN+MeOH) for 10 min, hold 4 min.

Compound 174: [[[4-(4-cyclopropylphenyl)-3-[2-(4-methoxyphenyl)ethyl]-2-oxo-imidazolidin-1-yl]amino]sulfonyl]acetic acid. $^1$H NMR (CDCl$_3$) δ 8.03 (bs, 1H), 7.19 (d, J=8.4 Hz, 2H), 7.11 (d, J=8.1 Hz, 2H), 7.05 (m, 2H), 6.84 (m, 2H), 4.51 (t, J=8.4 Hz, 1H), 4.30 (s, 2H), 4.01 (t, J=8.7, 1H), 3.81 (s, 3H), 3.66 (m, 1H), 3.51 (m, 1H), 2.95 (m, 1H), 2.64 (m, 1H), 1.93 (m, 1H), 1.02 (m, 2H), 0.74 (m, 2H). MS 652 (MH$^+$). Anal. calcd. for $C_{23}H_{27}N_3O_6S\cdot¼C_4H_{10}O$: C, 58.58; H, 6.04; N, 8.54. Found: C, 58.37; H, 6.01; N, 8.35

Compound 175: 1-amino-4-(4-methoxyphenyl)-3-[2-(4-methoxyphenyl)ethyl]imidazolidin-2-one: $^1$H-NMR (DMSO-d$_6$): ? 7.50 (d, J=8.1 Hz, 2H), 7.33 (d, J=8.1 Hz, 2H), 7.14 (d, J=8.2 Hz, 2H), 7.04 (d, J=8.4 Hz, 2H), 7.01 (d, J=8.2 Hz, 2H), 6.82 (d, J=8.4 Hz, 2H), 4.68 (t, J=7.8 Hz, 1H), 3.84 (t, J=7.8 Hz, 1H), 3.79 (s, 3H), 3.71 (s, 3H), 3.55 (m, 1H), 3.24 (t, J=8.1 Hz, 1H), 2.64 (m, 3H), 2.52 (m, 2H), 2.30 (s, 3H). MS m/z (ESI, positive): 342 [M+H]$^+$. This compound was isolated as the p-toluene sulfonic acid salt.

Compound 176: 1-(Aminosulfonylamino)-3-[2-(4-methoxyphenyl)propyl]-4-[(4-methoxy)phenyl]-2-imidazolidinone Compound 177: 1-({[(2,2-Dimethyl-2-hydroxy-1-methylethyl)amino]-2-oxoethyl}sulfonylamino)-3-[2-(4-methoxyphenyl)ethyl]-4-(4-cyclopropylphenyl)-2-imidazolidinone Compound 178: 1-[[2-[(Cyclopropylmethyl)amino]-2-oxoethyl]sulfonylamino]-3-[2-(4-cyclopropylphenyl)ethyl]-4-(4-methoxyphenyl)-2-imidazolidinone:

Compound 179: N-{4-(Cyclopropylphenyl)-3-[2-(4-methoxyphenyl)ethyl]-2-oxo-imidazolidin-1-yl}-2-dimethylsulfamoyl-acetamide Compound 180: 1-[(2-Amino-2-oxoethyl)sulfonylamino]-3-[2-(4-methoxyphenyl)propyl]-4-(4-cyclopropylphenyl)-2-imidazolidinone Compound 181: 1-[(N-Methyl-N-methylsulfonyl)amino]-3-[2-(4-methoxy-phenyl)ethyl]-4-(3,4-dimethylphenyl)-2-imidazolidinone Compound 182: 1-[(N-Methyl-N-phenylsulfonyl)amino]-3-[2-(4-methoxyphenyl)-ethyl]-4-(3,4-dimethylphenyl)-2-imidazolidinone Compound 183: (S)-1-[[2-[(Cyclopropylmethyl)amino]-2-oxoethyl]sulfonylamino]-3-[2-(4-methoxyphenyl)ethyl]-4-(4-methoxyphenyl)-2-imidazolidinone Compound 184: 1-(Methylsulfonylamino)-3-[2-(4-Methoxyphenyl)ethyl]-4-(R)-(3,4-dimethylphenyl)-2-imidazolidinone Compound 185: 1-(Methylsulfonylamino)-3-[2-(4-Methoxyphenyl)ethyl]-4-(R)-(4-methoxyphenyl)-2-imidazolidinone Compound 186: 1-(Methylsulfonylamino)-3-[2-(4-Methoxyphenyl)ethyl]-4-(R)-(4-tert-butylphenyl)-2-imidazolidinone: MS: 46 (M+H) HPLC Retention time: 10.5 minutes in an HPLC with an Xterra RP18, 3.5 u, 150×4.6 mm column with a gradient of 85/15-5/95 (Ammon. Form. Buff. Ph=3.5/ACN+MeOH) for 10 min, hold 4 min Compound 187: 1-(Methylsulfonylamino)-3-[2-(4-Methoxyphenyl)ethyl]-4-(R)-(4-cyclopropylphenyl)-2-imidazolidinone Compound 188: 1-(Methylsulfonylamino)-3-(3-phenylpropyl)-4-(R)-(3,4-dimethylphenyl)-2-imidazolidinone Compound 189: 1-(Methylsulfonylamino)-3-(3-phenylpropyl)-4-(R)-(4-methoxyphenyl)-2-imidazolidinone Compound 190: 1-(Methylsulfonylamino)-3-(3-phenylpropyl)-4-(R)-(4-tert-butylphenyl)-2-imidazolidinone Compound 191: 1-(Methylsulfonylamino)-3-(3-phenylpropyl)-4-(R)-(4-cyclopropylphenyl)-2-imidazolidinone Compound 192: 1-(Methylsulfonylamino)-3-[2-(4-Methoxyphenyl)ethyl]-4-(S)-(3,4-dimethylphenyl)-2-imidazolidinone Compound 193: 1-(Methylsulfonylamino)-3-[2-(4-Methoxyphenyl)ethyl]-4-(S)-(4-methoxyphenyl)-2-imidazolidinone Compound 194: 1-(Methylsulfonylamino)-3-[2-(4-Methoxyphenyl)ethyl]-4-(S)-(4-tert-butylphenyl)-2-imidazolidinone. MS: 46 (M+H) HPLC Retention time: 10.5 minutes in an HPLC with an Xterra RP18, 3.5 u, 150×4.6 mm column with a gradient of 85/15-5/95 (Ammon. Form. Buff. Ph=3.5/ACN+MeOH) for 10 min, hold 4 min Compound 195: 1-(Methylsulfonylamino)-3-[2-(4-Methoxyphenyl)ethyl]-4-(S)-(4-cyclopropylphenyl)-2-imidazolidinone Compound 196: 1-(Methylsulfonylamino)-3-(3-phenylpropyl)-4-(S)-(3,4-dimethylphenyl)-2-imidazolidinone Compound 197: 1-(Methylsulfonylamino)-3-(3-phenylpropyl)-4-(S)-(4-methoxyphenyl)-2-imidazolidinone Compound 198: 1-(Methylsulfonylamino)-3-(3-phenylpropyl)-4-(S)-(4-tert-butylphenyl)-2-imidazolidinone Compound 199: 1-(Methylsulfonylamino)-3-(3-phenylpropyl)-4-(S)-(4-cyclopropylphenyl)-2-imidazolidinone Compound 200: (R)-1-[[2-[(Cyclopropylmethyl)amino]-2-oxoethyl]sulfonylamino]-3-[2-(4-methoxyphenyl)ethyl]-4-(4-methoxyphenyl)-2-imidazolidinone Compound 201: 1-{[2-(cyclopropylamino)-2-oxoethyl]sulfonylamino}-3-[2-(4-methoxyphenyl)ethyl]-4-(4-cyclopropylphenyl)-2-imidazolidinone. $^1$H NMR (CDCl$_3$) δ 8.43 (d, J=3.6 Hz, 1H), 7.12 (m, 5H), 7.06 (m, 2H), 6.83 (m, 2H), 4.49 (t, J=8.4 Hz, 1H), 4.00 (m, 3H), 3.80 (s, 3H), 3.68 (m, 1H), 3.42 (m, 1H), 3.42 (m, 1H), 2.95 (m, 1H), 2.86 (m, 1H), 2.72 (m, 1H), 2.65 (m, 1H), 1.93 (m, 1H), 1.01 (m, 2H), 0.83 (m, 2H), 0.74 (m, 2H), 0.64 (m, 2H). MS 513 (MH$^+$). Anal. calcd. for $C_{26}H_{32}N_4O_5S\cdot½H_2O$: C, 59.87; H, 6.38; N, 10.74. Found: C, 59.62; H, 6.14; N, 10.49.

Compound 202: 1-[[(Dimethylamino)sulfonyl]acetylamino]-3-[2-(4-methoxy-phenyl)ethyl]-4-(4-cyclopropylphenyl)-2-imidazolidinone Compound 203: 1-[[2-[(Cyclopropylmethyl)amino]-2-oxoethyl]sulfonylamino]-3-[2-(4-cyclo-propylphenyl)ethyl]-4-(4-methoxyphenyl)-2-imidazolidinone HPLC Conditions for compounds 109-169 were as follows: Column: BDS Hypersil C8; mobile phase A: 10 mM $NH_4OAC$ in 95% water/5% ACN (pipette 6.67 mL of 7.5 M $NH_4OAC$ solution into 4743 mL $H_2O$, then add 250 mL of ACN to the solution and mix.); mobile phase B: 10 mM $NH_4OAC$ in 5% water/95% ACN (pipette 6.67 mL of 7.5 M $NH_4OAC$ solution into 243 mL $H_2O$. Then add 4750 mL of ACN to the solution and mix.); flow Rate: 0.800 mL/min; column Temperature: 40° C.; injection Volume: 5 ☒L; UV: monitor 214 nm and 254 nm; gradient table (time (min)/% B): 0.0/0; 2.5/100; 4.0/100; 4.1/0; 5.5/0.

Compounds listed and described herein have been found in many instances to exhibit activities (e.g., $IC_{50}$ in the assays described-or referenced herein) at a concentration below 1 micromolar (μM). For certain of the compounds of the present invention, activity levels at 1.0 μM were undetectable in the Kv1.5 Patch Clamp EP assay described herein. Although these compounds were not tested at higher concentrations, it is believed that they would demonstrate measurable activity at higher concentrations.

Compounds of the present invention are effective as Kv1.5 potassium channel inhibitors. Accordingly, compounds of the present invention can be used to prevent or treat conditions that can be affected by inhibition of Kv1.5 potassium channel.

Compounds of the present invention can be used to treat or prevent cardiac arrhythmias, including atrial fibrillation and flutter. In preferred embodiments, compounds of the present invention are capable of inhibiting Kv1.5 potassium channels while having little or no inhibitory effect on other ion channels in heart, including for example, ion channels in the ventricles. Accordingly, in preferred embodiments, compounds of the present invention will prevent or treat cardiac arrhythmia while avoiding some of the common complications typically associated with inhibition of ion channels in the heart, including, for example, a prolongation of the QT interval and an increased propensity for life threatening ventricular arrhythmias.

Compounds of the present invention can be used to treat or prevent atrial arrhythmias, including atrial fibrillation and atrial flutter, as well as conditions associated with atrial arrhythmias, including, for example, thromboembolism, stroke, and heart failure.

Compounds of the present invention can be used to produce long-term, as well as short term maintenance periods free of arrhythmia in patients with persistent or chronic atrial arrhythmias.

Compounds of the present invention can also be used to prophylacticly treat post surgical atrial arrhthmias.

Methods of the present invention thus include methods of inhibiting Kv1.5 potassium channel; methods of inhibiting Kv1.5 potassium channels while having little or no inhibitory effect on other ion channels in heart, including for example, ion channels in the ventricles; methods of treating or preventing cardiac arrhythmias, including atrial fibrillation and flutter; methods for treating or preventing conditions associated with atrial arrhythmias, including, for example, thromboembolism, stroke, and heart failure; methods for producing long-term, as well as short term maintenance periods free of arrhythmia in patients with persistent or chronic atrial arrhythmias; and methods for prophylacticly treating post surgical atrial arrhthmias. The methods can comprise administering an effective amount of a compound or composition of the present invention to a subject.

The present invention also relates to the use of the compounds according to the present invention in the manufacture of a medicament for the treatment or prevention of atrial arrhythmias and related disorders.

Formulations

The present invention also relates to compositions or formulations which comprise the Kv1.5 potassium channel inhibitors according to the present invention. In general, the compositions of the present invention comprise an effective amount of one or more 1-N-amino-2-imidazolidinones and salts thereof according to the present invention which are effective for providing atrial-selective antiarrhythmia and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known antiarrhythmic agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, pre-filled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases, it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human. The present teachings accordingly provide methods of treating or inhibiting a pathological condition or disorder by providing to a mammal a compound of the present teachings including its pharmaceutically acceptable salt or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder. As used herein, "therapeutically effective" refers to a substance or an amount that elicits a desirable biological activity or effect. As used herein, "treating" refers to partially or completely alleviating, inhibiting, preventing, and/or ameliorating the condition.

Non-limiting examples of compositions according to the present invention include composition having from about 0.001 mg to about 1000 mg of one or more 1-N-amino-2-imidazolidinones according to the present invention and one or more excipients; from about 0.01 mg to about 100 mg of one or more 1-N-amino-2-imidazolidinones according to the present invention and one or more excipients; and from about 0.1 mg to about 10 mg of one or more 1-N-amino-2-imidazolidinones according to the present invention and one or more excipients.

The term "effective amount" as used herein means "an amount of one or more 1-N-amino-2-imidazolidinones, effective at dosages and for periods of time necessary to achieve the desired or therapeutic result." An effective amount may vary according to factors known in the art, such as the disease state, age, sex, and weight of the subject being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present invention can be administered as frequently as necessary to achieve a therapeutic amount.

Procedures

The following procedures are utilized in evaluating and selecting compounds as the Kv1.5 potassium channel inhibitors.

FLIPR L-Type Calcium Channel Assay[1,2]

HL-1 cells expressing endogenous L-type calcium channels are removed from culture flasks using trypsin, plated on fibronectin/gelatin-coated, clear-bottomed, black-walled 96-well microplates in Claycomb media (JRH Biosciences #51800) containing 10% fetal bovine serum, 4 mM L-glutamine, and 10 μM norepinephrine, and grown to confluency overnight. The next day, growth medium is aspirated from confluent cell monolayers and replaced with 100 μL per well Tyrode's solution (in mM: 130 NaCl, 4 KCl, 1.8 $CaCl_2$, 1.0 $MgCl_2$, 20 HEPES, 10 glucose, pH 7.35) and 50 μL per well FLIPR Calcium Assay kit, component A (#R-8033, Molecular Devices Corporation) and incubated for 60 min. in a 5% $CO_2$ 37° C. incubator. 50 μL per well test compounds are added to the plates and further incubated for 15 min. in a 5% $CO_2$ 37° C. incubator. All final solutions contain the anion exchange inhibitor, probenecid (2.5 mM). The 96-well plates are then placed in the center position of the FLIPR 1 (Fluorometric Imaging Plate Reader, Molecular Devices Corporation). Cell monolayers in each well are simultaneously illuminated at 488 nm with an Argon ion laser, and fluorescence emission is monitored using a 510-570 nm bandpass filter and a cooled CCD camera. To depolarize the plasma membrane and activate L-type calcium channels, 50 μL per well of 20 mM KCl (final concentration) are dispensed simultaneously to all 96 wells using the FLIPR's automatic 96-well pipettor. Fluorescence measurements are captured for 5 min. following KCl addition. Calcium influx, expressed as % control, is calculated for each concentration of test compound and concentration-response curves and IC50 values are generated using GraphPad Prism 4.0.

Kv1.5 Patch Clamp EP

Kv1.5 currents are recorded by the whole cell mode of patch clamp electrophysiology.[1] Kv1.5 is stably over expressed in either HEK or LTK-cells. Microelectrodes are pulled from borosilicate glass (TW150) and heat polished (tip resistance, 1.5 to 3 megaohms). The external solution is standard Tyrodes solution. The internal (microelectrode) solution contained: 110 mM KCl, 5 mM $K_2ATP$, 5 mM $K_4BAPTA$, 1 mM $MgCl_2$ and 10 mM HEPES, adjusted to pH 7.2 with KOH. Command potentials are applied for 1 second to +60 mV from a holding potential of −70 mV using Axon software (pClamp 8.1) and hardware (Axopatch 1D, 200B). Compounds are prepared as 10-20 mM DMSO stocks and diluted to appropriate test concentrations. After stable currents are achieved, compounds are perfused onto the cells and the cells are pulsed every 5 seconds until no further changes in current are evident at a given compound concentration. Inhibition was measured at the end of the 1 second pulses and expressed relative to controls. Initial Kv1.5 inhibition is estimated by single point determinations done at 1 μM. Concentration response curves are generated for appropriate compounds utilizing at least four concentrations and an n=3. Curve fitting and $IC_{50}$ estimating are done using Graphpad software (Ver. 4).

HERG Patch Clamp EP

HERG currents are recorded by the whole cell mode of patch clamp electrophysiology as described by Hamill et al.[3] HERG is stably over expressed in HEK cells. Microelectrodes are pulled from borosilicate glass (TW150) and heat polished (tip resistance, 1.5 to 3 megaohms). The external solution is standard Tyrodes solution. The internal (microelectrode) solution contained: 110 mM KCl, 5 mM $K_2ATP$, 5 mM $K_4BAPTA$, 1 mM $MgCl_2$ and 10 mM HEPES, adjusted to pH 7.2 with KOH. Command potentials are applied for 2 seconds to +20 mV from a holding potential of −80 mV using Axon software (pClamp 8.1) and hardware (Axopatch 1D, 200B). Tail currents are generated by returning to −40 mV for 2 seconds. Compounds are prepared as 10-20 mM DMSO stocks and diluted to appropriate test concentrations. After stable currents are achieved, compounds are perfused onto the cells and the cells are pulsed every 20 seconds until no further changes in current are evident at a given compound concentration. Inhibition of HERG is measured at the peak of the tail currents and expressed relative to controls. Initial HERG activity is estimated by single point determinations run at 10 μM. Concentration response curves are generated for appropriate compounds utilizing at least four concentrations and an n=3. Curve fitting and $IC_{50}$ estimating are done using Graphpad software (Ver. 4).

1. Claycomb W. C. et al., "HL-1 cells: A cardiac muscle cell line that contracts and retains phenotypic characteristics of the adult cadiomyocyte." *Proc Natl Acad Sci USA* 1998 Mar. 17; 95(6): 2979-84.
2. Xia M et al., "Functional expression of L- and T-type $Ca^{2+}$ channels in murine HL-1 cells." *J. Mol. Cell Cardiol.*, 204 January; 3(1): 111-9.
3. Hamill et al., *Pflugers Archiv.* 391:85, 1981.

Results for representative compounds according to the present invention are listed in Table XI below.

TABLE XI

| Compound Number | [1]Kv1.5% inhibition @ 1.0 μM | [2]L-type $Ca^{2+}$ $IC_{50}$ μM | [3]HERG % Inhib. @ 10 μM | [1]Kv1.5 $IC_{50}$ nM | [3]HERG $IC_{50}$ μM |
|---|---|---|---|---|---|
| 1 | 59 | 5.5 | | | |
| 2 | 46 | | | | |
| 3 | 13 | | | | |
| 4 | 72 | 4.5 | 53 | | |
| 5 | 36 | | | | |
| 6 | 53 | 12 | 29 | | |
| 7 | 92 | 43 | 16 | 232 | |
| 8 | 90 | 15 | 16 | | |
| 9 | 90 | 23 | 62 | 689 | 7.3 |
| 10 | 89 | 22 | 57 | 238 | |
| 11 | 95 | 13 | 45 | | |
| 12 | 82 | 38 | 19 | | |
| 13 | 83 | 27 | 10 | | |
| 14 | 28 | | | | |
| 15 | 46 | | | | |
| 16 | 48 | | | | |
| 17 | 89 | 40 | 22 | | |
| 18 | 59 | 24 | 12 | | |
| 19 | 27 | | | | |
| 20 | 73 | 30 | 15 | | |
| 21 | 72 | 26 | 57 | | |
| 22 | 30 | | | | |
| 23 | 66 | 30 | 21 | 703 | 23.6 |
| 24 | 82 | 10 | 74 | 514 | 6.4 |
| 25 | 84 | 28 | 31 | | |
| 26 | 66 | 17.5 | 76 | 716 | 4.1 |
| 27 | 56 | 19 | 63 | | |
| 28 | 89 | 16 | 30 | 184 | 10.3 |
| 29 | 85 | 34 | 31 | | |
| 30 | 88 | 3.3 | 62 | | |
| 31 | 84 | 4 | | | |
| 32 | 69 | 6.7 | | | |
| 33 | 85 | 35 | 20 | | |
| 34 | 98 | 18 | 38 | | |
| 35 | 71 | 30 | 14 | | |
| 36 | 85 | 14 | 50 | | |
| 37 | 87 | 30 | 6 | | |
| 38 | 85 | 5.6 | 56 | | |
| 39 | 81 | 12 | | | |
| 40 | 70 | 30 | 1 | | |
| 41 | 42 | | | | |
| 42 | 91 | 20 | 90 | 418 | |
| 43 | 93 | 4.3 | 2 | | |
| 44 | 60 | 25 | 22 | | |
| 45 | 83 | 16 | 55 | | |
| 46 | 40 | | | | |
| 47 | 73 | 26 | 65 | | |
| 48 | 96 | 9 | 70 | 231 | 3.6 |
| 49 | 76 | 23 | 25 | 466 | 11.4 |
| 50 | 79 | 10 | 34 | 233 | 5.3 |
| 51 | 87 | 21 | 20 | | |
| 52 | 80 | 16 | 29 | | |
| 54 | 80 | 30 | 46 | | |
| 55 | 29 | 29 | | | |
| 56 | 39 | | | | |
| 57 | 66 | 30 | 12 | 631 | 12.4 |
| 60 | 77 | 10.6 | 44 | 453 | 7.4 |
| 61 | 85 | 25 | 28 | | |
| 62 | 26 | | | | |
| 63 | 95 | 6.3 | 44 | | |
| 64 | 96 | 14 | 55 | | |
| 65 | 88 | 31 | 38 | | |
| 66 | 86 | 30 | | 257 | 12.6 |
| 67 | 90 | 8 | 22 | | |
| 68 | 60 | 16 | 48 | | |
| 69 | Not detected | | | | |
| 70 | 22 | | | | |
| 71 | 94 | 13 | 30 | | |
| 72 | 81 | 18 | | | |
| 73 | 62 | 7 | 56 | 658 | |
| 74 | 85 | 25 | | | |

TABLE XI-continued

| Compound Number | $^1$Kv1.5% inhibition @ 1.0 μM | $^2$L-type Ca$^{2+}$ IC$_{50}$ μM | $^3$HERG % Inhib. @ 10 μM | $^1$Kv1.5 IC$_{50}$ nM | $^3$HERG IC$_{50}$ μM |
|---|---|---|---|---|---|
| 75 | Not detected | | | | |
| 76 | Not detected | | | | |
| 77 | Not detected | | | | |
| 78 | 75 | 11 | | | |
| 79 | 68 | 11 | 70 | | |
| 80 | 77 | 20 | 51 | | |
| 81 | 78 | 4 | | | |
| 82 | 72 | 30 | 42 | | |
| 83 | 96 | 2.8 | 97 | | |
| 84 | 67 | 10 | 73 | 570 | |
| 85 | 92 | 3.3 | 52 | | |
| 86 | 20 | | | | |
| 87 | 57 | 6 | | | |
| 88 | 94 | 11 | 90 | 399 | |
| 89 | 85 | 7.6 | 98 | | |
| 90 | 74 | 7 | 28 | | |
| 91 | 85 | 4 | | | |
| 92 | 95 | 30 | 58 | 353 | 5.6 |
| 93 | 46 | | | | |
| 94 | 67 | 13 | 35 | | |
| 95 | 43 | | | | |
| 96 | 86 | 1.9 | 87 | | |
| 97 | 81 | 3.5 | | | |
| 98 | 83 | 4.8 | | | |
| 99 | 73 | 4.9 | 90 | | |
| 100 | 46 | 16 | 92 | | |
| 101 | 81 | 19 | 24 | | |
| 102 | 6 | | | | |
| 104 | 87 | 21 | 56 | | |
| 106 | 74 | 30 | 17 | 474 | 35 |
| 107 | 41 | 39 | | 1100 | 54 |
| 108 | Not detected | | | | |
| 109 | 71 | 4.6 | | | |
| 110 | 7 | | | | |
| 111 | 9 | | 33 | | |
| 112 | 8 | | | | |
| 113 | 5 | | | | |
| 114 | 75 | 15 | 55 | | |
| 115 | 5 | | | | |
| 116 | Not detected | | | | |
| 117 | 19 | | | | |
| 118 | 9 | | | | |
| 119 | 80 | 2 | 70 | | |
| 120 | 5 | | | | |
| 121 | 7 | | | | |
| 122 | 36 | | | | |
| 123 | 25 | | | | |
| 124 | 38 | | | | |
| 125 | 42 | | | | |
| 126 | 46 | | | | |
| 127 | 91 | 19 | 54 | | |
| 128 | 8 | | 19 | | |
| 129 | 4 | | | | |
| 130 | 37 | | | | |
| 131 | Not detected | | | | |
| 132 | 3 | | | | |
| 133 | Not detected | | | | |
| 134 | 22 | | | | |
| 135 | 53 | 8 | | | |
| 136 | 44 | | | | |
| 137 | 4 | | | | |
| 138 | 7 | | | | |
| 139 | 14 | | | | |
| 140 | 6 | | | | |
| 141 | 4 | | | | |
| 142 | 40 | | 91 | | |
| 143 | 21 | | | | |
| 144 | 16 | | | | |
| 145 | 16 | | 11 | | |
| 146 | 83 | 15 | 86 | | |
| 147 | 42 | | | | |
| 148 | 2 | | | | |
| 149 | 9 | | | | |
| 150 | 17 | | | | |
| 151 | 8 | | | | |
| 152 | 16 | | | | |
| 153 | 12 | | | | |
| 154 | 7 | | | | |
| 155 | Not detected | | | | |
| 156 | 7 | | | | |
| 157 | Not detected | | | | |
| 158 | 10 | | | | |
| 159 | 4 | | | | |
| 160 | Not detected | | | | |
| 161 | 8 | | | | |
| 162 | 8 | | | | |
| 163 | 16 | | | | |
| 164 | 2 | | | | |
| 165 | 11 | | | | |
| 166 | 41 | | | | |
| 167 | 36 | | | | |
| 168 | Not detected | | | | |
| 169 | 16 | | | | |
| 170 | 49 | 30 | 62 | | |
| 171 | 71 | 30 | 55 | 531 | 5.8 |
| 172 | 55 | 9.8 | 51 | | |
| 173 | 94 | 14.6 | 48 | | |
| 174 | 9 | | | | |
| 175 | 7 | | | | |

$^1$Kv1.5 Patch Clamp EP as described herein
$^2$FLIPR L-type Calcium Channel Assay as described herein
$^3$HERG Patch Clamp EP as described herein above The following are additional methods used to determine the suitability of the compounds of the present invention for use as Kv1.5 potassium channel inhibitors.

In Vivo Test

Vehicle: Compounds are dissolved to a final concentration of 20-50 mg/ml, first in dimethyl acetamide (DMAC) then adding the balance of propylene glycol 200 (PEG200) for a ratio of DMAC/PEG200 (1:4).

Miniswine: The animals are induced with an IM injection of ketamine/xylazine followed briefly by 1-1.5% isoflurane if needed for introduction of a line into the vena cava in the neck. Following intubation, anesthesia is maintained with IV pentobarbital alone with boluses given every 30 minutes during the study. Two electrode-tipped catheters are introduced via the jugular, one into the right atrium and the other into the right ventricle. The carotid artery is isolated and a transducer-tipped catheter introduced into the left ventricle. An incision in the groin is used to access the femoral artery and vein. The artery is cannulated to monitor arterial pressure at the lower aorta and the vein is cannulated with an electrode-tipped catheter advanced into the right atrium. An incision is made above the fourth intercostal space and the ribs separated for access to the heart. The pericardium is opened and the left atrium is loosely clamped to the chest wall. A sensing and two pacing electrodes are placed on the atrium. The arterial pressure, ECG, LV pressure, atrial electrogram, body temperature, and exhaled PCO$_2$ are monitored continuously.

When the surgical preparation is stable, baseline effective refractory periods (ERPs) are determined at paced rates of 150, 200, 240, and 300 beats per minute from the right and left atriums, and the right ventricle. Compound is then infused over 15 minutes and the ERP determinations are repeated starting at the 12th minute of the infusion. The animal is allowed to stabilize, then about 15 minutes after the first dose a second dose is given over 15 minutes followed by ERPs. A third dose may be given. After the final dose the ERPs are determined every 15 minutes until the values are back at baseline. Blood samples are collected at baseline, at the end of each dose, and 15 minutes after the final dose.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. The compound 1-(Methylsulfonylamino)-3-[2-(4-methoxyphenyl)ethyl]-4-(4-methoxyphenyl)-2-imidazolidinone or a pharmaceutically acceptable salt form thereof.

2. A composition comprising an effective amount of a compound according to claim 1 or a pharmaceutically acceptable salt form thereof and one or more excipients.

3. A method for treating atrial arrhythmias comprising administering to a subject an effective amount of a compound according to claim 1 or a pharmaceutically acceptable salt form thereof.

4. The compound 1-[(Methylsulfonyl)amino]-3-[2-(4-methoxyphenyl)ethyl]-4-(4-difluoro-methoxyphenyl)-2-imidazolidinone or a pharmaceutically acceptable salt form thereof.

5. A composition comprising an effective amount of a compound according to claim 4 or a pharmaceutically acceptable salt form thereof and one or more excipients.

6. A method for treating atrial arrhythmias comprising administering to a subject an effective amount of a compound according to claim 4 or a pharmaceutically acceptable salt form thereof.

7. The compound 1-[[2-[(Cyclopropylmethyl)amino]-2-oxoethyl]sulfonylamino-3-[2-(4-methoxy-phenyl)ethyl]-4-(4-methoxyphenyl)-2-imidazolidinone or a pharmaceutically acceptable salt form thereof.

8. A composition comprising an effective amount of a compound according to claim 7 or a pharmaceutically acceptable salt form thereof and one or more excipients.

9. A method for treating atrial arrhythmias comprising administering to a subject an effective amount of a compound according to claim 7 or a pharmaceutically acceptable salt form thereof.

10. The compound 1-(Methylsulfonylamino)-3-[3-(4-methoxyphenyl)propyl]-4-[(4-tert-butyl)phenyl]-2-imidazolidinone or a pharmaceutically acceptable salt form thereof.

11. A composition comprising an effective amount of a compound according to claim 10 or a pharmaceutically acceptable salt form thereof and one or more excipients.

12. A method for treating atrial arrhythmias comprising administering to a subject an effective amount of a compound according to claim 10 or a pharmaceutically acceptable salt form thereof.

13. The compound N-{4-(4-cyclopropylphenyl)-3-[3-(4-methoxyphenyl)propyl]-2-oxoimidazolidin-1-yl}-1-(methylsulfonyl)methanesulfonamide or a pharmaceutically acceptable salt form thereof.

14. A composition comprising an effective amount of a compound according to claim 13 or a pharmaceutically acceptable salt form thereof and one or more excipients.

15. A method for treating atrial arrhythmias comprising administering to a subject an effective amount of a compound according to claim 13 or a pharmaceutically acceptable salt form thereof.

16. The compound 1-(Methylsulfonylamino)-3-[2-(4-methoxyphenyl)ethyl]-4-(4-chlorophenyl)-2-imidazolidinone or a pharmaceutically acceptable salt form thereof.

17. A composition comprising an effective amount of a compound according to claim 16 or a pharmaceutically acceptable salt form thereof and one or more excipients.

18. A method for treating atrial arrhythmias comprising administering to a subject an effective amount of a compound according to claim 16 or a pharmaceutically acceptable salt form thereof.

19. The compound 1-[(Methylsulfonyl)amino]-3-[(4-methoxyphenyl)ethyl]-4-(4-cyclopropylphenyl)-2-imidazolidinone or a pharmaceutically acceptable salt form thereof.

20. A composition comprising an effective amount of a compound according to claim 19 or a pharmaceutically acceptable salt form thereof and one or more excipients.

21. A method for treating atrial arrhythmias comprising administering to a subject an effective amount of a compound according to claim 19 or a pharmaceutically acceptable salt form thereof.

22. The compound N-{(4S)-4-(4-methoxyphenyl)-3-[2-(4-methoxyphenyl)ethyl]-2-oxoimidazolidin-1-yl}methanesulfonamide or a pharmaceutically acceptable salt form thereof.

23. A composition comprising an effective amount of a compound according to claim 22 or a pharmaceutically acceptable salt form thereof and one or more excipients.

24. A method for treating atrial arrhythmias comprising administering to a subject an effective amount of a compound according to claim 22 or a pharmaceutically acceptable salt form thereof.

25. The compound 1-(Methylsulfonylamino)-3-[2-(4-methoxyphenyl)ethyl]-4-[(4-diethylamino)-phenyl]-2-imidazolidinone or a pharmaceutically acceptable salt form thereof.

26. A composition comprising an effective amount of a compound according to claim 25 or a pharmaceutically acceptable salt form thereof and one or more excipients.

27. A method for treating atrial arrhythmias comprising administering to a subject an effective amount of a compound according to claim 25 or a pharmaceutically acceptable salt form thereof.

28. The compound 1-(Methylsulfonylamino)-3-[2-(4-Methoxyphenyl)ethyl]-4-(R)-(4-methoxyphenyl)-2-imidazolidinone or a pharmaceutically acceptable salt form thereof.

29. A composition comprising an effective amount of a compound according to claim 28 or a pharmaceutically acceptable salt form thereof and one or more excipients.

30. A method for treating atrial arrhythmias comprising administering to a subject an effective amount of a compound according to claim 28 or a pharmaceutically acceptable salt form thereof.

* * * * *